US00RE36713E

United States Patent [19]

Vogelstein et al.

[11] E Patent Number: Re. 36,713

[45] Reissued Date of Patent: May 23, 2000

[54] APC GENE AND NUCLEIC ACID PROBES DERIVED THEREFROM

[75] Inventors: Bert Vogelstein, Baltimore; Kenneth W. Kinzler, BelAir, both of Md.; Hans Albertson, Salt Lake City, Utah; Rakesh Anand, Sandbach, United Kingdom; Mary Carlson; Joanna Groden, both of Salt Lake City, Utah; Philip John Hedge, Knutsford, United Kingdom; Geoff Joslyn, Salt Lake City, Utah; Alexander Fred Markham, Crewe, United Kingdom; Yusuke Nakamura, Tokyo, Japan; Andrew Thliveris; Raymond White, both of Salt Lake City, Utah

[73] Assignees: The Johns Hopkins University, Baltimore, Md.; The University of Utah, Salt Lake City, Utah; Zeneca, United Kingdom; Cancer Institute, Tokyo, Japan

[21] Appl. No.: 08/726,870

[22] Filed: Oct. 4, 1996

Related U.S. Patent Documents

Reissue of:

[64] Patent No.: 5,352,775
Issued: Oct. 4, 1994
Appl. No.: 07/741,940
Filed: Aug. 8, 1991

[30] Foreign Application Priority Data

| | | | |
|---|---|---|---|
| Jan. 16, 1991 | [GB] | United Kingdom | 9100962 |
| Jan. 16, 1991 | [GB] | United Kingdom | 9100963 |
| Jan. 16, 1991 | [GB] | United Kingdom | 9100974 |
| Jan. 16, 1991 | [GB] | United Kingdom | 9100975 |

[51] Int. Cl.[7] ..... C12N 15/12; C07K 14/435; C12Q 01/68

[52] U.S. Cl. ..... 536/23.5; 536/24.31; 536/24.33; 536/23.1; 435/6; 935/6; 935/8; 935/9

[58] Field of Search ..... 536/23.5, 24.31, 536/23.1, 24.33; 935/6, 8, 9; 435/6

[56] References Cited

U.S. PATENT DOCUMENTS

| | | | |
|---|---|---|---|
| 5,098,823 | 3/1992 | Bodmer et al. | 435/6 |
| 5,137,806 | 8/1992 | LeMaistre et al. | 436/6 |

FOREIGN PATENT DOCUMENTS

89/01481 2/1989 WIPO .

OTHER PUBLICATIONS

Groden, et al., Cell, vol. 66, pp. 589–600, 1991.
Joslyn, et al., Cell, vol. 66, pp. 601–613, 1991.
Kinzler, et al., Science, vol. 253, pp. 661–665, 1991.
Nishisho et al., Science, vol. 253, pp. 665–669, 1991.
Orita, et al., Genomics, vol. 5, pp. 874–879, 1989.
Stanbridge, et al., Science, vol. 247, pp. 12–13, 1990.
Bodmer et al., 1987 Nature 328:614.
Fearen et al 1990 Science 247:49.
Baker et al. 1989 Science 244:217.

*Primary Examiner*—David L. Fitzgerald
*Attorney, Agent, or Firm*—Banner & Witcoff, Ltd.

[57] ABSTRACT

A human gene termed APC is disclosed. Methods and kits are provided for assessing mutations of the APC gene in hum tissues and body samples. APC mutations are found in familial adenomatous polyposis patients as wel as in sporadic colorectal cancer patents. APC is expressed in most normal tissue. These results suggest that APC is a tumor suppressor.

10 Claims, 40 Drawing Sheets

FIG. 2A

TB1 Amino Acid Sequence

VAPVVVGSGR APRHPAPAAM HPRRPDGFDG LGYRGGARDE QGFGGAFPAR SFSTGSDLGH 60

WVTTPPDIPG SRNLHWGEKS PPYGVPTTST PYEGPTEEPF SSGGGGSVQG QSSEQLNRFA 120

GFGIGLASLF TENVLAHPCI VLRRQCQVNY HAQHYHLTPF TVINIMYSFN KTQGPRALWK 180

GMGSTFIVQG VTLGAEGIIS EFTPLPREVL HKWSPKQIGE HLLLKSLTYV VAMPFYSASL 240

IETVQSEIIR DNTGILECVK EGIGRVIGMG VPHSKRLLPL LSLIFPTVLH GVLHYIISSV 300

IQKFVLLILK RKTYNSHLAE STSPVQSMLD AYFPELIANF AASLCSDVIL YPLETVLHRL 360

HIQGTRTIID NTDLGYEVLP INTQYEGMRD CINTIRQEEG VFGFYKGFGA VIIQYTLHAA 420

VLQITKIIYS TLLQ 434

FIG. 2B

TB2 Amino Acid Sequence

ELRRFDRFLH EKNCMTDLLA KLEAKTGVNR SFIALGVIGL VALYLVFGYG ASLLCNLIGF 60

GYPAYISIKA IESPNKEDDT QWLTYWVVYG VFSIAEFFSD IFLSWFPFYY ILKCGFLLWC 120

MAPSPSNGAE LLYKRIIRPF FLKHESQMDS VVKDLKDKAK ETADAITKEA KKATVNLLGE 180

EKKST 185

Amended Figure 3A

```
        10         20         30         40         50         60
MAAASYDQLL KQVEALKMEN SNLRQELEDN SNHLTKLETE ASNMKEVLKQ LQGSIEDEAM
        70         80         90        100        110        120
ASSGQIDLLE RLKELNLDSS NFPGVKLRSK MSLRSYGSRE GSVSSRSGEC SPVPMGSFPR
       130        140        150        160        170        180
RGFVNGSRES TGYLEELEKE RSLLLADLDK EEKEKDWYYA QLQNLTKRID SLPLTENFSL
       190        200        210        220        230        240
QTDMTRRQLE YEARQIRVAM EEQLGTCQDM EKRAQRRIAR IQQIEKDILR IRQLLQSQAT
       250        260        270        280        290        300
EAERSSQNKH ETGSHDAERQ NEGQGVGEIN MATSGNGQGS TTRMDHETAS VLSSSSTHSA
       310        320        330        340        350        360
PRRLTSHLGT KVEMVYSLLS MLGTHDKDDM SRTLLAMSSS QDSCISMRQS GCLPLLIQLL
       370        380        390        400        410        420
HGNDKDSVLL GNSRGSKEAR ARASAALHNI IHSQPDDKRG RREIRVLHLL EQIRAYCETC
       430        440        450        460        470        480
WEWQEAHEPG MDQDKNPMPA PVEHQICPAV CVLMKLSFDE EHRHAMNELG GLQAIAELLQ
       490        500        510        520        530        540
VDCEMYGLTN DHYSITLRRY AGMALTNLTF GDVANKATLC SMKGCMRALV AQLKSESEDL
       550        560        570        580        590        600
QQVIASVLRN LSWRADVNSK KTLREVGSVK ALMECALEVK KESTLKSVLS ALWNLSAHCT
       610        620        630        640        650        660
ENKADICAVD GALAFLVGTL TYRSQTNTLA IIESGGGILR NVSSLIATNE DHRQILRENN
       670        680        690        700        710        720
CLQTLLQHLK SHSLTIVSNA CGTLWNLSAR NPKDQEALWD MGAVSMLKNL IHSKHKMIAM
       730        740        750        760        770        780
GSAAALRNLM ANRPAKYKDA NIMSPGSSLP SLHVRKQKAL EAELDAQHLS ETFDNIDNLS
       790        800        810        820        830        840
PKASHRSKQR HKQSLYGDYV FDTNRHDDNR SDNFNTGNMT VLSPYLNTTV LPSSSSSRGS
       850        860        870        880        890        900
LDSSRSEKDR SLERERGIGL GNYHPATENP GTSSKRGLQI STTAAQIAKV MEEVSAIHTS
       910        920        930        940        950        960
QEDRSSGSTT ELHCVTDERN ALRRSSAAHT HSNTYNFTKS ENSNRTCSMP YAKLEYKRSS
       970        980        990       1000       1010       1020
NDSLNSVSSS DGYGKRGQMK PSIESYSEDD ESKFCSYGQY PADLAHKIHS ANHMDDNDGE
      1030       1040       1050       1060       1070       1080
LDTPINYSLK YSDEQLNSGR QSPSQNERWA RPKHIIEDEI KQSEQRQSRN QSTTYPVYTE
      1090       1100       1110       1120       1130       1140
STDDKHLKFQ PHFGQQECVS PYRSRGANGS ETNRVGSNHG INQNVSQSLC QEDDYEDDKP
      1150       1160       1170       1180       1190       1200
TNYSERYSEE EQHEEEERPT NYSIKYNEEK RHVDQPIDYS LKYATDIPSS QKQSFSFSKS
      1210       1220       1230       1240       1250       1260
SSGQSSKTEH MSSSSENTST PSSNAKRQNQ LHPSSAQSRS GQPQKAATCK VSSINQETIQ
      1270       1280       1290       1300       1310       1320
TYCVEDTPIC FSRCSSLSSL SSAEDEIGCN QTTQEADSAN TLQIAEIKEK IGTRSAEDPV
      1330       1340       1350       1360       1370       1380
        HP RTKSSRLQGS SLSSESARHK AVEFSSGAKS PSKSGAQTPK SPPEHYVQET
        90       1400       1410       1420       1430       1440
```

Amended *Figure 3B*

PLMFSRCTSV SSLDSFESRS IASSVQSEPC SGMVSGIISP SDLPDSPGQT MPPSRSKTPP
1450 1460 1470 1480 1490 1500
PPPQTAQTKR EVPKNKAPTA EKRESGPKQA AVNAAVQRVQ VLPDADTLLH FATESTPDGF
1510 1520 1530 1540 1550 1560
SCSSSLSALS LDEPFIQKDV ELRIMPPVQE NDNGNETESE QPKESNENQE KEAEKTIDSE
1570 1580 1590 1600 1610 1620
KDLLDDSDDD DIEILEECII SAMPTKSSRK AKKPAQTASK LPPPVARKPS QLPVYKLLPS
1630 1640 1650 1660 1670 1680
QNRLQPQKHV SFTPGDDMPR VYCVEGTPIN FSTATSLSDL TIESPPNELA AGEGVRGGAQ
1690 1700 1710 1720 1730 1740
SGEFEKRDTI PTEGRSTDEA QGGKTSSVTI PELDDNKAEE GDILAECINS AMPKGKSHKP
1750 1760 1770 1780 1790 1800
FRVKKIMDQV QQASASSSAP NKNQLDGKKK KPTSPVKPIP QNTEYRTRVR KNADSKNNLN
1810 1820 1830 1840 - 1850 1860
AERVFSDNKD SKKQNLKNNS KDFNDKLPNN EDRVRGSFAF DSPHHYTPIE GTPYCFSRND
1870 1880 1890 1900 1910 1920
SLSSLDFDDD DVDLSREKAE LRKAKENKES EAKVTSHTEL TSNQQSANKT QAIAKQPINR
1930 1940 1950 1960 1970 1980
GQPKPILQKQ STFPQSSKDI PDRGAATDEK LQNFAIENTP VCFSHNSSLS SLSDIDQENN
1990 2000 2010 2020 2030 2040
NKENEPIKET EPPDSQGEPS KPQASGYAPK SFHVEDTPVC FSRNSSLSSL SIDSEDDLLQ
2050 2060 2070 2080 2090 2100
ECISSAMPKK KKPSRLKGDN EKHSPRNMGG ILGEDLTLDL KDIQRPDSEH GLSPDSENFD
2110 2120 2130 2140 2150 2160
WKAIQEGANS IVSSLHQAAA AACLSRQASS DSDSILSLKS GISLGSPFHL TPDQEEKPFT
2170 2180 2190 2200 2210 2220
SNKGPRILKP GEKSTLETKK IESESKGIKG GKKVYKSLIT GKVRSNSEIS GQMKQPLQAN
2230 2240 2250 2260 2270 2280
MPSISRGRTM IHIPGVRNSS SSTSPVSKKG PPLKTPASKS PSEGQTATTS PRGAKPSVKS
2290 2300 2310 2320 2330 2340
ELSPVARQTS QIGGSSKAPS RSGSRDSTPS RPAQQPLSRP IQSPGRNSIS PGRNGISPPN
2350 2360 2370 2380 2390 2400
KLSQLPRTSS PSTASTKSSG SGKMSYTSPG RQMSQQNLTK QTGLSKNASS IPRSESASKG
2410 2420 2430 2440 2450 2460
LNQMNNGNGA NKKVELSRMS STKSSGSESD RSERPVLVRQ STFIKEAPSP TLRRKLEESA
2470 2480 2490 2500 2510 2520
SFESLSPSSR PASPTRSQAQ TPVLSPSLPD MSLSTHSSVQ AGGWRKLPPN LSPTIEYNDG
2530 2540 2550 2560 2570 2580
RPAKRHDIAR SHSESPSRLP INRSGTWKRE HSKHSSSLPR VSTWRRTGSS SSILSASSES
2590 2600 2610 2620 2630 2640
SEKAKSEDEK HVNSISGTKQ SKENQVSAKG TWRKIKENEF SPTNSTSQTV SSGATNGAES
2650 2660 2670 2680 2690 2700
KTLIYQMAPA VSKTEDVWVR IEDCPINNPR SGRSPTGNTP PVIDSVSEKA NPNIKDSKDN
2710 2720 2730 2740 2750 2760
QAKQNVGNGS VPMRTVGLEN RLNSFIQVDA PDQKGTEIKP GQNNPVPVSE TNESSIVERT
2770 2780 2790 2800 2810 2820
PFSSSSSSKH SSPSGTVAAR VTPFNYNPSP RKSSADSTSA RPSQIPTPVN NNTKKRDSKT

Amended *Figure 3C*

```
      2830        2840
DSTESSGTQS PKRHSGSYLV TSV*
```

FIG. 4A

```
APC      203  LGTCQDMEKRAQRRIARIQQIEKDILRIRQL  233
              |     :: || ||||||:|    |     |
RAL2     576  LTGAKGLQLRALRRIARIEQGGTAISPTSPL  606
```

FIG. 4B

```
APC      453  MKLSFDEEHRHAMNELGGLQAIAELLQVD  481
              :      |  :   ||:|||| :   : :
M3 MACHR 249  LYWRIYKETEKRTKELAGLQASGTEAETE  277
              ||  :  |  :  ||||||
MCC      220  LYPNLAEERSRWEKELAGLREENESLTAM  248
              :     ||: :   ||:||    | |
APC      453  MKLSFDEEHRHAMNELGGLQAIAELLQVD  481
```

FIG. 6A

```
                                    28                                                  55
GCA GTC GCC GCT CCA GTC TAT CCG GCA CTA GGA ACA GCC CCG GGN GGC GAG ACG
Ala Val Ala Ala Pro Val Tyr Pro Ala Leu Gly Thr Ala Pro Gly Gly Glu Thr
                                    82                                                  109
GTC CCC GCC ATG TCT GCG GCC ATG AGG GAG AGG TTC GAC CGG TTC CTG CAC GAG
Val Pro Ala MET Ser Ala Ala MET Arg Glu Arg Phe Asp Arg Phe Leu His Glu
                                    136                                                 163
AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn
                                    190                                                 217
AGG AGC TTC ATC GCT CTT GGT GTC ATC GGA CTG GTG GCC TTG TAC CTG GTG TTC
Arg Ser Phe Ile Ala Leu Gly Val Ile Gly Leu Val Ala Leu Tyr Leu Val Phe
                                    244                                                 271
GGT TAT GGA GCC TCT CTC CTC TGC AAC CTG ATA GGA TTT GGC TAC CCA GCC TAC
Gly Tyr Gly Ala Ser Leu Leu Cys Asn Leu Ile Gly Phe Gly Tyr Pro Ala Tyr
                                    298                                                 325
ATC TCA ATT AAA GCT ATA GAG AGT CCC AAC AAA GAA GAT GAT ACC CAG TGG CTG
Ile Ser Ile Lys Ala Ile Glu Ser Pro Asn Lys Glu Asp Asp Thr Gln Trp Leu
                                    352                                                 379
ACC TAC TGG GTA GTG TAT GGT GTG TTC AGC ATT GCT GAA TTC TTC TCT GAT ATC
Thr Tyr Trp Val Val Tyr Gly Val Phe Ser Ile Ala Glu Phe Phe Ser Asp Ile
                                    406                                                 433
TTC CTG TCA TGG TTC CCC TTC TAC TAC ATG CTG AAG TGT GGC TTC CTG TTG TGG
Phe Leu Ser Trp Phe Pro Phe Tyr Tyr MET Leu Lys Cys Gly Phe Leu Leu Trp
                                    460                                                 487
TGC ATG GCC CCG AGC CCT TCT AAT GGG GCT GAA CTG CTC TAC AAG CGC ATC ATC
Cys MET Ala Pro Ser Pro Ser Asn Gly Ala Glu Leu Leu Tyr Lys Arg Ile Ile
                                    514                                                 541
CGT CCT TTC TTC CTG AAG CAC GAG TCC CAG ATG GAC AGT GTG GTC AAG GAC CTT
Arg Pro Phe Phe Leu Lys His Glu Ser Gln MET Asp Ser Val Val Lys Asp Leu
```

FIG. 6B

```
                                    568                                     595
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                                    622
ACC GTG AAT TTA CTG GGT GAA GAA AAG AAG AGC ACC TAA ACC AGA
Thr Val Asn Leu Leu Gly Glu Glu Lys Lys Ser Thr
        640         650         660         670         680         690         700
 CTAAACCAGA CTGGATGGAA ACTTCCTGCC CTCTCTGTAC CTTCCTACTG GAGCTTGATG TTATATTAGG
        710         720         730         740         750         760         770
 GACTGTGGTA TAATTATTTT AATAATGTTG CCTTGGAAAC ATTTTTGAGA TATTAAAGAT TGGAATGTGT

        780         790         800         810         820         830         840
 TGTAAGTTTC TTTGCTTACT TTTACTGTCT ATATATATAG GGAGCACTTT AAACTTAATG CAGTGGGCAG
        850         860         870         880         890         900         910
 TGTCCACGTT TTTGGAAAAT GTATTTTGCC TCTGGGTAGG AAAAGATGTA TGTTGCTATC CTGCAGGAAA
        920         930         940         950         960         970         980
 TATAAACTTA AAATAAAATT ATATACCCCA CAGGCTGTGT ACTTTACTGG GCTCTCCCTG CACGSATTTT
        990        1000        1010        1020        1030        1040        1050
 CTCTGTAGTT ACATTTAGGR TAATCTTTAT GGTTCTACTT CCTRTAATGT ACAATTTTAT ATAATTCNGR
       1060        1070        1080        1090        1100        1110        1120
 AATGTTTTTA ATGTATTTGT GCACATGTAC ATATGGAAAT GTTACTGTCT GACTACANCA TGCATCATGC
       1130        1140        1150        1160        1170        1180        1190
 TCATGGGGAG GGAGCAGGGG AAGGTTGTAT GTGTCATTTA TAACTTCTGT ACAGTAAGAC CACCTGCCAA
       1200        1210        1220        1230        1240        1250        1260
 AAGCTGGAGG AACCATTGTG CTGGTGTGGT CTACTAAATA ATACTTTAGG AAATACGTGA TTAATATGCA
       1270        1280        1290        1300        1310        1320        1330
 AGTGAACAAA GTGAGAAATG AAATCGAATG GAGATTGGCC TGGTTGTTTC CGTAGTATAT GGCATATGAA
       1340        1350        1360        1370        1380        1390        1400
```

FIG. 6C

```
TACCAGGATA GCTTTATAAA GCAGTTAGTT AGTTAGTTAC TCACTCTAGT GATAAATCGG GAAATTTACA
      1410       1420       1430       1440       1450       1460       1470
CACACACACA CACACACACA CACACACACA CACACACACA CACACACACA GAGTACCCTG TAACTCTCAA
      1480       1490       1500       1510       1520       1530       1540
TTCCCTGAAA AACTAGTAAT ACTGTCTTAT CTGCTATAAA CTTTACATAT TTGTCTATTG TCAAGATGCT
      1550       1560       1570       1580       1590       1600       1610
ACANTGGAMN CCATTTCTGG TTTTATCTTC ANAGSGGAGA NACATGTTGA TTTAGTCTTC TTTCCCAATC
      1620       1630       1640       1650       1660       1670       1680
TTCTTTTTTA AMCCAGTTTN AGGMNCTTCT GRAGATTTGY CCACCTCTGA TTACATGTAT GTTCTYGTTT
      1690       1700       1710       1720       1730       1740       1750
GTATCATKAG CAACAACATG CTAATGRCGA CACCTAGCTC TRAGMGCAAT TCTGGGAGAN TGARAGGNWG
      1760       1770       1780       1790       1800       1810       1820
TATARAGTMN CCCATAATCT GCTTGGCAAT AGTTAAGTCA ATCTATCTTC AGTTTTTCTC TGGCCTTTAA
      1830       1840       1850       1860       1870       1880       1890
GGTCAAACAC AAGAGGCTTC CCTAGTTTAC AAGTCAGAGT CACTTGTAGT CCATTTAAAT GCCCTCATCC
      1900       1910       1920       1930       1940       1950       1960
GTATTCTTTG TGTTGATAAG CTGCACAKGA CTACATAGTA AGTACAGANC AGTAAAGTTA ANNCGGATGT
      1970       1980       1990       2000       2010       2020       2030
CTCCATTGAT CTGCCAANTC GNTATAGAGA GCAATTTGTC TGGACTAGAA AATCTGAGTT TTACACCATA
      2040       2050       2060       2070       2080       2090       2100
CTGTTAAGAG TCCTTTTGAA TTAAACTAGA CTAAAACAAG TGTATAACTA AACTAACAAG ATTAAATATC
      2110       2120       2130       2140       2150       2160       2170
CAGCCAGTAC AGTATTTTTT AAGGCAAATA AAGATGATTA GCTCACCTTG AGNTAACAAT CAGGTAAGAT

      2180       2190       2200       2210       2220       2230       2240
CATNACAATG TCTCATGATG TNAANAATAT TAAAGATATC AATACTAAGT GACAGTATCA CNNCTAATAT
```

FIG. 6D

```
      2250       2260       2270       2280       2290       2300       2310
AATATGGATC AGAGCATTTA TTTTGGGGAG GAAAACAGTG GTGATTACCG GCATTTTATT AAACTTAAAA
      2320       2330       2340       2350       2360       2370       2380
CTTTGTAGAA AGCAAACAAA ATTGTTCTTG GGAGAAAATC AACTTTTAGA TTAAAAAAAT TTTAAGTAWC
      2390       2400       2410       2420       2430       2440       2450
TAGGAGTATT TAAATCCTTT TCCCATAAAT AAAAGTACAG TTTTCTTGGT GGCAGAATGA AAATCAGCAA
      2460       2470       2480       2490       2500       2510       2520
CNTCTAGCAT ATAGACTATA TAATCAGATT GACAGCATAT AGAATATATT ATCAGACAAG ATGAGGAGGT
      2530       2540       2550       2560       2570       2580       2590
ACAAAAGTTA CTATTGCTCA TAATGACTTA CAGGCTAAAA NTAGNTNTAA AATACTATAT TAAATTCTGA
      2600       2610       2620       2630       2640       2650       2660
ATGCAATTTT TTTTTGTTCC CTTGAGACCA AAATTTAAGT TAACTGTTGC TGGCAGTCTA AGTGTAAATG
      2670       2680       2690       2700       2710       2720       2730
TTAACAGCAG GAGAAGTTAA GAATTGAGCA GTTCTGTTGC ATGATTTCCC AAATGAAATA CTGCCTTGGC
      2740       2750       2760       2770       2780       2790       2800
TAGAGTTTGA AAAACTAATT GAGCCTGTGC CTGGCTAGAA AACAAGCGTT TATTTGAATG TGAATAGTGT
      2810       2820       2830       2840       2850       2860       2870
TTCAAAGGTA TGTAGTTACA GAATTCCTAC CAAACAGCTT AAATTCTTCA AGAAAGAATT CCTGCAGCAG
      2880       2890       2900       2910       2920       2930       2940
TTATTCCCTT ACCTGAAGGC TTCAATCATT TGGATCAACA ACTGCTACTC TCGGGAAGAC TCCTCTACTC
      2950       2960       2970       2980       2990       3000       3010
ACAGCTGAAG AAAATGAGCA CACCCTTCAC ACTGTTATCA CCTATCCTGA AGATGTGATA CACTGAATGG
      3020       3030       3040       3050       3060       3070       3080
AAATAAATAG ATGTAAATAA AATTGAGWTC TCATTTAAAA AAAACCATGT GCCCAATGGG AAAATGACCT
      3090       3100       3110       3120       3130       3140       3150
CATGTTGTGG TTTAAACAGC AACTGCACCC ACTAGCACAG CCCATTGAGC TANCCTATAT ATACATCTCT
      3160
GTCAGTGCCC CTC
```

Amended *Figure 7A*

```
23  ATGGCTGCAGCTTCATATGATCAGTTGTTAAAGCAAGTTGAGGCACTGAAGATGGAGAAC   82

 1  M  A  A  A  S  Y  D  Q  L  L  K  Q  V  E  A  L  K  M  E  N    20

83  TCAAATCTTCGACAAGAGCTAGAAGATAATTCCAATCATCTTACAAAACTGGAAACTGAG  142

21  S  N  L  R  Q  E  L  E  D  N  S  N  H  L  T  K  L  E  T  E    40

143 GCATCTAATATGAAGGAAGTACTTAAACAACTACAAGGAAGTATTGAAGATGAAGCTATG  202

41  A  S  N  M  K  E  V  L  K  Q  L  Q  G  S  I  E  D  E  A  M    60

203 GCTTCTTCTGGACAGATTGATTTATTAGAGCGTCTTAAAGAGCTTAACTTAGATAGCAGT  262

61  A  S  S  G  Q  I  D  L  L  E  R  L  K  E  L  N  L  D  S  S    80

263 AATTTCCCTGGAGTAAAACTGCGGTCAAAAATGTCCCTCCGTTCTTATGGAAGCCGGGAA  322

81  N  F  P  G  V  K  L  R  S  K  M  S  L  R  S  Y  G  S  R  E   100

323 GGATCTGTATCAAGCCGTTCTGGAGAGTGCAGTCCTGTTCCTATGGGTTCATTTCCAAGA  382

101 G  S  V  S  S  R  S  G  E  C  S  P  V  P  M  G  S  F  P  R   120

383 AGAGGGTTTGTAAATGGAAGCAGAGAAAGTACTGGATATTTAGAAGAACTTGAGAAAGAG  442
```

Amended *Figure 7B*

121 R G F V N G S R E S T G Y L E E L E K E 140

443 AGGTCATTGCTTCTTGCTGATCTTGACAAAGAAGAAAAGGAAAAAGACTGGTATTACGCT 502

141 R S L L L A D L D K E E K E K D W Y Y A 160

503 CAACTTCAGAATCTCACTAAAAGAATAGATAGTCTTCCTTTAACTGAAAATTTTTCCTTA 562

161 Q L Q N L T K R I D S L P L T E N F S L 180

563 CAAACAGATATGACCAGAAGGCAATTGGAATATGAAGCAAGGCAAATCAGAGTTGCGATG 622

181 Q T D M T R R Q L E Y E A R Q I R V A M 200

623 GAAGAACAACTAGGTACCTGCCAGGATATGGAAAAACGAGCACAGCGAAGAATAGCCAGA 682

201 E E Q L G T C Q D M E K R A Q R R I A R 220

683 ATTCAGCAAATCGAAAAGGACATACTTCGTATACGACAGCTTTTACAGTCCCAAGCAACA 742

221 I Q Q I E K D I L R I R Q L L Q S Q A T 240

743 GAAGCAGAGAGGTCATCTCAGAACAAGCATGAAACCGGCTCACATGATGCTGAGCGGCAG 802

241 E A E R S S Q N K H E T G S H D A E R Q 260

Amended *Figure 7C*

803 AATGAAGGTCAAGGAGTGGGAGAAATCAACATGGCAACTTCTGGTAATGGTCAGGGTTCA 862

261 N E G Q G V G E I N M A T S G N G Q G S 280

863 ACTACACGAATGGACCATGAAACAGCCAGTGTTTTGAGTTCTAGTAGCACACACTCTGCA 922

281 T T R M D H E T A S V L S S S S T H S A 300

923 CCTCGAAGGCTGACAAGTCATCTGGGAACCAAGgtggaaatggtgtattcattgttgtca 982

301 p r r l t s h l g t k v e m v y s l l s 320

983 atgcttggtactcatgataaggatgatatgtcgcgaactttgctagctatgtctagctcc 1042

321 m l g t h d k d d m s r t l l a m s s s 340

1043 caagacagctgtatatccatgcgacagtctggatgtcttcctctcctcatccagctttta 1102

341 q d s c i s m r q s g c l p l l i q l l 360

1103 catggcaatgacaaagactctgtattgttgggaaattcccggggcagtaaagaggctcgg 1162

361 h g n d k d s v l l g n s r g s k e a r 380

1163 gccagggccagtgcagcactccacaacatcattcactcacagcctgatgacaagagaggc 1222

Amended *Figure 7D*

```
381  a  r  a  s  a  a  l  h  n  i  i  h  s  q  p  d  d  k  r  g    400

1223 aggcgtgaaatccgagtccttcatcttttggaacagATACGCGCTTACTGTGAAACCTGT   1282

401  r  r  e  i  r  v  l  h  l  l  e  q  I  R  A  Y  C  E  T  C    420

1283 TGGGAGTGGCAGGAAGCTCATGAACCAGGCATGGACCAGGACAAAAATCCAATGCCAGCT   1342

421  W  E  W  Q  E  A  H  E  P  G  M  D  Q  D  K  N  P  M  P  A    440

1343 CCTGTTGAACATCAGATCTGTCCTGCTGTGTGTGTTCTAATGAAACTTTCATTTGATGAA   1402

441  P  V  E  H  Q  I  C  P  A  V  C  V  L  M  K  L  S  F  D  E    460

1403 GAGCATAGACATGCAATGAATGAACTAGGGGGACTACAGGCCATTGCAGAATTATTGCAA   1462

461  E  H  R  H  A  M  N  E  L  G  G  L  Q  A  I  A  E  L  L  Q    480

1463 GTGGACTGTGAAATGTACGGGCTTACTAATGACCACTACAGTATTACACTAAGACGATAT   1522

481  V  D  C  E  M  Y  G  L  T  N  D  H  Y  S  I  T  L  R  R  Y    500

1523 GCTGGAATGGCTTTGACAAACTTGACTTTTGGAGATGTAGCCAACAAGGCTACGCTATGC   1582

501  A  G  M  A  L  T  N  L  T  F  G  D  V  A  N  K  A  T  L  C    520
```

Amended *Figure 7E*

1583 TCTATGAAAGGCTGCATGAGAGCACTTGTGGCCCAACTAAAATCTGAAAGTGAAGACTTA 1642

521 S M K G C M R A L V A Q L K S E S E D L 540

1643 CAGCAGGTTATTGCAAGTGTTTTGAGGAATTTGTCTTGGCGAGCAGATGTAAATAGTAAA 1702

541 Q Q V I A S V L R N L S W R A D V N S K 560

1703 AAGACGTTGCGAGAAGTTGGAAGTGTGAAAGCATTGATGGAATGTGCTTTAGAAGTTAAA 1762

561 K T L R E V G S V K A L M E C A L E V K 580

1763 AAGGAATCAACCCTCAAAAGCGTATTGAGTGCCTTATGGAATTTGTCAGCACATTGCACT 1822

581 K E S T L K S V L S A L W N L S A H C T 600

1823 GAGAATAAAGCTGATATATGTGCTGTAGATGGTGCACTTGCATTTTTGGTTGGCACTCTT 1882

601 E N K A D I C A V D G A L A F L V G T L 620

1883 ACTTACCGGAGCCAGACAAACACTTTAGCCATTATTGAAAGTGGAGGTGGGATATTACGG 1942

621 T Y R S Q T N T L A I I E S G G G I L R 640

Amended *Figure 7F*

1943 AATGTGTCCAGCTTGATAGCTACAAATGAGGACCACAGGCAAATCCTAAGAGAGAACAAC 2002

641 N V S S L I A T N E D H R Q I L R E N N 660

2003 TGTCTACAAACTTTATTACAACACTTAAAATCTCATAGTTTGACAATAGTCAGTAATGCA 2062

661 C L Q T L L Q H L K S H S L T I V S N A 680

2063 TGTGGAACTTTGTGGAATCTCTCAGCAAGAAATCCTAAAGACCAGGAAGCATTATGGGAC 2122

681 C G T L W N L S A R N P K D Q E A L W D 700

2123 ATGGGGGCAGTTAGCATGCTCAAGAACCTCATTCATTCAAAGCACAAAATGATTGCTATG 2182

701 M G A V S M L K N L I H S K H K M I A M 720

2183 GGAAGTGCTGCAGCTTTAAGGAATCTCATGGCAAATAGGCCTGCGAAGTACAAGGATGCC 2242

721 G S A A A L R N L M A N R P A K Y K D A 740

2243 AATATTATGTCTCCTGGCTCAAGCTTGCCATCTCTTCATGTTAGGAAACAAAAAGCCCTA 2302

741 N I M S P G S S L P S L H V R K Q K A L 760

2303 GAAGCAGAATTAGATGCTCAGCACTTATCAGAAACTTTTGACAATATAGACAATTTAAGT 2362

Amended *Figure 7G*

761 E A E L D A Q H L S E T F D N I D N L S 780

2363 CCCAAGGCATCTCATCGTAGTAAGCAGAGACACAAGCAAAGTCTCTATGGTGATTATGTT 2422

781 P K A S H R S K Q R H K Q S L Y G D Y V 800

2423 TTTGACACCAATCGACATGATGATAATAGGTCAGACAATTTTAATACTGGCAACATGACT 2482

801 F D T N R H D D N R S D N F N T G N M T 820

2483 GTCCTTTCACCATATTTGAATACTACAGTGTTACCCAGCTCCTCTTCATCAAGAGGAAGC 2542

821 V L S P Y L N T T V L P S S S S S R G S 840

2543 TTAGATAGTTCTCGTTCTGAAAAAGATAGAAGTTTGGAGAGAGAACGCGGAATTGGTCTA 2602

841 L D S S R S E K D R S L E R E R G I G L 860

2603 GGCAACTACCATCCAGCAACAGAAAATCCAGGAACTTCTTCAAAGCGAGGTTTGCAGATC 2662

861 G N Y H P A T E N P G T S S K R G L Q I 880

2663 TCCACCACTGCAGCCCAGATTGCCAAAGTCATGGAAGAAGTGTCAGCCATTCATACCTCT 2722

881 S T T A A Q I A K V M E E V S A I H T S 900

Amended *Figure 7H*

2723 CAGGAAGACAGAAGTTCTGGGTCTACCACTGAATTACATTGTGTGACAGATGAGAGAAAT 2782

901 Q E D R S S G S T T E L H C V T D E R N 920

2783 GCACTTAGAAGAAGCTCTGCTGCCCATACACATTCAAACACTTACAATTTCACTAAGTCG 2842

921 A L R R S S A A H T H S N T Y N F T K S 940

2843 GAAAATTCAAATAGGACATGTTCTATGCCTTATGCCAAATTAGAATACAAGAGATCTTCA 2902

941 E N S N R T C S M P Y A K L E Y K R S S 960

2903 AATGATAGTTTAAATAGTGTCAGTAGTAGTGATGGTTATGGTAAAAGAGGTCAAATGAAA 2962

961 N D S L N S V S S S D G Y G K R G Q M K 980

2963 CCCTCGATTGAATCCTATTCTGAAGATGATGAAAGTAAGTTTTGCAGTTATGGTCAATAC 3022

981 P S I E S Y S E D D E S K F C S Y G Q Y 1000

3023 CCAGCCGACCTAGCCCATAAAATACATAGTGCAAATCATATGGATGATAATGATGGAGAA 3082

1001 P A D L A H K I H S A N H M D D N D G E 1020

3083 CTAGATACACCAATAAATTATAGTCTTAAATATTCAGATGAGCAGTTGAACTCTGGAAGG 3142

Amended *Figure 7I*

1021 L D T P I N Y S L K Y S D E Q L N S G R 1040

3143 CAAAGTCCTTCACAGAATGAAAGATGGGCAAGACCCAAACACATAATAGAAGATGAAATA 3202

1041 Q S P S Q N E R W A R P K H I I E D E I 1060

3203 AAACAAAGTGAGCAAAGACAATCAAGGAATCAAAGTACAACTTATCCTGTTTATACTGAG 3262

1061 K Q S E Q R Q S R N Q S T T Y P V Y T E 1080

3263 AGCACTGATGATAAACACCTCAAGTTCCAACCACATTTTGGACAGCAGGAATGTGTTTCT 3322

1081 S T D D K H L K F Q P H F G Q Q E C V S 1100

3323 CCATACAGGTCACGGGGAGCCAATGGTTCAGAAACAAATCGAGTGGGTTCTAATCATGGA 3382

1101 P Y R S R G A N G S E T N R V G S N H G 1120

3383 ATTAATCAAAATGTAAGCCAGTCTTTGTGTCAAGAAGATGACTATGAAGATGATAAGCCT 3442

1121 I N Q N V S Q S L C Q E D D Y E D D K P 1140

3443 ACCAATTATAGTGAACGTTACTCTGAAGAAGAACAGCATGAAGAAGAAGAGAGACCAACA 3502

1141 T N Y S E R Y S E E E Q H E E E E R P T 1160

Amended *Figure 7J*

3503 AATTATAGCATAAAATATAATGAAGAGAAACGTCATGTGGATCAGCCTATTGATTATAGT 3562

1161 N Y S I K Y N E E K R H V D Q P I D Y S 1180

3563 TTAAAATATGCCACAGATATTCCTTCATCACAGAAACAGTCATTTTCATTCTCAAAGAGT 3622

1181 L K Y A T D I P S S Q K Q S F S F S K S 1200

3623 TCATCTGGACAAAGCAGTAAAACCGAACATATGTCTTCAAGCAGTGAGAATACGTCCACA 3682

1201 S S G Q S S K T E H M S S S S E N T S T 1220

3683 CCTTCATCTAATGCCAAGAGGCAGAATCAGCTCCATCCAAGTTCTGCACAGAGTAGAAGT 3742

1221 P S S N A K R Q N Q L H P S S A Q S R S 1240

3743 GGTCAGCCTCAAAAGGCTGCCACTTGCAAAGTTTCTTCTATTAACCAAGAAACAATACAG 3802

1241 G Q P Q K A A T C K V S S I N Q E T I Q 1260

3803 ACTTATTGTGTAGAAGATACTCCAATATGTTTTTCAAGATGTAGTTCATTATCATCTTTG 3862

1261 T Y C V E D T P I C F S R C S S L S S L 1280

3863 TCATCAGCTGAAGATGAAATAGGATGTAATCAGACGACACAGGAAGCAGATTCTGCTAAT 3922

Amended *Figure 7K*

1281 S S A E D E I G C N Q T T Q E A D S A N 1300

3923 ACCCTGCAAATAGCAGAAATAAAAGAAAAGATTGGAACTAGGTCAGCTGAAGATCCTGTG 3982

1301 T L Q I A E I K E K I G T R S A E D P V 1320

3983 AGCGAAGTTCCAGCAGTGTCACAGCACCCTAGAACCAAATCCAGCAGACTGCAGGGTTCT 4042

1321 S E V P A V S Q H P R T K S S R L Q G S 1340

4043 AGTTTATCTTCAGAATCAGCCAGGCACAAAGCTGTTGAATTTTCTTCAGGAGCGAAATCT 4102

1341 S L S S E S A R H K A V E F S S G A K S 1360

4103 CCCTCCAAAAGTGGTGCTCAGACACCCAAAAGTCCACCTGAACACTATGTTCAGGAGACC 4162

1361 P S K S G A Q T P K S P P E H Y V Q E T 1380

4163 CCACTCATGTTTAGCAGATGTACTTCTGTCAGTTCACTTGATAGTTTTGAGAGTCGTTCG 4222

1381 P L M F S R C T S V S S L D S F E S R S 1400

4223 ATTGCCAGCTCCGTTCAGAGTGAACCATGCAGTGGAATGGTAAGTGGCATTATAAGCCCC 4282

1401 I A S S V Q S E P C S G M V S G I I S P 1420

Amended *Figure 7L*

4283 AGTGATCTTCCAGATAGCCCTGGACAAACCATGCCACCAAGCAGAAGTAAAACACCTCCA 4342

1421 S D L P D S P G Q T M P P S R S K T P P 1440

4343 CCACCTCCTCAAACAGCTCAAACCAAGCGAGAAGTACCTAAAAATAAAGCACCTACTGCT 4402

1441 P P P Q T A Q T K R E V P K N K A P T A 1460

4403 GAAAAGAGAGAGAGTGGACCTAAGCAAGCTGCAGTAAATGCTGCAGTTCAGAGGGTCCAG 4462

1461 E K R E S G P K Q A A V N A A V Q R V Q 1480

4463 GTTCTTCCAGATGCTGATACTTTATTACATTTTGCCACGGAAAGTACTCCAGATGGATTT 4522

1481 V L P D A D T L L H F A T E S T P D G F 1500

4523 TCTTGTTCATCCAGCCTGAGTGCTCTGAGCCTCGATGAGCCATTTATACAGAAAGATGTG 4582

1501 S C S S S L S A L S L D E P F I Q K D V 1520

4583 GAATTAAGAATAATGCCTCCAGTTCAGGAAAATGACAATGGGAATGAAACAGAATCAGAG 4642

1521 E L R I M P P V Q E N D N G N E T E S E 1540

4643 CAGCCTAAAGAATCAAATGAAAACCAAGAGAAAGAGGCAGAAAAAACTATTGATTCTGAA 4702

Amended *Figure 7M*

1541 Q P K E S N E N Q E K E A E K T I D S E 1560

4703 AAGGACCTATTAGATGATTCAGATGATGATGATATTGAAATACTAGAAGAATGTATTATT 4762

1561 K D L L D D S D D D D I E I L E E C I I 1580

4763 TCTGCCATGCCAACAAAGTCATCACGTAAAGCAAAAAAGCCAGCCCAGACTGCTTCAAAA 4822

1581 S A M P T K S S R K A K K P A Q T A S K 1600

4823 TTACCTCCACCTGTGGCAAGGAAACCAAGTCAGCTGCCTGTGTACAAACTTCTACCATCA 4882

1601 L P P P V A R K P S Q L P V Y K L L P S 1620

4883 CAAAACAGGTTGCAACCCCAAAAGCATGTTAGTTTTACACCGGGGGATGATATGCCACGG 4942

1621 Q N R L Q P Q K H V S F T P G D D M P R 1640

4943 GTGTATTGTGTTGAAGGGACACCTATAAACTTTTCCACAGCTACATCTCTAAGTGATCTA 5002

1641 V Y C V E G T P I N F S T A T S L S D L 1660

5003 ACAATCGAATCCCCTCCAAATGAGTTAGCTGCTGGAGAAGGAGTTAGAGGAGGAGCACAG 5062

1661 T I E S P P N E L A A G E G V R G G A Q 1680

Amended *Figure 7N*

5063 TCAGGTGAATTTGAAAAACGAGATACCATTCCTACAGAAGGCAGAAGTACAGATGAGGCT 5122

1681 S G E F E K R D T I P T E G R S T D E A 1700

5123 CAAGGAGGAAAAACCTCATCTGTAACCATACCTGAATTGGATGACAATAAAGCAGAGGAA 5182

1701 Q G G K T S S V T I P E L D D N K A E E 1720

5183 GGTGATATTCTTGCAGAATGCATTAATTCTGCTATGCCCAAAGGGAAAAGTCACAAGCCT 5242

1721 G D I L A E C I N S A M P K G K S H K P 1740

5243 TTCCGTGTGAAAAAGATAATGGACCAGGTCCAGCAAGCATCTGCGTCGTCTTCTGCACCC 5302

1741 F R V K K I M D Q V Q Q A S A S S S A P 1760

5303 AACAAAAATCAGTTAGATGGTAAGAAAAAGAAACCAACTTCACCAGTAAAACCTATACCA 5362

1761 N K N Q L D G K K K K P T S P V K P I P 1780

5363 CAAAATACTGAATATAGGACACGTGTAAGAAAAAATGCAGACTCAAAAAATAATTTAAAT 5422

1781 Q N T E Y R T R V R K N A D S K N N L N 1800

5423 GCTGAGAGAGTTTTCTCAGACAACAAAGATTCAAAGAAACAGAATTTGAAAAATAATTCC 5482

Amended *Figure 7O*

1801 A E R V F S D N K D S K K Q N L K N N S 1820

5483 AAGGACTTCAATGATAAGCTCCCAAATAATGAAGATAGAGTCAGAGGAAGTTTTGCTTTT 5542

1821 K D F N D K L P N N E D R V R G S F A F 1840

5543 GATTCACCTCATCATTACACGCCTATTGAAGGAACTCCTTACTGTTTTTCACGAAATGAT 5602

1841 D S P H H Y T P I E G T P Y C F S R N D 1860

5603 TCTTTGAGTTCTCTAGATTTTGATGATGATGATGTTGACCTTTCCAGGGAAAAGGCTGAA 5662

1861 S L S S L D F D D D D V D L S R E K A E 1880

5663 TTAAGAAAGGCAAAAGAAAATAAGGAATCAGAGGCTAAAGTTACCAGCCACACAGAACTA 5722

1881 L R K A K E N K E S E A K V T S H T E L 1900

5723 ACCTCCAACCAACAATCAGCTAATAAGACACAAGCTATTGCAAAGCAGCCAATAAATCGA 5782

1901 T S N Q Q S A N K T Q A I A K Q P I N R 1920

5783 GGTCAGCCTAAACCCATACTTCAGAAACAATCCACTTTTCCCCAGTCATCCAAAGACATA 5842

1921 G Q P K P I L Q K Q S T F P Q S S K D I 1940

Amended *Figure 7P*

5843 CCAGACAGAGGGGCAGCAACTGATGAAAAGTTACAGAATTTTGCTATTGAAAATACTCCA 5902

1941 P D R G A A T D E K L Q N F A I E N T P 1960

5903 GTTTGCTTTTCTCATAATTCCTCTCTGAGTTCTCTCAGTGACATTGACCAAGAAAACAAC 5962

1961 V C F S H N S S L S S L S D I D Q E N N 1980

5963 AATAAAGAAAATGAACCTATCAAAGAGACTGAGCCCCCTGACTCACAGGGAGAACCAAGT 6022

1981 N K E N E P I K E T E P P D S Q G E P S 2000

6023 AAACCTCAAGCATCAGGCTATGCTCCTAAATCATTTCATGTTGAAGATACCCCAGTTTGT 6082

2001 K P Q A S G Y A P K S F H V E D T P V C 2020

6083 TTCTCAAGAAACAGTTCTCTCAGTTCTCTTAGTATTGACTCTGAAGATGACCTGTTGCAG 6142

2021 F S R N S S L S S L S I D S E D D L L Q 2040

6143 GAATGTATAAGCTCCGCAATGCCAAAAAAGAAAAAGCCTTCAAGACTCAAGGGTGATAAT 6202

2041 E C I S S A M P K K K K P S R L K G D N 2060

6203 GAAAAACATAGTCCCAGAAATATGGGTGGCATATTAGGTGAAGATCTGACACTTGATTTG 6262

Amended *Figure 7Q*

2061 E K H S P R N M G G I L G E D L T L D L 2080

6263 AAAGATATACAGAGACCAGATTCAGAACATGGTCTATCCCCTGATTCAGAAAATTTTGAT 6322

2081 K D I Q R P D S E H G L S P D S E N F D 2100

6323 TGGAAAGCTATTCAGGAAGGTGCAAATTCCATAGTAAGTAGTTTACATCAAGCTGCTGCT 6382

2101 W K A I Q E G A N S I V S S L H Q A A A 2120

6383 GCTGCATGTTTATCTAGACAAGCTTCGTCTGATTCAGATTCCATCCTTTCCCTGAAATCA 6442

2121 A A C L S R Q A S S D S D S I L S L K S 2140

6443 GGAATCTCTCTGGGATCACCATTTCATCTTACACCTGATCAAGAAGAAAAACCCTTTACA 6502

2141 G I S L G S P F H L T P D Q E E K P F T 2160

6503 AGTAATAAAGGCCCACGAATTCTAAAACCAGGGGAGAAAAGTACATTGGAAACTAAAAAG 6562

2161 S N K G P R I L K P G E K S T L E T K K 2180

6563 ATAGAATCTGAAAGTAAAGGAATCAAAGGAGGAAAAAAAGTTTATAAAAGTTTGATTACT 6622

2181 I E S E S K G I K G G K K V Y K S L I T 2200

Amended *Figure 7R*

6623 GGAAAAGTTCGATCTAATTCAGAAATTTCAGGCCAAATGAAACAGCCCCTTCAAGCAAAC 6682

2201 G K V R S N S E I S G Q M K Q P L Q A N 2220

6683 ATGCCTTCAATCTCTCGAGGCAGGACAATGATTCATATTCCAGGAGTTCGAAATAGCTCC 6742

2221 M P S I S R G R T M I H I P G V R N S S 2240

6743 TCAAGTACAAGTCCTGTTTCTAAAAAAGGCCCACCCCTTAAGACTCCAGCCTCCAAAAGC 6802

2241 S S T S P V S K K G P P L K T P A S K S 2260

6803 CCTAGTGAAGGTCAAACAGCCACCACTTCTCCTAGAGGAGCCAAGCCATCTGTGAAATCA 6862

2261 P S E G Q T A T T S P R G A K P S V K S 2280

6863 GAATTAAGCCCTGTTGCCAGGCAGACATCCCAAATAGGTGGGTCAAGTAAAGCACCTTCT 6922

2281 E L S P V A R Q T S Q I G G S S K A P S 2300

6923 AGATCAGGATCTAGAGATTCGACCCCTTCAAGACCTGCCCAGCAACCATTAAGTAGACCT 6982

2301 R S G S R D S T P S R P A Q Q P L S R P 2320

6983 ATACAGTCTCCTGGCCGAAACTCAATTTCCCCTGGTAGAAATGGAATAAGTCCTCCTAAC 7042

Amended *Figure 7S*

2321 I Q S P G R N S I S P G R N G I S P P N 2340

7043 AAATTATCTCAACTTCCAAGGACATCATCCCCTAGTACTGCTTCAACTAAGTCCTCAGGT 7102

2341 K L S Q L P R T S S P S T A S T K S S G 2360

7103 TCTGGAAAAATGTCATATACATCTCCAGGTAGACAGATGAGCCAACAGAACCTTACCAAA 7162

2361 S G K M S Y T S P G R Q M S Q Q N L T K 2380

7163 CAAACAGGTTTATCCAAGAATGCCAGTAGTATTCCAAGAAGTGAGTCTGCCTCCAAAGGA 7222

2381 Q T G L S K N A S S I P R S E S A S K G 2400

7223 CTAAATCAGATGAATAATGGTAATGGAGCCAATAAAAAGGTAGAACTTTCTAGAATGTCT 7282

2401 L N Q M N N G N G A N K K V E L S R M S 2420

7283 TCAACTAAATCAAGTGGAAGTGAATCTGATAGATCAGAAAGACCTGTATTAGTACGCCAG 7342

2421 S T K S S G S E S D R S E R P V L V R Q 2440

7343 TCAACTTTCATCAAAGAAGCTCCAAGCCCAACCTTAAGAAGAAAATTGGAGGAATCTGCT 7402

2441 S T F I K E A P S P T L R R K L E E S A 2460

Amended *Figure 7T*

7403 TCATTTGAATCTCTTTCTCCATCATCTAGACCAGCTTCTCCCACTAGGTCCCAGGCACAA 7462

2461 S F E S L S P S S R P A S P T R S Q A Q 2480

7463 ACTCCAGTTTTAAGTCCTTCCCTTCCTGATATGTCTCTATCCACACATTCGTCTGTTCAG 7522

2481 T P V L S P S L P D M S L S T H S S V Q 2500

7523 GCTGGTGGATGGCGAAAACTCCCACCTAATCTCAGTCCCACTATAGAGTATAATGATGGA 7582

2501 A G G W R K L P P N L S P T I E Y N D G 2520

7583 AGACCAGCAAAGCGCCATGATATTGCACGGTCTCATTCTGAAAGTCCTTCTAGACTTCCA 7642

2521 R P A K R H D I A R S H S E S P S R L P 2540

7643 ATCAATAGGTCAGGAACCTGGAAACGTGAGCACAGCAAACATTCATCATCCCTTCCTCGA 7702

2541 I N R S G T W K R E H S K H S S S L P R 2560

7703 GTAAGCACTTGGAGAAGAACTGGAAGTTCATCTTCAATTCTTTCTGCTTCATCAGAATCC 7762

2561 V S T W R R T G S S S S I L S A S S E S 2580

7763 AGTGAAAAAGCAAAAAGTGAGGATGAAAAACATGTGAACTCTATTTCAGGAACCAAACAA 7822

Amended *Figure 7U*

2581 S E K A K S E D E K H V N S I S G T K Q 2600

7823 AGTAAAGAAAACCAAGTATCCGCAAAAGGAACATGGAGAAAAATAAAAGAAAATGAATTT 7882

2601 S K E N Q V S A K G T W R K I K E N E F 2620

7883 TCTCCCACAAATAGTACTTCTCAGACCGTTTCCTCAGGTGCTACAAATGGTGCTGAATCA 7942

2621 S P T N S T S Q T V S S G A T N G A E S 2640

7943 AAGACTCTAATTTATCAAATGGCACCTGCTGTTTCTAAAACAGAGGATGTTTGGGTGAGA 8002

2641 K T L I Y Q M A P A V S K T E D V W V R 2660

8003 ATTGAGGACTGTCCCATTAACAATCCTAGATCTGGAAGATCTCCCACAGGTAATACTCCC 8062

2661 I E D C P I N N P R S G R S P T G N T P 2680

8063 CCGGTGATTGACAGTGTTTCAGAAAAGGCAAATCCAAACATTAAAGATTCAAAAGATAAT 8122

2681 P V I D S V S E K A N P N I K D S K D N 2700

8123 CAGGCAAAACAAAATGTGGGTAATGGCAGTGTTCCCATGCGTACCGTGGGTTTGGAAAAT 8182

2701 Q A K Q N V G N G S V P M R T V G L E N 2720

Amended *Figure 7V*

8183 CGCCTGAACTCCTTTATTCAGGTGGATGCCCCTGACCAAAAAGGAACTGAGATAAAACCA 8242

2721 R L N S F I Q V D A P D Q K G T E I K P 2740

8243 GGACAAAATAATCCTGTCCCTGTATCAGAGACTAATGAAAGTTCTATAGTGGAACGTACC 8302

2741 G Q N N P V P V S E T N E S S I V E R T 2760

8303 CCATTCAGTTCTAGCAGCTCAAGCAAACACAGTTCACCTAGTGGGACTGTTGCTGCCAGA 8362

2761 P F S S S S S S K H S S P S G T V A A R 2780

8363 GTGACTCCTTTTAATTACAACCCAAGCCCTAGGAAAAGCAGCGCAGATAGCACTTCAGCT 8422

2781 V T P F N Y N P S P R K S S A D S T S A 2800

8423 CGGCCATCTCAGATCCCAACTCCAGTGAATAACAACACAAAGAAGCGAGATTCCAAAACT 8482

2801 R P S Q I P T P V N N N T K K R D S K T 2820

8483 GACAGCACAGAATCCAGTGGAACCCAAAGTCCTAAGCGCCATTCTGGGTCTTACCTTGTG 8542

2821 D S T E S S G T Q S P K R H S G S Y L V 2840

8543 ACATCTGTTTAA 8554

Amended *Figure 7W*

2841 T S V * 2844

APC GENE AND NUCLEIC ACID PROBES DERIVED THEREFROM

Matter enclosed in heavy brackets [ ] appears in the original patent but forms no part of this reissue specification; matter printed in italics indicates the additions made by reissue.

The U.S. Government has a paid-up license in this invention and the right in limited circumstances to require the patent owner to license others on reasonable terms as provided for by the terms of grants awarded by the National Institutes of Health.

TECHNICAL AREA OF THE INVENTION

The invention relates to the area of cancer diagnostics and therapeutics. More particularly, the invention relates to detection of the germline and somatie alterations of wild-type APC genes. In addition, it relates to therapeutic intervention to restore the function of APC (adnomatous polyposis coli) gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the eases of retinoblastoma and colorectal tumors. The implicated suppressor genes in those tumors, RB (retinoblastoma), p53 (protein having a molecular weight of 53 kDa), Dcc (deleted in colorectal cancer) and MCC (mutated in colorectal cancer) were found to be deleted or altered in many eases of the tumors studied. (Hansen and Cavenee, Cancer Research, Vol.. 47, pp. 5518–5527 (1987): Baker et al., Science, Vol.. 244, p. 217 (1989); Fearon et al., Science, Vol. 247, p. 49 (1990); Kinzler et al. Science Vol. 251. p. 1366 (1991).)

In order to fully understand the pathogenesis of tumors, it will be necessary to identify the other suppressor genes that play a role in the tumorigenesis process. Prominent among these is the one(s) presumptively located at 5q21. Cytogenetie (Herrera et al., Am J. Med. Genet., Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmoid tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research. Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in both sporadic and familial tumors.

Although the MCC gene has been identified on 5q21 as a candidate suppressor gene, it does not appear to be altered in F AP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lost said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object or the invention to provide a preparation of the human APC protein.

It is another object of the invention to provide a method of screening for genetic predisposition to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products frown the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provided for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene coding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in [FIG. 3 or 7] *FIGS. 3A–3C or 7A–7W* (*SEQ ID NOS: 7 and 2*).

In yet another embodiment of the invention a method is provided for screening for genetic predisposition to cancer, including familial adenomatous polyposis (FAP) and Gardner's Syndrome (GS), in a human. The method comprises: detecting among kindred persons the presence of a DNA polymorphism which is linked to a mutant APC allele in an individual having a genetic predisposition to cancer, said kindred being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenie animals are provided. The animals carry a mutant APC allele from a second animal species or have been genetically engineered to contain an insertion mutation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colerectal cancers, Gardner's Syndrome, as well as the less severe familial polyposis discusses above.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

Figure 1A:
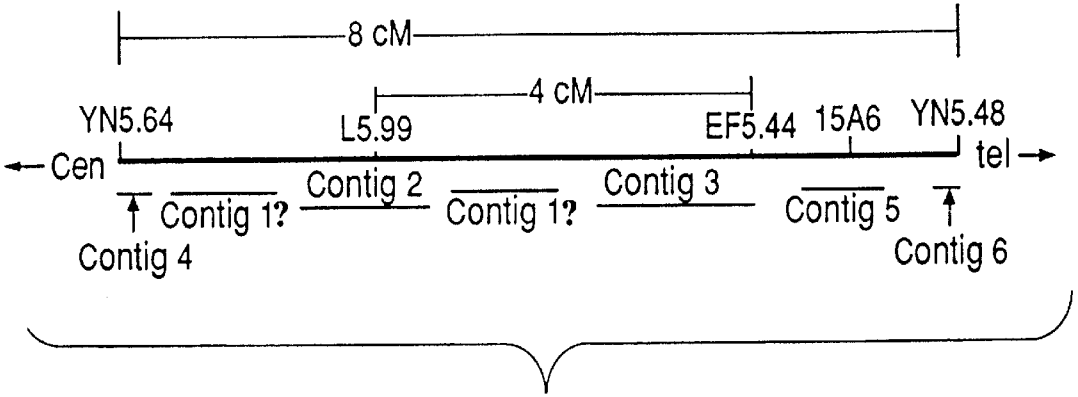
FIG. 1A shows an overview of yeast artificial chromosome (YAC) contigs (contiguous stretches of sequence). Genetic distances between selected RFLP markers from within the contigs are shown in centiMorgans.
Figures 1, 1B:
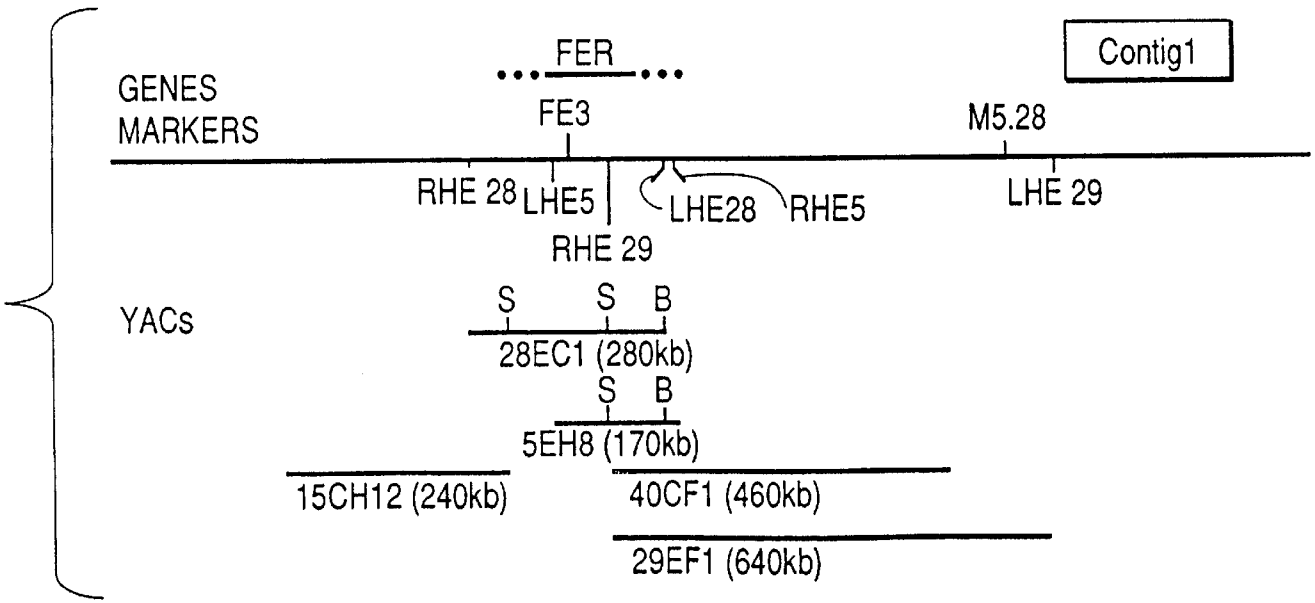
[FIG. 1B shows] *FIGS. 1B-11, and -111 show* a detailed map of the three central contigs. The position of the six identified genes from within the FAP region is shown; the 5' and 3' ends of the transcripts from these genes have in general not yet been isolated, as indicated by the string of dots surrounding the bars denoting the genes positions. Selected restriction endonuclease recognition sites are indicated. B, BssH2; S, SstII; M, MluI; N, NruI.
Figures 1, 1B, 2:
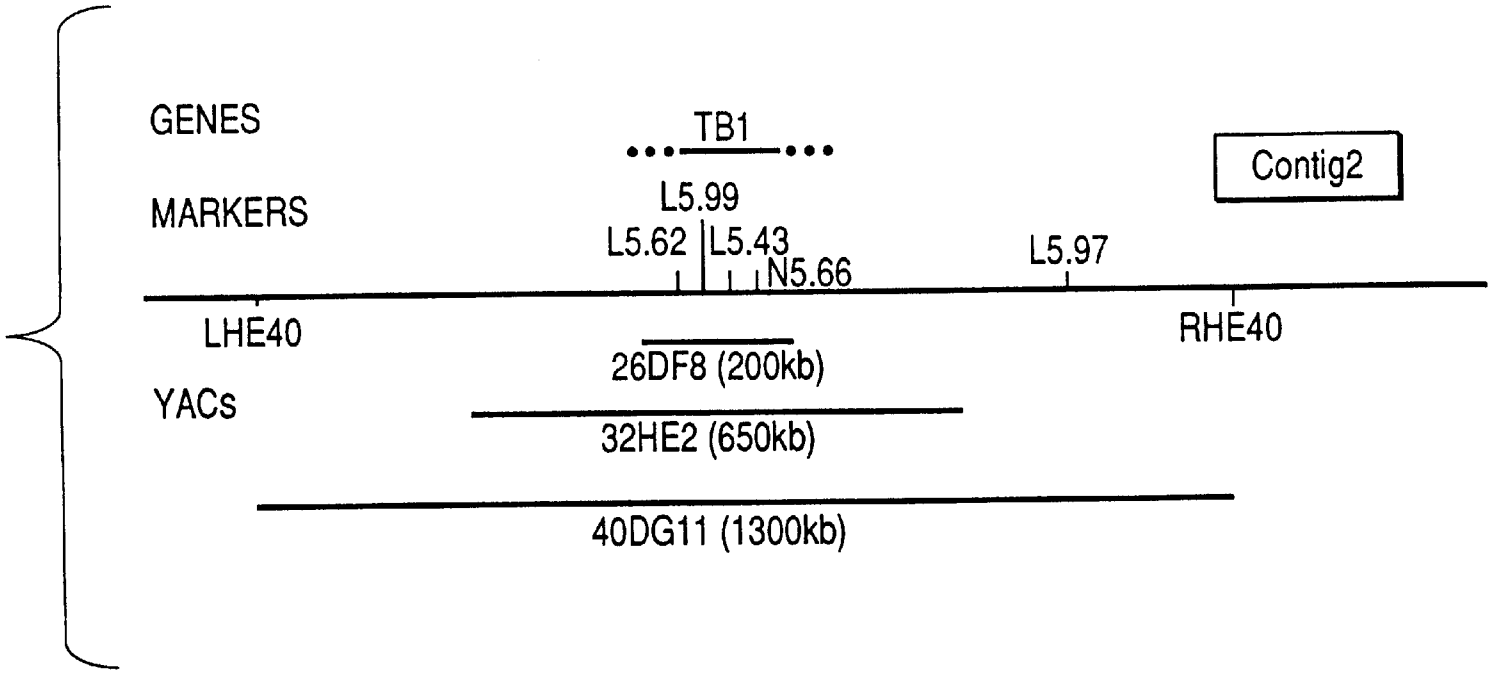
FIG. 2 shows the sequence of TB1 (*SEQ ID NO:5*) and TB2 (*SEQ ID NO: 6*) genes. The cDNA sequence of the TB1 gene was determined from the analysis of 11 cDNA clones derived from normal colon and liver, as described in the text. A total of 2314 bp were contained within the overlapping cDNA clones, defining an ORF of 424 amino acids beginning at nucleotide 1. Only the predicted amino acids from the ORF are shown. The carboxy-terminal end of the ORF has apparently been identified, but the 5' end of the TB1 transcript has not yet been precisely determined.
Figures 1, 1B, 2, 3:
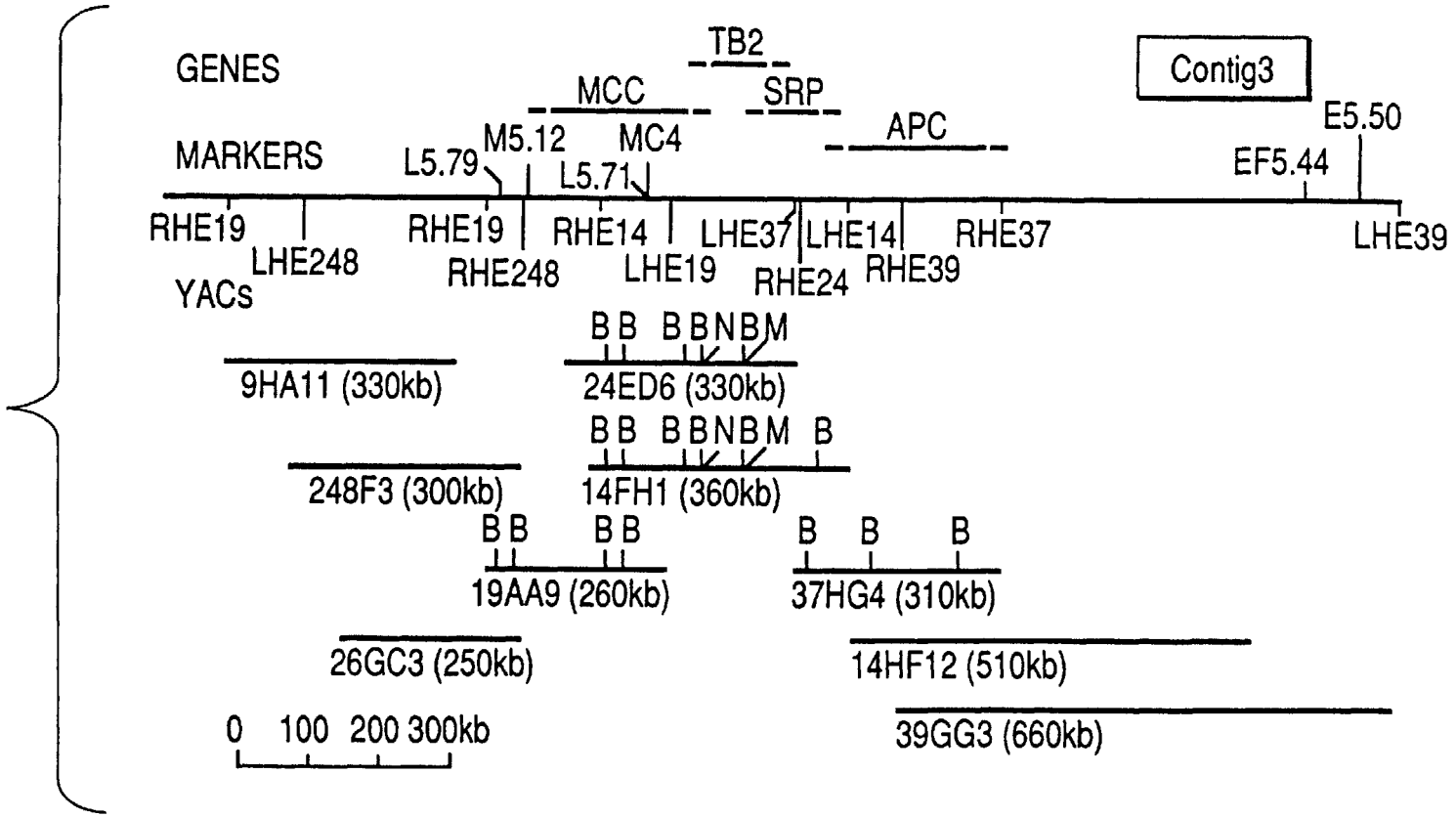

[FIG. 3 shows] *FIGS. 3A–3C* (*collectively, FIG. 3*) *show* the sequence of the APC gene product (*SEQ ID NO: 7*). The cDNA sequence was determined through the analysis of 87 cDNA clones derived from normal colon, liver, and brain. A total of 8973 bp were contained within overlapping cDNA clones, defining an ORF of [2842] *2843* amino acids. In frame stop codons surrounded this ORF, as described in the text, suggesting that the entire APC gene product was represented in the ORF illustrated. Only the predicted amino acids are shown.

FIG. 4 shows the local similarity between human APC (*SEQ ID NO: 2*) and ral2 (*SEQ ID NO: 8*) of yeast. Local similarity among the APC (*SEQ ID NO: 2*) and MCC genes (*SEQ ID NO: 10*) and the m3 muscarinic acetylcholine receptor (*SEQ ID NO: 9*) is shown. The region of the mAChR shown corresponds to that responsible for coupling the receptor to G proteins. The connecting lines indicate identities; dots indicate related amino acids residues.

Figure 5:
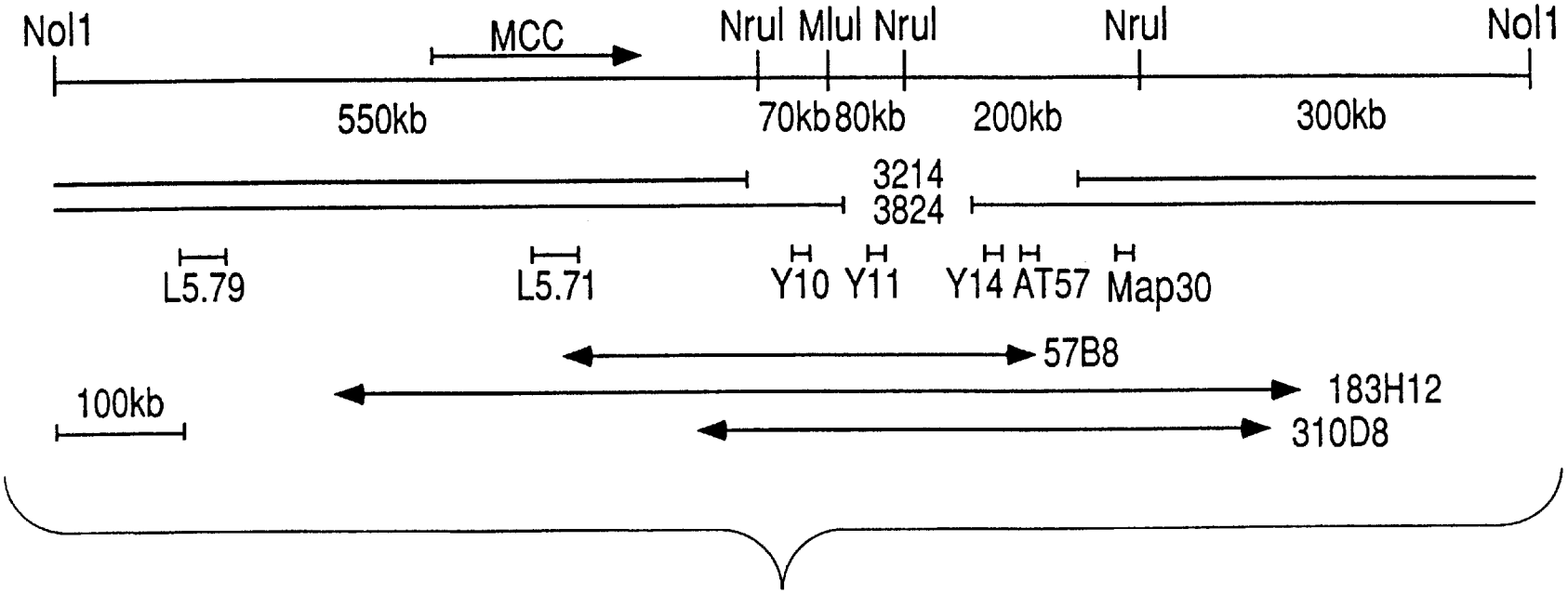

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are indicated above the map.

FIG. 6 shows the DNA sequence (*SEQ ID NO: 3*) and predicted amino acid sequence of DP1 (TB2) (*SEQ ID NO: 4*). The nucleotide numbering begins at the most 5' nucleotide isolated. A proposed initiation methionine (base 77) is indicated in bold type. The entire coding sequence is presented.

[FIG. 7 shows] *FIGS. 7A–7W* (*collectively, FIG. 7*) *show* the cDNA (*SEQ ID NO: 1*) and predicted amino acid sequence of DP2.5 (APC)[,] (*SEQ ID NO: 2*). The nucleotide numbering begins at the proposed initiation methionine. The nucleotides and amino acids of the alternatively spliced exon (exon 9; nucleotide positions [934–1236] *957–1259*) are presented in lower case letters. At the 3' end, a poly(A) addition signal occurs at 9530, and one cDNA clone has a poly(A) at 9563. Other cDNA clones extend beyond 9563, however, and their consensus sequence is included here.

Figure 8A:
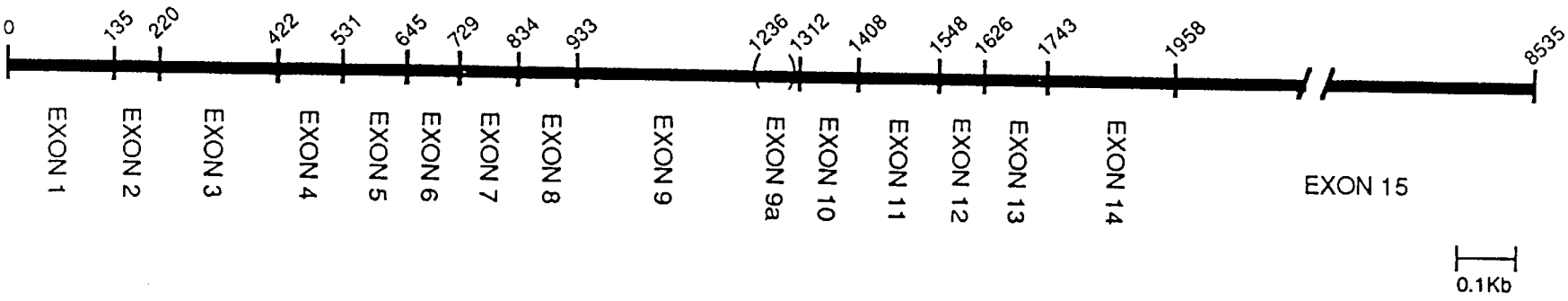
Figures 1, 8B:
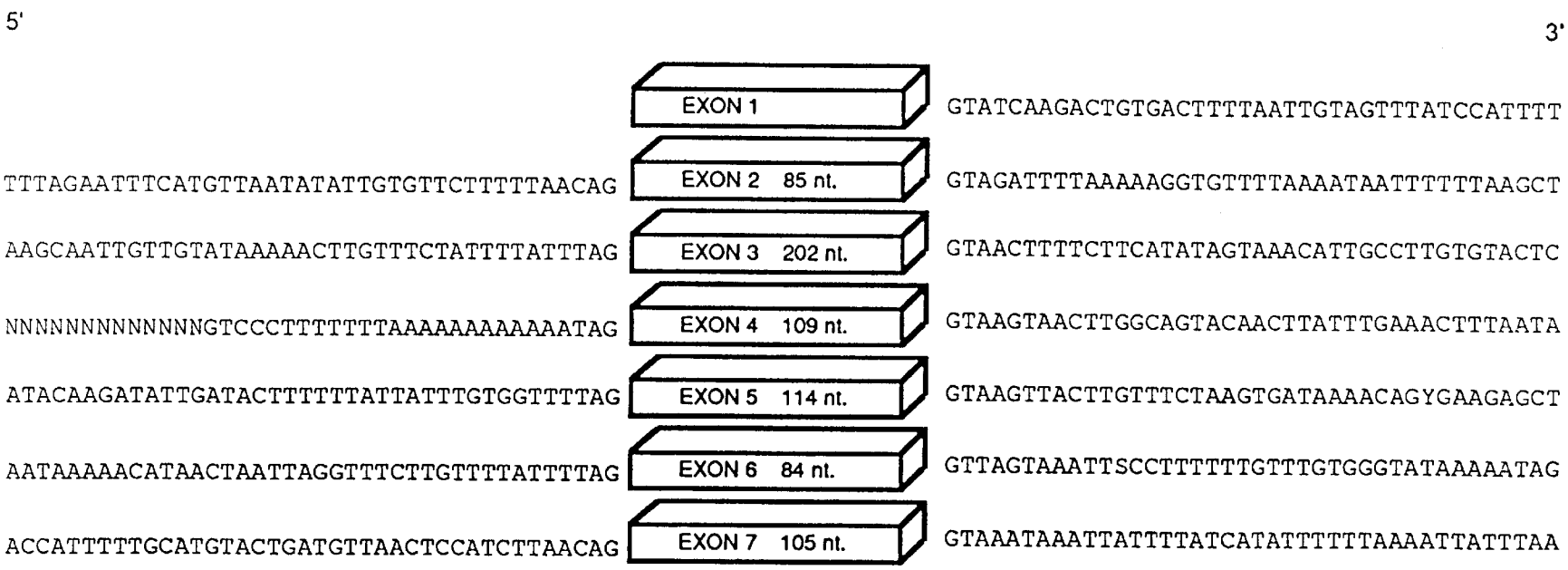
Figures 2, 8B:
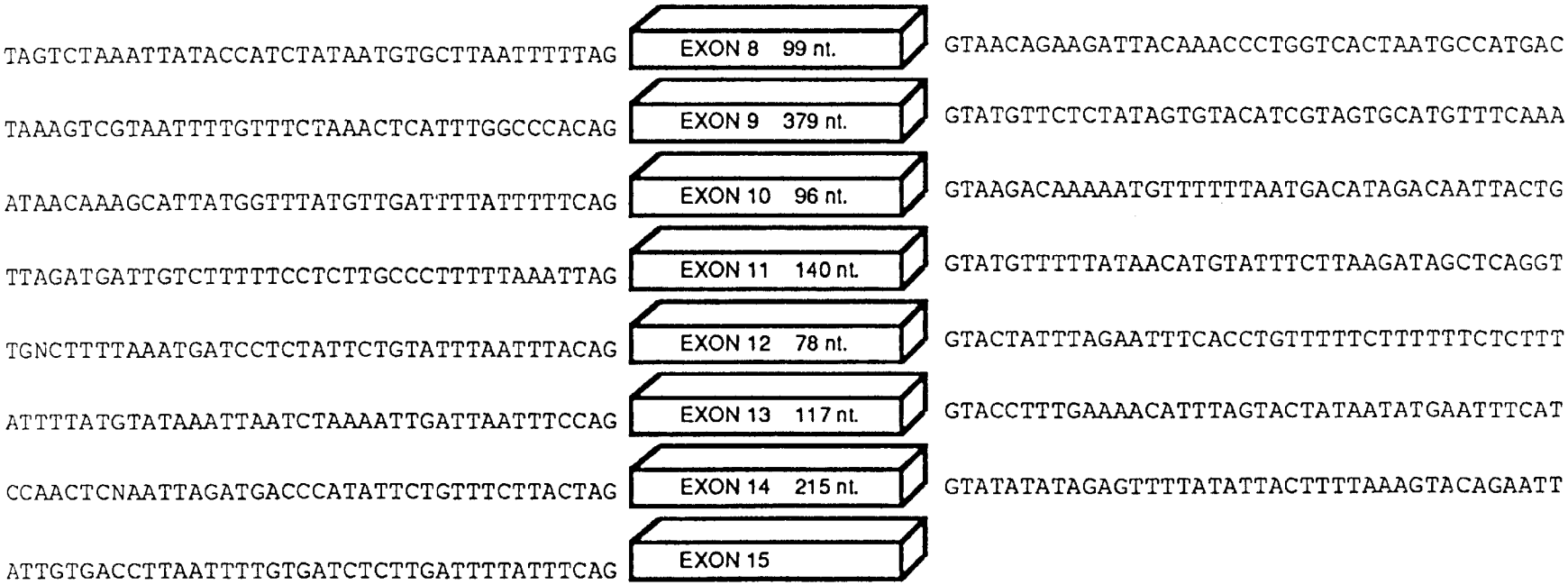

FIG. 8 shows the arrangement of exons in DP2.5 (APC)[, (A)] *FIG. 8A*. Exon 9 corresponds to nucleotides 933–1312; exon 9a corresponds m nucleotides 1236–1312. The stop codon in the cDNA is at nucleotide 8535. [(B)] *FIG. 8B* Partial intronic sequence surrounding each exon is shown (*SEQ ID NOS: 11–38*). *5'intron sequences of exons 2, 3, 4, 5, 6, 7, 8, 9, 10, 11, 12, 13, 14, and 15 are shown in SEQ ID NOS: 12, 14, 16, 18, 20, 22, 24, 26, 28, 30, 32, 34, 36, 38, respectively, 3'intron sequences of exons 1, 2, 3, 4, 5, 6, 7, 8, 9, 10, 11, 12, 13, and 14 are shown in SEQ ID NOS: 11, 13, 15, 17, 19, 21, 23, 25, 27, 29, 31, 33, 35, 37, respectively*.

DETAILED DESCRIPTION

It is a discovery of the present invention that mutational events associated with tumorigenesis occur in a previously unknown gene on chromosome 5q named here the APC (Adenomamus Polyposis Coli) gene. Although it was previously known that deletion of alleles on chromosome 5q were common in certain types of cancers, it was not known that a target gene of these deletions was the APC gene. Further it was not known that other types of mutational events in the APC gene are also associated with cancers, The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations—including deletions. The alteration may be due to either rearrangements such as insertions, inversions, and deletions, or to point mutations, Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatieally mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. No. 4,683,203; and U.S. Pat. No. 4,683,195. Specific primers which can be used in order to amplify the gene will be discussed in more detail below. The ligase chain reaction, which is known in the art, can also be used to amplify APC sequences. See Wu et al., Genomics, Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ALUMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindred persons of an affected individual for the presence of the APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Alteration of wild-type genes can also be detected on the basis of the alteration of a wild-type expression product of the gene. Such expression products include both the APC mRNA as well as the APC protein product. The sequences of these products are shown in [FIGS. 3 and 7] *FIGS. 3A–3C and 7A–7W*. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismateh detection can be used to detect point mutations in the gene or its mRNA product. While these techniques are less sensitive than sequencing, they are simpler to perform on a large number of tumor samples. An example of a mismateh cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type AIsC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismateh is detected by RNase A, it cleaves at the site of the mismateh. Thus, when the annealed RNA preparation is separated on an electrophoretie gel matrix, if a mismateh has been detected and cleaved by RNase A, an RNA product will be seen which is smaller than the full-length duplex RNA for the riboprobe and the mRNA or DNA. The riboprobe need not be the full length of the ArC mRNA or gene but can be a segment of either. If the riboprobe comprises only a segment of the ArC mRNA or gene it will be desirable to use a number of these probes to screen the whole mRNA sequence for mismatehes.

In similar fashion, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretie mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the ArC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the APC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the rumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gone.

Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC genes or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene on chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonueleotide synthesizing machines which are commercially available. Given the sequence of the APC open reading frame shown in [FIG. 7] *FIGS. 7A–7W* (*SEQ ID NO: 1*), design of particular primers is well within the skill of the art.

The nueleic acid probes provided by the present invention are useful for a number of purposes. They can be used in Southern hybridization to genomie DNA and in the RNase protection method for detecting point mutations already discussed above. The probes can be used to detect PCR amplification products. They may also be used to detect mismatehes with the APC gene or mRNA using other techniques. Mismatehes can be detected using either enzymes (e.g., S1 nuclease), chemicals (e.g., hydroxylamine or osmium tetroxide and piperidine), or changes in electrophoretie mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nueleic acid probes is used to compose a kit for detecting alteration of wild-type APC genes. The kit allows for hybridization to the entire APC gene. The probes may overlap with each other or be contiguous.

If a riboprobe is used to detect mismatehes with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, colorimetic, or fluorometric material, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the APC gene. These are useful to detect similar mutations in other patients on the basis of hybridization rather than mismatehes. These are discussed above and referred to as allele-specific probes. As mentioned above, the APC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes. Provided with the APC coding sequence shown in [FIG. 7] *FIGS. 7A–7W* (SEQ ID NO:1), design of particular probes is well within the skill of the ordinary artisan.

According to the present invention a method is also provided of supplying wild-type APC function to a cell which carries mutant APC alleles. Supplying such function should suppress neoplastic growth of the recipient cells. The wild-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes both for recombination and for extrachromosomal maintenance are known in the art and any suitable vector may be used. Methods for introducing DNA into cells such as electropotation, calcium phosphate co-precipitation and viral transduction are known in the art and the choice of method is within the competence of the routineer. Cells transformed with the wild-type APC gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed phenotype of the cell will be determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant APC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in [FIG. 3 or 7 (SEQ ID NO:7 or 1)] *FIGS. 3A–3C and 7A–7W* (*SEQ ID NOS: 2 or 7*). [These two sequences differ slightly and appear to be indicate the existence of two different forms of the APC protein.] Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or in vitro.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells, or amniotic fluid for mutations of the APC gene. Alteration of a wild-type APC allele, whether for example, by point mutation or by deletion, can be detected by any of the means discussed above.

Molecules of cDNA according to the present invention are intron-free, APC gene coding molecules. They can be made by reverse transcriptase using the APC mRNA-as a template. These molecules can be propagated in vectors and cell lines as is known in the art. Such molecules have the sequence shown in SEQ ID NO: 7. The cDNA can also be made using the techniques of synthetic chemistry given the sequence disclosed herein.

A short region of homology has been identified between APC and the human m3 muscarinic acetylcholine receptor (mAChR). This chornology was largely confined to 29 residues in which 6 out of 7 amino acids (EL(GorA)GLQA) were identical (See FIG. 4 (*SEQ ID NO: 9*)). Initially, it was not known whether this hornology was significant, because many other proteins had higher levels of global hornology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mAChR at the analogous protein position. These 21 residues overlap the 19 amino acid hornology between APC and m3 mAChR.

This connection between APC and the G protein activating region of mAChR is intriguing in light of previous investigations relating G proteins to cancer. For example, the RAS oneogenes, which are often mutated in colorectal cancers (Vogelstein, et al., N. Engl. J. Med., Vol. 319, p. 525 (1988); Bos et al., Nature Vol. 327, p. 293 (1987)), are members of the G protein family (Bourne, et al., Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, Vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindae. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg., 157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in normal colon cells and in colorectal, lung, and bladder tumors.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Three contigs encompassing approximately 4 Mb were contained within the central portion of this region. The YAC's constituting these contigs, together with the markers used for their isolation and orientations, are shown in FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in mierotiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleie Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACs. The termini of the 28EC1 YAC were sequenced to derive markers RHE28 and LHE28, respectively. The sequences of these two markers were then used to isolate YAC clones 15CH12 (from RHE28) and 40CF1 and 29EF1 (from LHE28). These five YAC's formed a config encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC 39GG3 allowed connection of the initial contig 3 clones through YAC 37HG4 (FIG. 1B). *YAC37HG4 was deposited at the National Collection of Industrial and Marine Bacteria (NCIMB), P.O. Box 31, 23 St. Machar Drive, Aberdeen AB2 1RY, Scotland, under Accession No. 4035A, FB3 on Dec. 17, 1990.*

Multipoint linkage analysis with the various markers used to define the contigs, combined with PFGE analysis, showed that contigs 1 and 2 were centromecic to contig 3. These contigs were used as tools to orient and/or identify genes which might be responsible for FAP. Six genes were found to lie within this cluster of YAC's, as follows:

Contig #1: FER - The FER gene was discovered through its hornology to the vital oncogene ABL (Hao et al., supra). It has an intrinsic tyrosine kinase activity, and in situ hybridization with an FER probe showed that the gene was located at 5q11–23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human gertomit DNA. Thus, the YAC mapping results were consistent with the FER linkage data and PFGE analyses.

Contig 2:TB1 - TB1 was identified through a cross-hybridization approach. Exons of genes are often evolutionarily conserved while introns and intergenie regions are much less conserved. Thus, if a human probe cross-hybridizes strongly to the DNA from non-primate species, there is a reasonable chance that it contains exon sequences. Subclones of the cosraids shown in FIG. 1 were used to [semen] *screen* Southern blots containing rodent DNA samples. A subclone of cosmid N5.66 (p 5.66-4) was shown to strongly hybridize to rodent DNA, and this clone was used to [semen] *screen* cDNA libraries derived from normal adult colon and fetal liver. The ends of the initial eDNA clones obtained in this screen were then used to extend the eDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids (*SEQ ID NO: 5*). The product of this gene was not globally homologous to any other sequence in the current database but showed two significant local similarities to a family of ADP, ATP carrier/translocator proteins and mitochondrial brown fat uncoupling proteins which are widely distributed from yeast to mammals. These conserved regions of TB1 (underlined in FIG. 2A) may define a predictive motif for this sequence family. In addition, TB1 appeared to contain a signal peptide (or mitochondrial targeting sequence) as well as at least 7 transmembrane domains.

Conrig 3: MCC, TB2, SRP and APC - The MCC gene was also discovered through a cross-hybridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the coding region of MCC was approximately 50 kb proximal to the centromeric end of a 200 kb deletion found in an FAP patient. MCC cDNA probes detected a 10 kb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a cDNA library from normal colon. One of the cDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (*SEQ ID NO: 6*) (FIG. 2B). The gene detected by YS39 was named TB2. Searches of nucleotide and protein databases revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. The gene corresponding to this transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14FH1. However, the 3' end of the APC gene was found in 14FH1 as well as 37HG4. Analogously, the 5' end of the MCC coding region was found in YAC clones 19AA9 and 26GC3 but not 24ED6 or 14FH1, while the 3' end displayed the opposite pattern. Thus, MCC and APC transcription units pointed in opposite directions, with the direction of transcription going from centromeric to telomeric in the case of MCC, and telomeric to centromeric in the case of APC. PFGE analysis of YAC DNA digested with various restriction endonucleases showed that TB2 and SRP were between MCC and APC, and that the 3' ends of the coding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain

[2,842] *2843* amino acids [(FIG. 3)] *FIGS. 3A–3C* (*SEQ ID NO: 7*). The results of database searching with the APC gene product were quite complex due to the presence of large segments with locally biased amino acid compositions. In spite of this, APC could be roughly divided into two domains. The N-terminal 25% of the protein had a high content of leueine residues (12%) and showed local sequence similarities to myosins, various intermediate filament proteins (e.g., desrain, vimentin, neurofilaments) and Drosophila armadillo/human plakoglobin. The latter protein is a component of adhesive junctions (desmosomes) joining epithelial cells (Franke et al., Proc. Natl. Acad. Sci. U.S.A., Vol. 86, p. 4027 (1989); Perlet et al., Cell, Vol. 63, p. 1167 (1990)) The C-terminal 75% of APC (residues 731- 2832) is 17% serine by composition with setinc residues more or less uniformly distributed. This large domain also contains local concentrations of charged (mostly acidic) and proline residues. There was no indication of potential signal peptides, transmembrane regions, or nuclear targeting signals in APC, suggesting a cytoplasmic localization.

To detect short similarities to APC, a database search was performed using the PAM-40 matrix (Altsehul. J. Mol. Bio., Vol. 219, p. 555 (1991). Potentially interesting matches to several proteins were found. The most suggestive of these involved the ral2 gene product of yeast, which is implicated in the regulation of ras activity (Fukul et al., Mol. Cell. Biol., Vol. 9, p. 5617 (1989)). Little is known about how ral2 might interact with ras but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both are implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "spacer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of APC. The potential for both APC and MCC to form coiled coils is interesting in that such structures often mediate homo- and hetero-oligomerization.

Finally, it had previously been noted that MCC shared a short similarity with the region of the m3 muscarinic acetylcholine receptor (mAChR) known to regulate specificity of G-protein coupling. The APC gene also contained a local similarity to the region of the m3 mAChR (*SEQ ID NO: 9*) that overlapped with the MCC similarity (*SEQ ID NO: 10*) (FIG. 4B). Although the similarities to ral2 (*SEQ ID NO: 8*) (FIG. 4A) and m3 mAChR (*SEQ ID NO: 9*) (FIG. 4B) were not statistically significant, they were intriguing in light of previous observations relating G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER, TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-[AGAAGGATCCCTTGTGCAGTGTGGA] *AGAAGGATCCCTTGTGCAGTGTGGA*-3'(*SEQ ID NO: 95*) and 5'-GACAG*GA*TCCTGAAGCTGAGTTTG-3'(*SEQ ID NO: 96*). The underlined nucleotides were altered from the true FER sequence to create BamHI sites. The cell lines used were JW and Dill, both derived from colorectal cancers of FAP patients. (C. Paraskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequenced in their entirety. The PCR products were cloned in the BamHI site of Bluescript SK (Stratagene) and pools of at least 50 clones were sequenced en masse using T7 polymerase, as described in Nigro et al., Nature 342,705 (1989).

Only a single conservative amino acid change (GTG-<CTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' (*SEQ ID NO: 97*) and 5'-GGAATAATTAGGTCTCCAA-3' (*SEQ ID NO: 98*). PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and APC in FAP and sporadic rolorectal tumors. Each of these genes is linked and encompassed by conrig 3 (see FIG. 1).

Several lines of evidence suggested that this conrig was of particular interest. First, at least three of the four genes in this conrig were within the deleted region identified in two FAP patients. (See Example 5 infra.) Second, allelic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with sporadic CRC. Only two examples of somatic changes were observed in over 200 tumors studied: a rearrangement/deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of conrig 3 genes in patients with FAP. We chose to examine MCC and APC, rather than TB2 or SRP, because of the somatic mutations in MCC and APC noted above. To facilitate the identification of subtle alterations, the genomic sequences of MCC and APC exons were determined (see Table I*; SEQ ID NOS: 24–38*). These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions. approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the APC gene. The three exons examined included those containing nt 822-930, 931-1309, and the first 300 nt of the most distal exon (nt 1956-2256). PCR and RNase protection analysis were performed as described in Kinzler et al. supra, using the primers underlined in Table I (*SEQ ID NO: 24–38*). The primers for nt 1956-2256 were 5'-GCAAATCCTAAGAGAGAACAA-3' (*SEQ ID NO: 99*) and 5'-GATGGCAAGCTTGAGCCAG-3'(*SEQ ID NO: 100*).

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nueleic Acids Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demonstrated the same abnormal RNase protection pattern indicated that both had a C to T transition at codon 301 that resulted in a change from arginine (CGA) to a stop codon (TGA). This change was not present in 200 individuals without FAP. As this point mutation resulted in the predicted loss of the recognition site for the enzyme Taq I, appropriate PCR products could be digested with Taq I to detect the mutation. This allowed us to determine that the stop codon co-segregated with disease phenotype in members of the family of P24. The inheritance of this change in affected members of the pedigree provides additional evidence for the importance of the mutation.

Cloning and sequencing of the PCR product from FAP patient P93 indicated a C to G transversion at codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9. In addition to these germline mutations, we identified several somatic mutations of MCC and APC in sporadic CRC's. Seventeen MCC exons were examined in 90 sporadic colorectal cancers by RNase protection analysis. In each case where an abnormal RNase protection pattern was observed, the corresponding PCR products were cloned and sequenced. This led to the identification of six point mutations (two described previously) (Kinzler et al., supra), each of which was not found in the germline of these patients (Table IIB). Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822-930, 931-1309, and 1406-1545 (Table I). A total of three mutations were identified, each of which proved to be somatic. Tumor T27 contained a somatic mutation of C GA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codon (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Bioehem. Biophys. Res. Comm. 130, 118 (1985). PCR was performed using the primers 5'-GTTCCAGCAGTGTCACAG-3' (*SEQ ID NO: 101*) and 5'-GGGAGATTTCGCTCCTGA-3' (*SEQ ID NO: 102*). A PCR product containing codon 1338 was amplified from the archival DNA and used to show that the stop codon represented a somatic mutation present in the original primary tumor and in cell lines derived from the primary and metastatie tumor sites, but not from normal tissue of the patient.

The ten point mutations in the MCC and APC genes so far discovered in sporadic CRCs are summarized in Table IIB. Analysis of the number of mutant and wild-type PCR clones obtained from each of these tumors showed that in eight of the ten eases, the wild-type sequence was present in approximately equal proportions to the mutant. This was confirmed by RFLP analysis using flanking markers from chromosome 5q which demonstrated that only two of the ten tumors (T135 and T201) exhibited an allelie deletion on chromosome 5q. These results are consistent with previous observations showing that 20–40% of sporadic colorectal tumors had allelie deletions of chromosome 5q. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that had been mapped into a region near the APC locus to identify small deletions or rearrangements. Two of these cosmids, L5.71 and L5.79, hybridized with a 1200 kb NotI fragment in DNAs from most or the FAP patients screened.

The DNA of one FAP patient, 3214, showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb NotI fragment that was transmitted to her two unaffected offspring. These observations indicated that the mutant polyposis allele is on the same chromosome as the 940 kb NotI fragment. A simple interpretation is that APC patients 3214 and 4711 each carry a 260 kb deletion within the APC locus.

If a deletion were present, then other enzymes might also expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, MluI fragments in patients 3214 and 4711 also showed an increase in size consistent with the deletion of an MluI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 3214 showed only a 940 kb NotI fragment, she had not inherited the 1200 kb fragment present in the unaffected father's DNA. This observation suggests that he must be heterozygous for, and have transmitted, either a deletion of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were both found to lie on a 550 kb NotI-NruI fragment and, therefore, on the same side or an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHW141, which contains about 40% of chromosome 5, was digested with NotI and electrophoresed under pulsed-field gel (PFG) conditions; EcoRI fragments from the 1200 kb region of this gel were cloned into a phage vector. Probe Map30 was isolated from this library. In normal individuals probe Map30 hybridizes to the 1200 kb NotI fragment and to a 200 kb NruI fragment. This latter hybridization places Map30 disrat, with respect to the locations of L5.71 and L5.79, to the NruI site of the 550 kb NotI-NruI fragment.

Because Map30 hybridized to the abnormal, 1300 kb NruI fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and MluI did not reveal abnormal bands, indicating that if a deletion were present, its boundaries must lie distal to the NruI and MluI sites of the fragments identified by L5.79. Consistent with this expectation, hybridization of Map30 to DNA from patient 3824 identified a 760 kb MluI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb MluI fragment identified by Map30 is distinct from the 830 kb MluI fragment identified previously by L5.79 was demonstrated by hybridization of Map30 and L5.79 to a NotI-MluI double digest of DNA from the hybrid cell (HHW1159) containing the nondeleted chromosome 5 homolog of patient 3214. As previously indicated, this hybrid is interpreted as missing one of the NotI sites that define the 1200 kb fragment. A 620 kb NotI-MluI fragment was seen with probe L5.79, and an 860 kb fragment was seen witch Map30. Therefore, the 830 kb MluI fragment recognized by probe L5.79 must contain a NotI site in HHW1159 DNA; because the 860 kb MluI fragment remains intact, it does not carry this NotI site and must be distinct from the 830 kb MluI fragment.

EXAMPLE 5

This example demonstrates the isolation of human sequences which span the region deleted in the two unrelated FAP patients characterized in Example 4.

A strong prediction of the hypothesis that patients 3214 and 3824 carry deletions is that some sequences present on normal chromosome 5 homologs would be missing from the hypothesized deletion homologs. Therefore, to develop gertomit probes that might confirm the deletions, as well as to identify genes from the region, YAC clones from a conrig seeded by cosmid L5.79 were localized from a library containing seven haploid human genome equivalents (Albertsen et al., Proc. Natl. Acad. Sci. U.S.A., Vol. 87, pp. 4256–4260 (1990))with respect to the hypothesized deletions. Three clones, YACs 57B8, 310D8, and 183H12, were found to overlap the deleted region.

Importantly, one end of YAC 57B8 (clone AT57) was found to lie within the patient 3214 deletion. Inverse polymerase chain reaction (PCR) defined the end sequences of the insert of YAC 57B8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHW1159) carrying the normal chromosome 5 homolog. This result supported the interpretation that the abnormal restriction fragments found in the DNA of patient 3214 result from a deletion.

Additional support for the hypothesis of deletion in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoR1 fragments from YAC 183H12, Y10 and Y14, were localized within the patient 3214 deletion by their failure hybridizie to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-MluI fragment seen with probe L5.79 in normal DNA, indicating its location as L5.79-proximal to the deleted MluI site and placing it between the MluI site and the L5.79-proximal NruI site. The MluI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 kb NotI-MluI fragment, placing it L5.79-distal to the MluI site, but proximal to the second NruI site. Hybridization to the same (860 kb) MluI fragment as Map30 confirmed the localization of probe Y11 L5.79-distal to the MluI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and deleted in patient 3214, with respect to L5.79 and Map30, is L5.79-Y10-Y11-Y14-Map30.

The 100 kb deletion of patient 3824 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the MluI digest, probe Y14 hybridized to the 860 kb and 760 kb fragments of patient 3824 DNA, but probe Y11 hybridized only to the 860 kb fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations. therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (Kinzler et al., supra). It was therefore of interest to map this gene with respect to the deletions in FAP patients. Hybridization of MCC probes with an overlapping series of YAC clones extending in either direction from L5.71 showed that the 3' end of MCC must be oriented toward the region of the two FAP deletions.

Therefore, two 3' cDNA clones from MCC were mapped with respect to the deletions: clone 1CI (bp 2378–4181) and clone 7 (bp 2890–3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the cDNA clones consists of a single 2.5 kb exon. These two clones were hybridized to DNAs from the YACs spanning the FAP region. Clone 7 fails to hybridize to YAC 310D8, although it does hybridize to YACs 183H12 and 5738; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone contig is likely to be located more than 45 kb from the deletion of patient 3214 and, therefore, more than 100 kb from the deletion of patient 3824.

EXAMPLE 7

This example identifies three genes within the deleted region of chromosome 5 in the two unrelated FAP patients characterized in Example 4.

Genomie clones were used to semen cDNA libraries in three separate experiments. One screening was done with a phage clone derived from YAC 310D8 known to span the 260 kb deletion of patient 3214. A large-insert phage library was constructed from this YAC; screening with Y11 identified λ205, which mapped within both deletions. When clone λ205 was used to probe a random-, plus oligo(dT)-, primed fetal brain cDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above.

cDNA walks yielded a cDNA conrig of 3.0–3.5 kb, and included two clones containing terminal poly(A) sequences. This size corresponds to the 3.5 kb band seen by Northern analysis. Sequencing of the first 3163 bp of the cDNA conrig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the $NH_2$-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle. SRP19 (Lingelbach et al., supra). Hybridization experiments mapped YS-11 within both deletions. The sequence of this clone, however, was found to be complex. Although 454 bp of the 1032 bp sequence of YS-11 were identical to the GenBank entry for the SRP19 gene. another 578 bp appended 5' to the SRP19 sequence was found to consist of previously unreported sequence containing no extended open reading frames. This suggested that YS-11 was either a chimetic clone containing two independent inserts or a clone of an incompletely processed or aberrant message. If YS-11 were a conventional chimetic clone, the independent segments would not be expected to map to the same physical region. The segments resulting from anomalous processing of a continuous transcript, however, would map to a single chromosomai region.

Inverse PCR with primers specific to the two ends of YS-11, the SRP19 end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomie sequence was also seen after these 78 bp, suggesting the presence of a splice junction, and supporting the view that YS-11 represents an irregular message.

Starting with V5, successive 5' and 3' walks were performed; the resulting cDNA contig consisted of more than 100 clones, which defined a new transcript, DP2. Clones walking in the 5' direction crossed the 3824 deletion breakpoint farthest from L5.71; since its 3' end is closer to this cosmid than its 5' end, the transcriptional orientation of DP2 is opposite to that of MCC and DP1.

The third screening approach relied on hybridization with a 120 kb MluI fragment from YAC 57B8. This fragment hybridizes with probe Y11 and completely spans the 100 kb deletion in patient 3824. the fragment was purified on two preparative PFGs, labeled, and used to screen a fetal brain cDNA library. A number of cDNA clones previously identified in the development of the DP1 and DP2 configs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 7.

The consensus cDNA sequence of DP2.5 suggests that the entire coding sequence of DP2.5 has been obtained and is 8532 bp long. The most 5' ATG codon occurs two codons from an in-frame stop and conforms to the Kozak initiation consensus (Kozak, Nucl. Acids. Res., Vol. 12, p. 857–872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to that identified as APC above.

An alternatively spliced exon at nucleotide 934 of the DP2.5 transcript is of potential interest. it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP2.5.

To obtain DNA sequence adjacent to the exons of the genes DP1, DP2.5, and SRP19, sequencing substrate was obtained by inverse PCR amplification of DNAs from two YACs, 310D8 and 183H12, that span the deletions. Ligation at low concentration cyclized the restriction enzyme-digested YAC DNAs. Oligonucleotides with sequencing tails, designed in inverse orientation at intervals along the cDNAs, primed PCR amplification from the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table III (*SEQ ID NOS: 39–94*). With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences.

The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250–400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766–70 (1989) and Genomies, Vol. 5, pp. 874–879 (1989) as applied to DP1, SRP19 and DP2.5.

SSCP analysis identifies most single- or multiple-base changes in DNA fragments up to 400 bases in length. Sequence alterations are detected as shifts in eleetrophoretie mobility of single-stranded DNA on nondenaturing aerylamide gels; the two complementary strands of a DNA segment usually resolve as two SSCP conformers of distinct mobilities. However, if the sample is from an individual heterozygous for a base-pair variant within the amplified segment, often three or more bands are seen. In some eases, even the sample from a homozygous individual will show multiple bands. Base-pair-change variants are identified by differences in pattern among the DNAs of the sample set.

Exons of the candidate genes were amplified by PCR from the DNAs of 61 related FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15 of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobillties. The normal conformers from the host individuals were sequenced also. Bands were cut from the dried acrylamide gels, and the DNA was eluted. PCR amplification of these DNAs provided template for sequencing.

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain a deletion of two adjacent nucleotides, at positions 730 and 731 in the cDNA sequence [(FIG. 7)] *FIGS. 7A–7W* (*SEQ ID NO: 1*). The normal sequence at this splice junction is *CAG*GGTCA (intronic sequence underlined), with the intron-exon boundary between the two repetitions of AG. The mutant allele in this patient has the sequence CAGGTCA. Although this exchange is at the 5' splice site, comparison with known consensus sequences of splice junctions would suggest that a functional splice junction is maintained. If this new splice junction were functional, the mutation would introduce a frameshift that creates a stop codon 15 nueleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient 3746 is heterozygous for a 2 bp deletion.

The unique conformer found in exon 8 of patient 3460 was found to carry a C-T transition, at position 904 in the cDNA sequence of DP2.5 (shown in FIG. 7), which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleotide (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an aerylamide-urea denaturing along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position 1500, changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the patient's parents displayed the normal pattern of conformers for exon 7, as did DNA from the patients's wife and one of his offspring. The two other children, however, displayed the same new conformers as their affected father. Testing of the patient and his parents with highly polymorphic VNTR (variable number of tandem repeat) markers showed a 99.98% likelihood that they are his biological parents.

These observations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene: first, in exon 11, at position 1458, a substitution of T to C creating an RsaI restriction site but no amino acid change; and second, in exon 15, at positions 5037 and 5271, substitutions of A to G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated (*SEQ ID NOS: 11–38*).

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomie template. Two forms of exon 9 were found in DP2.5: one is the complete exon; and the other, labeled exon 9A, is the result of a splice into the interior of the exon that deletes bases 934 to 1236 in the mRNA and removes 101 amino acids from the predicted protein (see [FIG. 7] *SEQ ID NOS: 1 & 2*).

EXAMPLE 13

This example demonstrates the mapping of the FAP deletions with respect to the APC exons.

Somatie cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomie DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatie cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be assessed. All tissue types tested (brain, lung, aorta, spleen, heart, kidney, liver, stomach, placenta, and eolonie mueosa) and cultured cell lines (lymphoblasts, HL60, and ehorioeareinoma) expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistent with the size of the sequenced cDNA.

EXAMPLE 15

This example discusses structural features of the APC protein predicted from the sequence.

The cDNA consensus sequence of APC predicts that the longer, more abundant form of the message codes for a [2842 or 28444] *2843* amino acid peptide with a mass of 311.8 kd. This predicted APC peptide was compared with the current data bases of protein and DNA sequences using both Intelligenetics and GCG software packages. No genes with a high degree of amino acid sequence similarity were found. Although many short (approximately 20 amino acid) regions of sequence similarity were uncovered, none was sufficiently strong to reveal which, if any, might represent functional hornology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132 (1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem, Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table 4). The intervening sequences between the seven repeat regions contained 114, 116, 151, 205, 107, and 58 amino acids, respectively. Finally, residues 2200–24000 contain a 200 amino acid basic domain.

SEQUENCE LISTING (1) GENERAL INFORMATION:

(iii) NUMBER OF SEQUENCES: 102

(2) INFORMATION FOR SEQ ID NO:1:

(i) SEQUENCE CHARACTERISTICS:
(A) LENGTH: 8532 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homo sapiens (vii) IMMEDIATE SOURCE:
(B) CLONE: DP2.5(APC)

(viii) SEQUENCE DESCRIPTION: SEQ ID NO:1:

```
ATGGCTGCAG CTTCATATGA TCAGTTGTTA AAGCAAGTTG AGGCACTGAA GATGGAGAAC     60

TCAAATCTTC GACAAGAGCT AGAAGATAAT TCCAATCATC TTACAAAACT GGAAACTGAG    120

GCATCTAATA TGAAGGAAGT ACTTAAACAA CTACAAGGAA GTATTGAAGA TGAAGCTATG    180

GCTTCTTCTG GACAGATTGA TTTATTAGAG CGTCTTAAAG AGCTTAACTT AGATAGCAGT    240

AATTTCCCTG GAGTAAAACT GCGGTCAAAA ATGTCCCTCC GTTCTTATGG AAGCCGGGAA    300

GGATCTGTAT CAAGCCGTTC TGGAGAGTGC AGTCCTGTTC CTATGGGTTC ATTTCCAAGA    360

AGAGGGTTTG TAAATGGAAG CAGAGAAAGT ACTGGATATT TAGAAGAACT TGAGAAAGAG    420

AGGTCATTGC TTCTTGCTGA TCTTGACAAA GAAGAAAAGG AAAAAGACTG GTATTACGCT    480

CAACTTCAGA ATCTCACTAA AAGAATAGAT AGTCTTCCTT TAACTGAAAA TTTTTCCTTA    540

CAAACAGATA TGACCAGAAG GCAATTGGAA TATGAAGCAA GGCAAATCAG AGTTGCGATG    600

GAAGAACAAC TAGGTACCTG CCAGGATATG GAAAAACGAG CACAGCGAAG AATAGCCAGA    660

ATTCAGCAAA TCGAAAAGGA CATACTTCGT ATACGACAGC TTTTACAGTC CCAAGCAACA    720

GAAGCAGAGA GGTCATCTCA GAACAAGCAT GAAACCGGCT CACATGATGC TGAGCGGCAG    780

AATGAAGGTC AAGGAGTGGG AGAAATCAAC ATGGCAACTT CTGGTAATGG TCAGGGTTCA    840

ACTACACGAA TGGACCATGA AACAGCCAGT GTTTTGAGTT CTAGTAGCAC ACACTCTGCA    900

CCTCGAAGGC TGACAAGTCA TCTGGGAACC AAGGTGGAAA TGGTGTATTC ATTGTTGTCA    960

ATGCTTGGTA CTCATGATAA GGATGATATG TCGCGAACTT TGCTAGCTAT GTCTAGCTCC   1020

CAAGACAGCT GTATATCCAT GCGACAGTCT GGATGTCTTC CTCTCCTCAT CCAGCTTTTA   1080

CATGGCAATG ACAAAGACTC TGTATTGTTG GGAAATTCCC GGGGCAGTAA AGAGGCTCGG   1140

GCCAGGGCCA GTGCAGCACT CCACAACATC ATTCACTCAC AGCCTGATGA CAAGAGAGGC   1200

AGGCGTGAAA TCCGAGTCCT TCATCTTTTG GAACAGATAC GCGCTTACTG TGAAACCTGT   1260

TGGGAGTGGC AGGAAGCTCA TGAACCAGGC ATGGACCAGG ACAAAAATCC AATGCCAGCT   1320

CCTGTTGAAC ATCAGATCTG TCCTGCTGTG TGTGTTCTAA TGAAACTTTC ATTTGATGAA   1380

GAGCATAGAC ATGCAATGAA TGAACTAGGG GGACTACAGG CCATTGCAGA ATTATTGCAA   1440

GTGGACTGTG AAATGTACGG GCTTACTAAT GACCACTACA GTATTACACT AAGACGATAT   1500

GCTGGAATGG CTTTGACAAA CTTGACTTTT GGAGATGTAG CCAACAAGGC TACGCTATGC   1560

TCTATGAAAG GCTGCATGAG AGCACTTGTG GCCCAACTAA AATCTGAAAG TGAAGACTTA   1620
```

-continued

```
CAGCAGGTTA TTGCAAGTGT TTTGAGGAAT TTGTCTTGGC GAGCAGATGT AAATAGTAAA   1680
AAGACGTTGC GAGAAGTTGG AAGTGTGAAA GCATTGATGG AATGTGCTTT AGAAGTTAAA   1740
AAGGAATCAA CCCTCAAAAG CGTATTGAGT GCCTTATGGA ATTTGTCAGC ACATTGCACT   1800
GAGAATAAAG CTGATATATG TGCTGTAGAT GGTGCACTTG CATTTTTGGT TGGCACTCTT   1860
ACTTACCGGA GCCAGACAAA CACTTTAGCC ATTATTGAAA GTGGAGGTGG GATATTACGG   1920
AATGTGTCCA GCTTGATAGC TACAAATGAG GACCACAGGC AAATCCTAAG AGAGAACAAC   1980
TGTCTACAAA CTTTATTACA ACACTTAAAA TCTCATAGTT TGACAATAGT CAGTAATGCA   2040
TGTGGAACTT TGTGGAATCT CTCAGCAAGA AATCCTAAAG ACCAGGAAGC ATTATGGGAC   2100
ATGGGGGCAG TTAGCATGCT CAAGAACCTC ATTCATTCAA AGCACAAAAT GATTGCTATG   2160
GGAAGTGCTG CAGCTTTAAG GAATCTCATG GCAAATAGGC CTGCGAAGTA CAAGGATGCC   2220
AATATTATGT CTCCTGGCTC AAGCTTGCCA TCTCTTCATG TTAGGAAACA AAAAGCCCTA   2280
GAAGCAGAAT TAGATGCTCA GCACTTATCA GAAACTTTTG ACAATATAGA CAATTTAAGT   2340
CCCAAGGCAT CTCATCGTAG TAAGCAGAGA CACAAGCAAA GTCTCTATGG TGATTATGTT   2400
TTTGACACCA ATCGACATGA TGATAATAGG TCAGACAATT TTAATACTGG CAACATGACT   2460
GTCCTTTCAC CATATTTGAA TACTACAGTG TTACCCAGCT CCTCTTCATC AAGAGGAAGC   2520
TTAGATAGTT CTCGTTCTGA AAAAGATAGA AGTTTGGAGA GAGAACGCGG AATTGGTCTA   2580
GGCAACTACC ATCCAGCAAC AGAAAATCCA GGAACTTCTT CAAAGCGAGG TTTGCAGATC   2640
TCCACCACTG CAGCCCAGAT TGCCAAAGTC ATGGAAGAAG TGTCAGCCAT TCATACCTCT   2700
CAGGAAGACA GAAGTTCTGG GTCTACCACT GAATTACATT GTGTGACAGA TGAGAGAAAT   2760
GCACTTAGAA GAAGCTCTGC TGCCCATACA CATTCAAACA CTTACAATTT CACTAAGTCG   2820
GAAAATTCAA ATAGGACATG TTCTATGCCT TATGCCAAAT TAGAATACAA GAGATCTTCA   2880
AATGATAGTT TAAATAGTGT CAGTAGTAGT GATGGTTATG GTAAAAGAGG TCAAATGAAA   2940
CCCTCGATTG AATCCTATTC TGAAGATGAT GAAAGTAAGT TTTGCAGTTA TGGTCAATAC   3000
CCAGCCGACC TAGCCCATAA AATACATAGT GCAAATCATA TGGATGATAA TGATGGAGAA   3060
CTAGATACAC CAATAAATTA TAGTCTTAAA TATTCAGATG AGCAGTTGAA CTCTGGAAGG   3120
CAAAGTCCTT CACAGAATGA AAGATGGGCA AGACCCAAAC ACATAATAGA AGATGAAATA   3180
AAACAAAGTG AGCAAAGACA ATCAAGGAAT CAAAGTACAA CTTATCCTGT TTATACTGAG   3240
AGCACTGATG ATAAACACCT CAAGTTCCAA CCACATTTTG GACAGCAGGA ATGTGTTTCT   3300
CCATACAGGT CACGGGGAGC CAATGGTTCA GAAACAAATC GAGTGGGTTC TAATCATGGA   3360
ATTAATCAAA ATGTAAGCCA GTCTTTGTGT CAAGAAGATG ACTATGAAGA TGATAAGCCT   3420
ACCAATTATA GTGAACGTTA CTCTGAAGAA GAACAGCATG AAGAAGAAGA GAGACCAACA   3480
AATTATAGCA TAAAATATAA TGAAGAGAAA CGTCATGTGG ATCAGCCTAT TGATTATAGT   3540
TTAAAATATG CCACAGATAT TCCTTCATCA CAGAAACAGT CATTTTCATT CTCAAAGAGT   3600
TCATCTGGAC AAAGCAGTAA AACCGAACAT ATGTCTTCAA GCAGTGAGAA TACGTCCACA   3660
CCTTCATCTA ATGCCAAGAG GCAGAATCAG CTCCATCCAA GTTCTGCACA GAGTAGAAGT   3720
GGTCAGCCTC AAAAGGCTGC CACTTGCAAA GTTTCTTCTA TTAACCAAGA AACAATACAG   3780
ACTTATTGTG TAGAAGATAC TCCAATATGT TTTTCAAGAT GTAGTTCATT ATCATCTTTG   3840
TCATCAGCTG AAGATGAAAT AGGATGTAAT CAGACGACAC AGGAAGCAGA TTCTGCTAAT   3900
ACCCTGCAAA TAGCAGAAAT AAAAGAAAAG ATTGGAACTA GGTCAGCTGA AGATCCTGTG   3960
AGCGAAGTTC CAGCAGTGTC ACAGCACCCT AGAACCAAAT CCAGCAGACT GCAGGGTTCT   4020
```

-continued

```
AGTTTATCTT CAGAATCAGC CAGGCACAAA GCTGTTGAAT TTTCTTCAGG AGCGAAATCT   4080
CCCTCCAAAA GTGGTGCTCA GACACCCAAA AGTCCACCTG AACACTATGT TCAGGAGACC   4140
CCACTCATGT TTAGCAGATG TACTTCTGTC AGTTCACTTG ATAGTTTTGA GAGTCGTTCG   4200
ATTGCCAGCT CCGTTCAGAG TGAACCATGC AGTGGAATGG TAAGTGGCAT TATAAGCCCC   4260
AGTGATCTTC CAGATAGCCC TGGACAAACC ATGCCACCAA GCAGAAGTAA AACACCTCCA   4320
CCACCTCCTC AAACAGCTCA AACCAAGCGA GAAGTACCTA AAAATAAAGC ACCTACTGCT   4380
GAAAAGAGAG AGAGTGGACC TAAGCAAGCT GCAGTAAATG CTGCAGTTCA GAGGGTCCAG   4440
GTTCTTCCAG ATGCTGATAC TTTATTACAT TTTGCCACGG AAAGTACTCC AGATGGATTT   4500
TCTTGTTCAT CCAGCCTGAG TGCTCTGAGC CTCGATGAGC CATTTATACA GAAAGATGTG   4560
GAATTAAGAA TAATGCCTCC AGTTCAGGAA AATGACAATG GGAATGAAAC AGAATCAGAG   4620
CAGCCTAAAG AATCAAATGA AAACCAAGAG AAAGAGGCAG AAAAAACTAT TGATTCTGAA   4680
AAGGACCTAT TAGATGATTC AGATGATGAT GATATTGAAA TACTAGAAGA ATGTATTATT   4740
TCTGCCATGC CAACAAAGTC ATCACGTAAA GCAAAAAAGC CAGCCCAGAC TGCTTCAAAA   4800
TTACCTCCAC CTGTGGCAAG GAAACCAAGT CAGCTGCCTG TGTACAAACT TCTACCATCA   4860
CAAAACAGGT TGCAACCCCA AAAGCATGTT AGTTTTACAC CGGGGGATGA TATGCCACGG   4920
GTGTATTGTG TTGAAGGGAC ACCTATAAAC TTTTCCACAG CTACATCTCT AAGTGATCTA   4980
ACAATCGAAT CCCCTCCAAA TGAGTTAGCT GCTGGAGAAG GAGTTAGAGG AGGAGCACAG   5040
TCAGGTGAAT TTGAAAAACG AGATACCATT CCTACAGAAG GCAGAAGTAC AGATGAGGCT   5100
CAAGGAGGAA AAACCTCATC TGTAACCATA CCTGAATTGG ATGACAATAA AGCAGAGGAA   5160
GGTGATATTC TTGCAGAATG CATTAATTCT GCTATGCCCA AAGGGAAAAG TCACAAGCCT   5220
TTCCGTGTGA AAAAGATAAT GGACCAGGTC CAGCAAGCAT CTGCGTCGTC TTCTGCACCC   5280
AACAAAAATC AGTTAGATGG TAAGAAAAAG AAACCAACTT CACCAGTAAA ACCTATACCA   5340
CAAAATACTG AATATAGGAC ACGTGTAAGA AAAAATGCAG ACTCAAAAAA TAATTTAAAT   5400
GCTGAGAGAG TTTTCTCAGA CAACAAAGAT TCAAAGAAAC AGAATTTGAA AAATAATTCC   5460
AAGGACTTCA ATGATAAGCT CCCAAATAAT GAAGATAGAG TCAGAGGAAG TTTTGCTTTT   5520
GATTCACCTC ATCATTACAC GCCTATTGAA GGAACTCCTT ACTGTTTTTC ACGAAATGAT   5580
TCTTTGAGTT CTCTAGATTT TGATGATGAT GATGTTGACC TTTCCAGGGA AAAGGCTGAA   5640
TTAAGAAAGG CAAAAGAAAA TAAGGAATCA GAGGCTAAAG TTACCAGCCA CACAGAACTA   5700
ACCTCCAACC AACAATCAGC TAATAAGACA CAAGCTATTG CAAAGCAGCC AATAAATCGA   5760
GGTCAGCCTA AACCCATACT TCAGAAACAA TCCACTTTTC CCCAGTCATC CAAAGACATA   5820
CCAGACAGAG GGGCAGCAAC TGATGAAAAG TTACAGAATT TTGCTATTGA AAATACTCCA   5880
GTTTGCTTTT CTCATAATTC CTCTCTGAGT TCTCTCAGTG ACATTGACCA AGAAAACAAC   5940
AATAAAGAAA ATGAACCTAT CAAAGAGACT GAGCCCCCTG ACTCACAGGG AGAACCAAGT   6000
AAACCTCAAG CATCAGGCTA TGCTCCTAAA TCATTTCATG TTGAAGATAC CCCAGTTTGT   6060
TTCTCAAGAA ACAGTTCTCT CAGTTCTCTT AGTATTGACT CTGAAGATGA CCTGTTGCAG   6120
GAATGTATAA GCTCCGCAAT GCCAAAAAAG AAAAAGCCTT CAAGACTCAA GGGTGATAAT   6180
GAAAAACATA GTCCCAGAAA TATGGGTGGC ATATTAGGTG AAGATCTGAC ACTTGATTTG   6240
AAAGATATAC AGAGACCAGA TTCAGAACAT GGTCTATCCC CTGATTCAGA AAATTTTGAT   6300
TGGAAAGCTA TTCAGGAAGG TGCAAATTCC ATAGTAAGTA GTTTACATCA AGCTGCTGCT   6360
GCTGCATGTT TATCTAGACA AGCTTCGTCT GATTCAGATT CCATCCTTTC CCTGAAATCA   6420
```

-continued

```
GGAATCTCTC TGGGATCACC ATTTCATCTT ACACCTGATC AAGAAGAAAA ACCCTTTACA   6480
AGTAATAAAG GCCCACGAAT TCTAAAACCA GGGGAGAAAA GTACATTGGA AACTAAAAAG   6540
ATAGAATCTG AAAGTAAAGG AATCAAAGGA GGAAAAAAAG TTTATAAAAG TTTGATTACT   6600
GGAAAAGTTC GATCTAATTC AGAAATTTCA GGCCAAATGA AACAGCCCCT TCAAGCAAAC   6660
ATGCCTTCAA TCTCTCGAGG CAGGACAATG ATTCATATTC CAGGAGTTCG AAATAGCTCC   6720
TCAAGTACAA GTCCTGTTTC TAAAAAAGGC CCACCCCTTA AGACTCCAGC CTCCAAAAGC   6780
CCTAGTGAAG GTCAAACAGC CACCACTTCT CCTAGAGGAG CCAAGCCATC TGTGAAATCA   6840
GAATTAAGCC CTGTTGCCAG GCAGACATCC CAAATAGGTG GGTCAAGTAA AGCACCTTCT   6900
AGATCAGGAT CTAGAGATTC GACCCCTTCA AGACCTGCCC AGCAACCATT AAGTAGACCT   6960
ATACAGTCTC CTGGCCGAAA CTCAATTTCC CCTGGTAGAA ATGGAATAAG TCCTCCTAAC   7020
AAATTATCTC AACTTCCAAG GACATCATCC CCTAGTACTG CTTCAACTAA GTCCTCAGGT   7080
TCTGGAAAAA TGTCATATAC ATCTCCAGGT AGACAGATGA GCCAACAGAA CCTTACCAAA   7140
CAAACAGGTT TATCCAAGAA TGCCAGTAGT ATTCCAAGAA GTGAGTCTGC CTCCAAAGGA   7200
CTAAATCAGA TGAATAATGG TAATGGAGCC AATAAAAAGG TAGAACTTTC TAGAATGTCT   7260
TCAACTAAAT CAAGTGGAAG TGAATCTGAT AGATCAGAAA GACCTGTATT AGTACGCCAG   7320
TCAACTTTCA TCAAAGAAGC TCCAAGCCCA ACCTTAAGAA GAAAATTGGA GGAATCTGCT   7380
TCATTTGAAT CTCTTTCTCC ATCATCTAGA CCAGCTTCTC CCACTAGGTC CCAGGCACAA   7440
ACTCCAGTTT TAAGTCCTTC CCTTCCTGAT ATGTCTCTAT CCACACATTC GTCTGTTCAG   7500
GCTGGTGGAT GGCGAAAACT CCCACCTAAT CTCAGTCCCA CTATAGAGTA TAATGATGGA   7560
AGACCAGCAA AGCGCCATGA TATTGCACGG TCTCATTCTG AAAGTCCTTC TAGACTTCCA   7620
ATCAATAGGT CAGGAACCTG GAAACGTGAG CACAGCAAAC ATTCATCATC CCTTCCTCGA   7680
GTAAGCACTT GGAGAAGAAC TGGAAGTTCA TCTTCAATTC TTTCTGCTTC ATCAGAATCC   7740
AGTGAAAAAG CAAAAAGTGA GGATGAAAAA CATGTGAACT CTATTTCAGG AACCAAACAA   7800
AGTAAAGAAA ACCAAGTATC CGCAAAAGGA ACATGGAGAA AAATAAAAGA AAATGAATTT   7860
TCTCCCACAA ATAGTACTTC TCAGACCGTT TCCTCAGGTG CTACAAATGG TGCTGAATCA   7920
AAGACTCTAA TTTATCAAAT GGCACCTGCT GTTTCTAAAA CAGAGGATGT TTGGGTGAGA   7980
ATTGAGGACT GTCCCATTAA CAATCCTAGA TCTGGAAGAT CTCCCACAGG TAATACTCCC   8040
CCGGTGATTG ACAGTGTTTC AGAAAAGGCA AATCCAAACA TTAAAGATTC AAAAGATAAT   8100
CAGGCAAAAC AAAATGTGGG TAATGGCAGT GTTCCCATGC GTACCGTGGG TTTGGAAAAT   8160
CGCCTGAACT CCTTTATTCA GGTGGATGCC CCTGACCAAA AAGGAACTGA GATAAAACCA   8220
GGACAAAATA ATCCTGTCCC TGTATCAGAG ACTAATGAAA GTTCTATAGT GGAACGTACC   8280
CCATTCAGTT CTAGCAGCTC AAGCAAACAC AGTTCACCTA GTGGGACTGT TGCTGCCAGA   8340
GTGACTCCTT TTAATTACAA CCCAAGCCCT AGGAAAAGCA GCGCAGATAG CACTTCAGCT   8400
CGGCCATCTC AGATCCCAAC TCCAGTGAAT AACAACACAA AGAAGCGAGA TTCCAAAACT   8460
GACAGCACAG AATCCAGTGG AACCCAAAGT CCTAAGCGCC ATTCTGGGTC TTACCTTGTG   8520
ACATCTGTTT AA                                                       8532
```

(2) INFORMATION FOR SEQ ID NO:2:

(i) SEQUENCE CHARACTERISTICS:
(A) LENGTH: 2843 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
```

```
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830
```

```
Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr Pro
   1010                1015                1020

Ile Asn Tyr Ser Leu Lys Tyr Ser Asp Glu Gln Leu Asn Ser Gly Arg
025                 1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
   1090                1095                1100

Arg Gly Ala Asn Gly Ser Glu Thr Asn Arg Val Gly Ser Asn His Gly
105                 1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
   1170                1175                1180

Thr Asp Ile Pro Ser Ser Gln Lys Gln Ser Phe Ser Phe Ser Lys Ser
185                 1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
   1250                1255                1260
```

Glu Asp Thr Pro Ile Cys Phe Ser Arg Cys Ser Ser Leu Ser Ser Leu
265 1270 1275 1280

Ser Ser Ala Glu Asp Glu Ile Gly Cys Asn Gln Thr Thr Gln Glu Ala
1285 1290 1295

Asp Ser Ala Asn Thr Leu Gln Ile Ala Glu Ile Lys Glu Lys Ile Gly
1300 1305 1310

Thr Arg Ser Ala Glu Asp Pro Val Ser Glu Val Pro Ala Val Ser Gln
1315 1320 1325

His Pro Arg Thr Lys Ser Ser Arg Leu Gln Gly Ser Ser Leu Ser Ser
1330 1335 1340

Glu Ser Ala Arg His Lys Ala Val Glu Phe Ser Ser Gly Ala Lys Ser
345 1350 1355 1360

Pro Ser Lys Ser Gly Ala Gln Thr Pro Lys Ser Pro Pro Glu His Tyr
1365 1370 1375

Val Gln Glu Thr Pro Leu Met Phe Ser Arg Cys Thr Ser Val Ser Ser
1380 1385 1390

Leu Asp Ser Phe Glu Ser Arg Ser Ile Ala Ser Ser Val Gln Ser Glu
1395 1400 1405

Pro Cys Ser Gly Met Val Ser Gly Ile Ile Ser Pro Ser Asp Leu Pro
1410 1415 1420

Asp Ser Pro Gly Gln Thr Met Pro Pro Ser Arg Ser Lys Thr Pro Pro
425 1430 1435 1440

Pro Pro Pro Gln Thr Ala Gln Thr Lys Arg Glu Val Pro Lys Asn Lys
1445 1450 1455

Ala Pro Thr Ala Glu Lys Arg Glu Ser Gly Pro Lys Gln Ala Ala Val
1460 1465 1470

Asn Ala Ala Val Gln Arg Val Gln Val Leu Pro Asp Ala Asp Thr Leu
1475 1480 1485

Leu His Phe Ala Thr Glu Ser Thr Pro Asp Gly Phe Ser Cys Ser Ser
1490 1495 1500

Ser Leu Ser Ala Leu Ser Leu Asp Glu Pro Phe Ile Gln Lys Asp Val
505 1510 1515 1520

Glu Leu Arg Ile Met Pro Pro Val Gln Glu Asn Asp Asn Gly Asn Glu
1525 1530 1535

Thr Glu Ser Glu Gln Pro Lys Glu Ser Asn Glu Asn Gln Glu Lys Glu
1540 1545 1550

Ala Glu Lys Thr Ile Asp Ser Glu Lys Asp Leu Leu Asp Asp Ser Asp
1555 1560 1565

Asp Asp Asp Ile Glu Ile Leu Glu Glu Cys Ile Ile Ser Ala Met Pro
1570 1575 1580

Thr Lys Ser Ser Arg Lys Ala Lys Lys Pro Ala Gln Thr Ala Ser Lys
585 1590 1595 1600

Leu Pro Pro Pro Val Ala Arg Lys Pro Ser Gln Leu Pro Val Tyr Lys
1605 1610 1615

Leu Leu Pro Ser Gln Asn Arg Leu Gln Pro Gln Lys His Val Ser Phe
1620 1625 1630

Thr Pro Gly Asp Asp Met Pro Arg Val Tyr Cys Val Glu Gly Thr Pro
1635 1640 1645

Ile Asn Phe Ser Thr Ala Thr Ser Leu Ser Asp Leu Thr Ile Glu Ser
1650 1655 1660

Pro Pro Asn Glu Leu Ala Ala Gly Glu Gly Val Arg Gly Gly Ala Gln
665 1670 1675 1680

Ser Gly Glu Phe Glu Lys Arg Asp Thr Ile Pro Thr Glu Gly Arg Ser

```
                1685                1690                1695

Thr Asp Glu Ala Gln Gly Gly Lys Thr Ser Ser Val Thr Ile Pro Glu
            1700                1705                1710

Leu Asp Asp Asn Lys Ala Glu Glu Gly Asp Ile Leu Ala Glu Cys Ile
        1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
745                 1750                1755                1760

Asn Lys Asn Gln Leu Asp Gly Lys Lys Lys Lys Pro Thr Ser Pro Val
                1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
    1810                1815                1820

Asp Lys Leu Pro Asn Asn Glu Asp Arg Val Arg Gly Ser Phe Ala Phe
825                 1830                1835                1840

Asp Ser Pro His His Tyr Thr Pro Ile Glu Gly Thr Pro Tyr Cys Phe
                1845                1850                1855

Ser Arg Asn Asp Ser Leu Ser Ser Leu Asp Phe Asp Asp Asp Asp Val
            1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
    1890                1895                1900

Gln Ser Ala Asn Lys Thr Gln Ala Ile Ala Lys Gln Pro Ile Asn Arg
905                 1910                1915                1920

Gly Gln Pro Lys Pro Ile Leu Gln Lys Gln Ser Thr Phe Pro Gln Ser
                1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
        1955                1960                1965

Leu Ser Ser Leu Ser Asp Ile Asp Gln Glu Asn Asn Asn Lys Glu Asn
    1970                1975                1980

Glu Pro Ile Lys Glu Thr Glu Pro Pro Asp Ser Gln Gly Glu Pro Ser
985                 1990                1995                2000

Lys Pro Gln Ala Ser Gly Tyr Ala Pro Lys Ser Phe His Val Glu Asp
                2005                2010                2015

Thr Pro Val Cys Phe Ser Arg Asn Ser Ser Leu Ser Ser Leu Ser Ile
            2020                2025                2030

Asp Ser Glu Asp Asp Leu Leu Gln Glu Cys Ile Ser Ser Ala Met Pro
        2035                2040                2045

Lys Lys Lys Lys Pro Ser Arg Leu Lys Gly Asp Asn Glu Lys His Ser
    2050                2055                2060

Pro Arg Asn Met Gly Gly Ile Leu Gly Glu Asp Leu Thr Leu Asp Leu
065                 2070                2075                2080

Lys Asp Ile Gln Arg Pro Asp Ser Glu His Gly Leu Ser Pro Asp Ser
                2085                2090                2095

Glu Asn Phe Asp Trp Lys Ala Ile Gln Glu Gly Ala Asn Ser Ile Val
            2100                2105                2110
```

Ser Ser Leu His Gln Ala Ala Ala Ala Ala Cys Leu Ser Arg Gln Ala
2115 2120 2125

Ser Ser Asp Ser Asp Ser Ile Leu Ser Leu Lys Ser Gly Ile Ser Leu
2130 2135 2140

Gly Ser Pro Phe His Leu Thr Pro Asp Gln Glu Glu Lys Pro Phe Thr
145 2150 2155 2160

Ser Asn Lys Gly Pro Arg Ile Leu Lys Pro Gly Glu Lys Ser Thr Leu
2165 2170 2175

Glu Thr Lys Lys Ile Glu Ser Glu Ser Lys Gly Ile Lys Gly Gly Lys
2180 2185 2190

Lys Val Tyr Lys Ser Leu Ile Thr Gly Lys Val Arg Ser Asn Ser Glu
2195 2200 2205

Ile Ser Gly Gln Met Lys Gln Pro Leu Gln Ala Asn Met Pro Ser Ile
2210 2215 2220

Ser Arg Gly Arg Thr Met Ile His Ile Pro Gly Val Arg Asn Ser Ser
225 2230 2235 2240

Ser Ser Thr Ser Pro Val Ser Lys Lys Gly Pro Pro Leu Lys Thr Pro
2245 2250 2255

Ala Ser Lys Ser Pro Ser Glu Gly Gln Thr Ala Thr Thr Ser Pro Arg
2260 2265 2270

Gly Ala Lys Pro Ser Val Lys Ser Glu Leu Ser Pro Val Ala Arg Gln
2275 2280 2285

Thr Ser Gln Ile Gly Gly Ser Ser Lys Ala Pro Ser Arg Ser Gly Ser
2290 2295 2300

Arg Asp Ser Thr Pro Ser Arg Pro Ala Gln Gln Pro Leu Ser Arg Pro
305 2310 2315 2320

Ile Gln Ser Pro Gly Arg Asn Ser Ile Ser Pro Gly Arg Asn Gly Ile
2325 2330 2335

Ser Pro Pro Asn Lys Leu Ser Gln Leu Pro Arg Thr Ser Ser Pro Ser
2340 2345 2350

Thr Ala Ser Thr Lys Ser Ser Gly Ser Gly Lys Met Ser Tyr Thr Ser
2355 2360 2365

Pro Gly Arg Gln Met Ser Gln Gln Asn Leu Thr Lys Gln Thr Gly Leu
2370 2375 2380

Ser Lys Asn Ala Ser Ser Ile Pro Arg Ser Glu Ser Ala Ser Lys Gly
385 2390 2395 2400

Leu Asn Gln Met Asn Asn Gly Asn Gly Ala Asn Lys Lys Val Glu Leu
2405 2410 2415

Ser Arg Met Ser Ser Thr Lys Ser Ser Gly Ser Glu Ser Asp Arg Ser
2420 2425 2430

Glu Arg Pro Val Leu Val Arg Gln Ser Thr Phe Ile Lys Glu Ala Pro
2435 2440 2445

Ser Pro Thr Leu Arg Arg Lys Leu Glu Glu Ser Ala Ser Phe Glu Ser
2450 2455 2460

Leu Ser Pro Ser Ser Arg Pro Ala Ser Pro Thr Arg Ser Gln Ala Gln
465 2470 2475 2480

Thr Pro Val Leu Ser Pro Ser Leu Pro Asp Met Ser Leu Ser Thr His
2485 2490 2495

Ser Ser Val Gln Ala Gly Gly Trp Arg Lys Leu Pro Pro Asn Leu Ser
2500 2505 2510

Pro Thr Ile Glu Tyr Asn Asp Gly Arg Pro Ala Lys Arg His Asp Ile
2515 2520 2525

Ala Arg Ser His Ser Glu Ser Pro Ser Arg Leu Pro Ile Asn Arg Ser
2530 2535 2540

```
Gly Thr Trp Lys Arg Glu His Ser Lys His Ser Ser Ser Leu Pro Arg
545                 2550                2555                2560

Val Ser Thr Trp Arg Arg Thr Gly Ser Ser Ser Ser Ile Leu Ser Ala
                2565                2570                2575

Ser Ser Glu Ser Ser Glu Lys Ala Lys Ser Glu Asp Glu Lys His Val
            2580                2585                2590

Asn Ser Ile Ser Gly Thr Lys Gln Ser Lys Glu Asn Gln Val Ser Ala
        2595                2600                2605

Lys Gly Thr Trp Arg Lys Ile Lys Glu Asn Glu Phe Ser Pro Thr Asn
    2610                2615                2620

Ser Thr Ser Gln Thr Val Ser Ser Gly Ala Thr Asn Gly Ala Glu Ser
625                 2630                2635                2640

Lys Thr Leu Ile Tyr Gln Met Ala Pro Ala Val Ser Lys Thr Glu Asp
                2645                2650                2655

Val Trp Val Arg Ile Glu Asp Cys Pro Ile Asn Asn Pro Arg Ser Gly
            2660                2665                2670

Arg Ser Pro Thr Gly Asn Thr Pro Pro Val Ile Asp Ser Val Ser Glu
        2675                2680                2685

Lys Ala Asn Pro Asn Ile Lys Asp Ser Lys Asp Asn Gln Ala Lys Gln
    2690                2695                2700

Asn Val Gly Asn Gly Ser Val Pro Met Arg Thr Val Gly Leu Glu Asn
705                 2710                2715                2720

Arg Leu Asn Ser Phe Ile Gln Val Asp Ala Pro Asp Gln Lys Gly Thr
                2725                2730                2735

Glu Ile Lys Pro Gly Gln Asn Asn Pro Val Pro Val Ser Glu Thr Asn
            2740                2745                2750

Glu Ser Ser Ile Val Glu Arg Thr Pro Phe Ser Ser Ser Ser Ser Ser
        2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
785                 2790                2795                2800

Arg Pro Ser Gln Ile Pro Thr Pro Val Asn Asn Asn Thr Lys Lys Arg
                2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val
        2835                2840
```

(2) INFORMATION FOR SEQ ID NO:3:

(i) SEQUENCE CHARACTERISTICS:
(A) LENGTH: 3172 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homo sapiens (vii) IMMEDIATE SOURCE:
(B) CLONE: DP1(TB2)

(ix) FEATURE:
(A) NAME/KEY: CDS
(B) LOCATION: 1..630

(xi) SEQUENCE DESCRIPTION: SEQ ID NO:3:

```
GCA GTC GCC GCT CCA GTC TAT CCG GCA CTA GGA ACA GCC CCG GGN GGC       48
Ala Val Ala Ala Pro Val Tyr Pro Ala Leu Gly Thr Ala Pro Gly Gly
  1               5                  10                  15

GAG ACG GTC CCC GCC ATG TCT GCG GCC ATG AGG GAG AGG TTC GAC CGG       96
Glu Thr Val Pro Ala Met Ser Ala Ala Met Arg Glu Arg Phe Asp Arg
             20                  25                  30

TTC CTG CAC GAG AAG AAC TGC ATG ACT GAC CTT CTG GCC AAG CTC GAG      144
Phe Leu His Glu Lys Asn Cys Met Thr Asp Leu Leu Ala Lys Leu Glu
         35                  40                  45

GCC AAA ACC GGC GTG AAC AGG AGC TTC ATC GCT CTT GGT GTC ATC GGA      192
Ala Lys Thr Gly Val Asn Arg Ser Phe Ile Ala Leu Gly Val Ile Gly
     50                  55                  60

CTG GTG GCC TTG TAC CTG GTG TTC GGT TAT GGA GCC TCT CTC CTC TGC      240
Leu Val Ala Leu Tyr Leu Val Phe Gly Tyr Gly Ala Ser Leu Leu Cys
 65                  70                  75                  80

AAC CTG ATA GGA TTT GGC TAC CCA GCC TAC ATC TCA ATT AAA GCT ATA      288
Asn Leu Ile Gly Phe Gly Tyr Pro Ala Tyr Ile Ser Ile Lys Ala Ile
                 85                  90                  95

GAG AGT CCC AAC AAA GAA GAT GAT ACC CAG TGG CTG ACC TAC TGG GTA      336
Glu Ser Pro Asn Lys Glu Asp Asp Thr Gln Trp Leu Thr Tyr Trp Val
            100                 105                 110

GTG TAT GGT GTG TTC AGC ATT GCT GAA TTC TTC TCT GAT ATC TTC CTG      384
Val Tyr Gly Val Phe Ser Ile Ala Glu Phe Phe Ser Asp Ile Phe Leu
        115                 120                 125

TCA TGG TTC CCC TTC TAC TAC ATG CTG AAG TGT GGC TTC CTG TTG TGG      432
Ser Trp Phe Pro Phe Tyr Tyr Met Leu Lys Cys Gly Phe Leu Leu Trp
    130                 135                 140

TGC ATG GCC CCG AGC CCT TCT AAT GGG GCT GAA CTG CTC TAC AAG CGC      480
Cys Met Ala Pro Ser Pro Ser Asn Gly Ala Glu Leu Leu Tyr Lys Arg
145                 150                 155                 160

ATC ATC CGT CCT TTC TTC CTG AAG CAC GAG TCC CAG ATG GAC AGT GTG      528
Ile Ile Arg Pro Phe Phe Leu Lys His Glu Ser Gln Met Asp Ser Val
                165                 170                 175

GTC AAG GAC CTT AAA GAC AAG TCC AAA GAG ACT GCA GAT GCC ATC ACT      576
Val Lys Asp Leu Lys Asp Lys Ser Lys Glu Thr Ala Asp Ala Ile Thr
            180                 185                 190

AAA GAA GCG AAG AAA GCT ACC GTG AAT TTA CTG GGT GAA GAA AAG AAG      624
Lys Glu Ala Lys Lys Ala Thr Val Asn Leu Leu Gly Glu Glu Lys Lys
        195                 200                 205

AGC ACC TAAACCAGAC TAAACCAGAC TGGATGGAAA CTTCCTGCCC TCTCTGTACC       680
Ser Thr
    210

TTCCTACTGG AGCTTGATGT TATATTAGGG ACTGTGGTAT AATTATTTTA ATAATGTTGC    740

CTTGGAAACA TTTTTGAGAT ATTAAAGATT GGAATGTGTT GTAAGTTTCT TTGCTTACTT    800

TTACTGTCTA TATATATAGG GAGCACTTTA AACTTAATGC AGTGGGCAGT GTCCACGTTT    860

TTGGAAAATG TATTTTGCCT CTGGGTAGGA AAAGATGTAT GTTGCTATCC TGCAGGAAAT    920

ATAAACTTAA AATAAAATTA TATACCCCAC AGGCTGTGTA CTTTACTGGG CTCTCCCTGC    980

ACGSATTTTC TCTGTAGTTA CATTTAGGRT AATCTTTATG GTTCTACTTC CTRTAATGTA   1040

CAATTTTATA TAATTCNGRA ATGTTTTTAA TGTATTTGTG CACATGTACA TATGGAAATG   1100

TTACTGTCTG ACTACANCAT GCATCATGCT CATGGGGAGG GAGCAGGGGA AGGTTGTATG   1160

TGTCATTTAT AACTTCTGTA CAGTAAGACC ACCTGCCAAA AGCTGGAGGA ACCATTGTGC   1220

TGGTGTGGTC TACTAAATAA TACTTTAGGA AATACGTGAT TAATATGCAA GTGAACAAAG   1280

TGAGAAATGA AATCGAATGG AGATTGGCCT GGTTGTTTCC GTAGTATATG GCATATGAAT   1340

ACCAGGATAG CTTTATAAAG CAGTTAGTTA GTTAGTTACT CACTCTAGTG ATAAATCGGG   1400
```

```
AAATTTACAC ACACACACAC ACACACACAC ACACACACAC ACACACACAC ACACACACAG   1460
AGTACCCTGT AACTCTCAAT TCCCTGAAAA ACTAGTAATA CTGTCTTATC TGCTATAAAC   1520
TTTACATATT TGTCTATTGT CAAGATGCTA CANTGGAMNC CATTTCTGGT TTTATCTTCA   1580
NAGSGGAGAN ACATGTTGAT TTAGTCTTCT TTCCCAATCT TCTTTTTTAA MCCAGTTTNA   1640
GGMNCTTCTG RAGATTTGYC CACCTCTGAT TACATGTATG TTCTYGTTTG TATCATKAGC   1700
AACAACATGC TAATGRCGAC ACCTAGCTCT RAGMGCAATT CTGGGAGANT GARAGGNWGT   1760
ATARAGTMNC CCATAATCTG CTTGGCAATA GTTAAGTCAA TCTATCTTCA GTTTTTCTCT   1820
GGCCTTTAAG GTCAAACACA AGAGGCTTCC CTAGTTTACA AGTCAGAGTC ACTTGTAGTC   1880
CATTTAAATG CCCTCATCCG TATTCTTTGT GTTGATAAGC TGCACAKGAC TACATAGTAA   1940
GTACAGANCA GTAAAGTTAA NNCGGATGTC TCCATTGATC TGCCAANTCG NTATAGAGAG   2000
CAATTTGTCT GGACTAGAAA ATCTGAGTTT TACACCATAC TGTTAAGAGT CCTTTTGAAT   2060
TAAACTAGAC TAAAACAAGT GTATAACTAA ACTAACAAGA TTAAATATCC AGCCAGTACA   2120
GTATTTTTTA AGGCAAATAA AGATGATTAG CTCACCTTGA GNTAACAATC AGGTAAGATC   2180
ATNACAATGT CTCATGATGT NAANAATATT AAAGATATCA ATACTAAGTG ACAGTATCAC   2240
NNCTAATATA ATATGGATCA GAGCATTTAT TTTGGGGAGG AAAACAGTGG TGATTACCGG   2300
CATTTTATTA AACTTAAAAC TTTGTAGAAA GCAAACAAAA TTGTTCTTGG GAGAAAATCA   2360
ACTTTTAGAT TAAAAAAATT TTAAGTAWCT AGGAGTATTT AAATCCTTTT CCCATAAATA   2420
AAAGTACAGT TTTCTTGGTG GCAGAATGAA AATCAGCAAC NTCTAGCATA TAGACTATAT   2480
AATCAGATTG ACAGCATATA GAATATATTA TCAGACAAGA TGAGGAGGTA CAAAAGTTAC   2540
TATTGCTCAT AATGACTTAC AGGCTAAAAN TAGNTNTAAA ATACTATATT AAATTCTGAA   2600
TGCAATTTTT TTTTGTTCCC TTGAGACCAA AATTTAAGTT AACTGTTGCT GGCAGTCTAA   2660
GTGTAAATGT TAACAGCAGG AGAAGTTAAG AATTGAGCAG TTCTGTTGCA TGATTTCCCA   2720
AATGAAATAC TGCCTTGGCT AGAGTTTGAA AAACTAATTG AGCCTGTGCC TGGCTAGAAA   2780
ACAAGCGTTT ATTTGAATGT GAATAGTGTT TCAAAGGTAT GTAGTTACAG AATTCCTACC   2840
AAACAGCTTA AATTCTTCAA GAAAGAATTC CTGCAGCAGT TATTCCCTTA CCTGAAGGCT   2900
TCAATCATTT GGATCAACAA CTGCTACTCT CGGGAAGACT CCTCTACTCA CAGCTGAAGA   2960
AAATGAGCAC ACCCTTCACA CTGTTATCAC CTATCCTGAA GATGTGATAC ACTGAATGGA   3020
AATAAATAGA TGTAAATAAA ATTGAGWTCT CATTTAAAAA AAACCATGTG CCCAATGGGA   3080
AAATGACCTC ATGTTGTGGT TTAAACAGCA ACTGCACCCA CTAGCACAGC CCATTGAGCT   3140
ANCCTATATA TACATCTCTG TCAGTGCCCC TC                                 3172
```

(2) INFORMATION FOR SEQ ID NO:4:

(i) SEQUENCE CHARACTERISTICS:
(A) LENGTH: 210 amino acids
(B) TYPE: amino acid
(D) TOPOLOGY: linear (ii) MOLECULE TYPE: protein (xi) SEQUENCE DESCRIPTION: SEQ ID NO:4:

```
Ala Val Ala Ala Pro Val Tyr Pro Ala Leu Gly Thr Ala Pro Gly Gly
  1               5                  10                  15

Glu Thr Val Pro Ala Met Ser Ala Ala Met Arg Glu Arg Phe Asp Arg
             20                  25                  30

Phe Leu His Glu Lys Asn Cys Met Thr Asp Leu Leu Ala Lys Leu Glu
```

```
         35                  40                  45

Ala Lys Thr Gly Val Asn Arg Ser Phe Ile Ala Leu Gly Val Ile Gly
     50                  55                  60

Leu Val Ala Leu Tyr Leu Val Phe Gly Tyr Gly Ala Ser Leu Leu Cys
 65                  70                  75                  80

Asn Leu Ile Gly Phe Gly Tyr Pro Ala Tyr Ile Ser Ile Lys Ala Ile
                 85                  90                  95

Glu Ser Pro Asn Lys Glu Asp Asp Thr Gln Trp Leu Thr Tyr Trp Val
            100                 105                 110

Val Tyr Gly Val Phe Ser Ile Ala Glu Phe Phe Ser Asp Ile Phe Leu
        115                 120                 125

Ser Trp Phe Pro Phe Tyr Tyr Met Leu Lys Cys Gly Phe Leu Leu Trp
    130                 135                 140

Cys Met Ala Pro Ser Pro Ser Asn Gly Ala Glu Leu Leu Tyr Lys Arg
145                 150                 155                 160

Ile Ile Arg Pro Phe Phe Leu Lys His Glu Ser Gln Met Asp Ser Val
                165                 170                 175

Val Lys Asp Leu Lys Asp Lys Ser Lys Glu Thr Ala Asp Ala Ile Thr
            180                 185                 190

Lys Glu Ala Lys Lys Ala Thr Val Asn Leu Leu Gly Glu Glu Lys Lys
        195                 200                 205

Ser Thr
    210
```

(2) INFORMATION FOR SEQ ID NO:5:

(i) SEQUENCE CHARACTERISTICS:
(A) LENGTH: 434 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Homo sapiens (vii) IMMEDIATE SOURCE:
(B) CLONE: TB1

(xi) SEQUENCE DESCRIPTION: SEQ ID NO:5:

```
Val Ala Pro Val Val Val Gly Ser Gly Arg Ala Pro Arg His Pro Ala
1               5                   10                  15

Pro Ala Ala Met His Pro Arg Arg Pro Asp Gly Phe Asp Gly Leu Gly
            20                  25                  30

Tyr Arg Gly Gly Ala Arg Asp Glu Gln Gly Phe Gly Gly Ala Phe Pro
        35                  40                  45

Ala Arg Ser Phe Ser Thr Gly Ser Asp Leu Gly His Trp Val Thr Thr
    50                  55                  60

Pro Pro Asp Ile Pro Gly Ser Arg Asn Leu His Trp Gly Glu Lys Ser
65                  70                  75                  80

Pro Pro Tyr Gly Val Pro Thr Thr Ser Thr Pro Tyr Glu Gly Pro Thr
                85                  90                  95

Glu Glu Pro Phe Ser Ser Gly Gly Gly Gly Ser Val Gln Gly Gln Ser
            100                 105                 110

Ser Glu Gln Leu Asn Arg Phe Ala Gly Phe Gly Ile Gly Leu Ala Ser
        115                 120                 125

Leu Phe Thr Glu Asn Val Leu Ala His Pro Cys Ile Val Leu Arg Arg
    130                 135                 140
```

```
Gln Cys Gln Val Asn Tyr His Ala Gln His Tyr His Leu Thr Pro Phe
145                 150                 155                 160

Thr Val Ile Asn Ile Met Tyr Ser Phe Asn Lys Thr Gln Gly Pro Arg
                165                 170                 175

Ala Leu Trp Lys Gly Met Gly Ser Thr Phe Ile Val Gln Gly Val Thr
            180                 185                 190

Leu Gly Ala Glu Gly Ile Ile Ser Glu Phe Thr Pro Leu Pro Arg Glu
        195                 200                 205

Val Leu His Lys Trp Ser Pro Lys Gln Ile Gly Glu His Leu Leu Leu
    210                 215                 220

Lys Ser Leu Thr Tyr Val Val Ala Met Pro Phe Tyr Ser Ala Ser Leu
225                 230                 235                 240

Ile Glu Thr Val Gln Ser Glu Ile Ile Arg Asp Asn Thr Gly Ile Leu
                245                 250                 255

Glu Cys Val Lys Glu Gly Ile Gly Arg Val Ile Gly Met Gly Val Pro
            260                 265                 270

His Ser Lys Arg Leu Leu Pro Leu Leu Ser Leu Ile Phe Pro Thr Val
        275                 280                 285

Leu His Gly Val Leu His Tyr Ile Ile Ser Ser Val Ile Gln Lys Phe
    290                 295                 300

Val Leu Leu Ile Leu Lys Arg Lys Thr Tyr Asn Ser His Leu Ala Glu
305                 310                 315                 320

Ser Thr Ser Pro Val Gln Ser Met Leu Asp Ala Tyr Phe Pro Glu Leu
                325                 330                 335

Ile Ala Asn Phe Ala Ala Ser Leu Cys Ser Asp Val Ile Leu Tyr Pro
            340                 345                 350

Leu Glu Thr Val Leu His Arg Leu His Ile Gln Gly Thr Arg Thr Ile
        355                 360                 365

Ile Asp Asn Thr Asp Leu Gly Tyr Glu Val Leu Pro Ile Asn Thr Gln
    370                 375                 380

Tyr Glu Gly Met Arg Asp Cys Ile Asn Thr Ile Arg Gln Glu Glu Gly
385                 390                 395                 400

Val Phe Gly Phe Tyr Lys Gly Phe Gly Ala Val Ile Ile Gln Tyr Thr
                405                 410                 415

Leu His Ala Ala Val Leu Gln Ile Thr Lys Ile Ile Tyr Ser Thr Leu
            420                 425                 430

Leu Gln
```

(2) INFORMATION FOR SEQ ID NO:6:

(i) SEQUENCE CHARACTERISTICS:
(A) LENGTH: 185 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Homo sapiens (vii) IMMEDIATE SOURCE:
(B) CLONE: YS-39(TB2)

(xi) SEQUENCE DESCRIPTION: SEQ ID NO:6:

```
Glu Leu Arg Arg Phe Asp Arg Phe Leu His Glu Lys Asn Cys Met Thr
1               5                   10                  15

Asp Leu Leu Ala Lys Leu Glu Ala Lys Thr Gly Val Asn Arg Ser Phe
```

```
            20                  25                  30

Ile Ala Leu Gly Val Ile Gly Leu Val Ala Leu Tyr Leu Val Phe Gly
        35                  40                  45

Tyr Gly Ala Ser Leu Leu Cys Asn Leu Ile Gly Phe Gly Tyr Pro Ala
    50                  55                  60

Tyr Ile Ser Ile Lys Ala Ile Glu Ser Pro Asn Lys Glu Asp Asp Thr
65                  70                  75                  80

Gln Trp Leu Thr Tyr Trp Val Val Tyr Gly Val Phe Ser Ile Ala Glu
                85                  90                  95

Phe Phe Ser Asp Ile Phe Leu Ser Trp Phe Pro Phe Tyr Tyr Ile Leu
            100                 105                 110

Lys Cys Gly Phe Leu Leu Trp Cys Met Ala Pro Ser Pro Ser Asn Gly
        115                 120                 125

Ala Glu Leu Leu Tyr Lys Arg Ile Ile Arg Pro Phe Phe Leu Lys His
    130                 135                 140

Glu Ser Gln Met Asp Ser Val Val Lys Asp Leu Lys Asp Lys Ala Lys
145                 150                 155                 160

Glu Thr Ala Asp Ala Ile Thr Lys Glu Ala Lys Lys Ala Thr Val Asn
                165                 170                 175

Leu Leu Gly Glu Glu Lys Lys Ser Thr
            180                 185
```

(2) INFORMATION FOR SEQ ID NO:7:

(i) SEQUENCE CHARACTERISTICS:
(A) LENGTH: 2843 amino acids
(B) TYPE: amino acid
(C) STRANDEDNESS: single
(D) TOPOLOGY: linear (ii) MOLECULE TYPE: protein (iii) HYPOTHETICAL: YES (iv) ANTI-SENSE: NO (xi) SEQUENCE DESCRIPTION: SEQ ID NO:7:

```
Met Ala Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
```

```
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590
```

```
Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                1000                1005

His Ser Ala Asn His Met Asp Asp Asn Asp Gly Glu Leu Asp Thr Pro
   1010                1015                1020
```

```
Ile Asn Tyr Ser Leu Lys Tyr Ser Asp Glu Gln Leu Asn Ser Gly Arg
025                 1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
105                 1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
185                 1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
265                 1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Glu Lys Ile Gly
            1300                1305                1310

Thr Arg Ser Ala Glu Asp Pro Val Ser Glu Val Pro Ala Val Ser Gln
        1315                1320                1325

His Pro Arg Thr Lys Ser Ser Arg Leu Gln Gly Ser Ser Leu Ser Ser
    1330                1335                1340

Glu Ser Ala Arg His Lys Ala Val Glu Phe Ser Ser Gly Ala Lys Ser
345                 1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
        1395                1400                1405

Pro Cys Ser Gly Met Val Ser Gly Ile Ile Ser Pro Ser Asp Leu Pro
    1410                1415                1420

Asp Ser Pro Gly Gln Thr Met Pro Pro Ser Arg Ser Lys Thr Pro Pro
425                 1430                1435                1440

Pro Pro Pro Gln Thr Ala Gln Thr Lys Arg Glu Val Pro Lys Asn Lys
```

```
                1445                1450                1455

Ala Pro Thr Ala Glu Lys Arg Glu Ser Gly Pro Lys Gln Ala Ala Val
            1460                1465                1470

Asn Ala Ala Val Gln Arg Val Gln Val Leu Pro Asp Ala Asp Thr Leu
        1475                1480                1485

Leu His Phe Ala Thr Glu Ser Thr Pro Asp Gly Phe Ser Cys Ser Ser
    1490                1495                1500

Ser Leu Ser Ala Leu Ser Leu Asp Glu Pro Phe Ile Gln Lys Asp Val
505                 1510                1515                1520

Glu Leu Arg Ile Met Pro Pro Val Gln Glu Asn Asp Asn Gly Asn Glu
                1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Glu Lys Asp Leu Leu Asp Asp Ser Asp
        1555                1560                1565

Asp Asp Asp Ile Glu Ile Leu Glu Glu Cys Ile Ile Ser Ala Met Pro
    1570                1575                1580

Thr Lys Ser Ser Arg Lys Ala Lys Lys Pro Ala Gln Thr Ala Ser Lys
585                 1590                1595                1600

Leu Pro Pro Pro Val Ala Arg Lys Pro Ser Gln Leu Pro Val Tyr Lys
                1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
        1635                1640                1645

Ile Asn Phe Ser Thr Ala Thr Ser Leu Ser Asp Leu Thr Ile Glu Ser
    1650                1655                1660

Pro Pro Asn Glu Leu Ala Ala Gly Glu Gly Val Arg Gly Gly Ala Gln
665                 1670                1675                1680

Ser Gly Glu Phe Glu Lys Arg Asp Thr Ile Pro Thr Glu Gly Arg Ser
                1685                1690                1695

Thr Asp Glu Ala Gln Gly Gly Lys Thr Ser Ser Val Thr Ile Pro Glu
            1700                1705                1710

Leu Asp Asp Asn Lys Ala Glu Glu Gly Asp Ile Leu Ala Glu Cys Ile
        1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
745                 1750                1755                1760

Asn Lys Asn Gln Leu Asp Gly Lys Lys Lys Lys Pro Thr Ser Pro Val
                1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
    1810                1815                1820

Asp Lys Leu Pro Asn Asn Glu Asp Arg Val Arg Gly Ser Phe Ala Phe
825                 1830                1835                1840

Asp Ser Pro His His Tyr Thr Pro Ile Glu Gly Thr Pro Tyr Cys Phe
                1845                1850                1855

Ser Arg Asn Asp Ser Leu Ser Ser Leu Asp Phe Asp Asp Asp Asp Val
            1860                1865                1870
```

```
Asp Leu Ser Arg Glu Lys Ala Glu Leu Arg Lys Ala Lys Glu Asn Lys
       1875                1880                1885

Glu Ser Glu Ala Lys Val Thr Ser His Thr Glu Leu Thr Ser Asn Gln
   1890                1895                1900

Gln Ser Ala Asn Lys Thr Gln Ala Ile Ala Lys Gln Pro Ile Asn Arg
905                1910                1915                1920

Gly Gln Pro Lys Pro Ile Leu Gln Lys Gln Ser Thr Phe Pro Gln Ser
               1925                1930                1935

Ser Lys Asp Ile Pro Asp Arg Gly Ala Ala Thr Asp Glu Lys Leu Gln
           1940                1945                1950

Asn Phe Ala Ile Glu Asn Thr Pro Val Cys Phe Ser His Asn Ser Ser
       1955                1960                1965

Leu Ser Ser Leu Ser Asp Ile Asp Gln Glu Asn Asn Asn Lys Glu Asn
   1970                1975                1980

Glu Pro Ile Lys Glu Thr Glu Pro Pro Asp Ser Gln Gly Glu Pro Ser
985                1990                1995                2000

Lys Pro Gln Ala Ser Gly Tyr Ala Pro Lys Ser Phe His Val Glu Asp
               2005                2010                2015

Thr Pro Val Cys Phe Ser Arg Asn Ser Ser Leu Ser Ser Leu Ser Ile
           2020                2025                2030

Asp Ser Glu Asp Asp Leu Leu Gln Glu Cys Ile Ser Ser Ala Met Pro
       2035                2040                2045

Lys Lys Lys Lys Pro Ser Arg Leu Lys Gly Asp Asn Glu Lys His Ser
   2050                2055                2060

Pro Arg Asn Met Gly Gly Ile Leu Gly Glu Asp Leu Thr Leu Asp Leu
065                2070                2075                2080

Lys Asp Ile Gln Arg Pro Asp Ser Glu His Gly Leu Ser Pro Asp Ser
               2085                2090                2095

Glu Asn Phe Asp Trp Lys Ala Ile Gln Glu Gly Ala Asn Ser Ile Val
           2100                2105                2110

Ser Ser Leu His Gln Ala Ala Ala Ala Ala Cys Leu Ser Arg Gln Ala
       2115                2120                2125

Ser Ser Asp Ser Asp Ser Ile Leu Ser Leu Lys Ser Gly Ile Ser Leu
   2130                2135                2140

Gly Ser Pro Phe His Leu Thr Pro Asp Gln Glu Glu Lys Pro Phe Thr
145                2150                2155                2160

Ser Asn Lys Gly Pro Arg Ile Leu Lys Pro Gly Glu Lys Ser Thr Leu
               2165                2170                2175

Glu Thr Lys Lys Ile Glu Ser Glu Ser Lys Gly Ile Lys Gly Gly Lys
           2180                2185                2190

Lys Val Tyr Lys Ser Leu Ile Thr Gly Lys Val Arg Ser Asn Ser Glu
       2195                2200                2205

Ile Ser Gly Gln Met Lys Gln Pro Leu Gln Ala Asn Met Pro Ser Ile
   2210                2215                2220

Ser Arg Gly Arg Thr Met Ile His Ile Pro Gly Val Arg Asn Ser Ser
225                2230                2235                2240

Ser Ser Thr Ser Pro Val Ser Lys Lys Gly Pro Pro Leu Lys Thr Pro
               2245                2250                2255

Ala Ser Lys Ser Pro Ser Glu Gly Gln Thr Ala Thr Thr Ser Pro Arg
           2260                2265                2270

Gly Ala Lys Pro Ser Val Lys Ser Glu Leu Ser Pro Val Ala Arg Gln
       2275                2280                2285

Thr Ser Gln Ile Gly Gly Ser Ser Lys Ala Pro Ser Arg Ser Gly Ser
   2290                2295                2300
```

Arg Asp Ser Thr Pro Ser Arg Pro Ala Gln Gln Pro Leu Ser Arg Pro
305 2310 2315 2320

Ile Gln Ser Pro Gly Arg Asn Ser Ile Ser Pro Gly Arg Asn Gly Ile
2325 2330 2335

Ser Pro Pro Asn Lys Leu Ser Gln Leu Pro Arg Thr Ser Ser Pro Ser
2340 2345 2350

Thr Ala Ser Thr Lys Ser Ser Gly Ser Gly Lys Met Ser Tyr Thr Ser
2355 2360 2365

Pro Gly Arg Gln Met Ser Gln Gln Asn Leu Thr Lys Gln Thr Gly Leu
2370 2375 2380

Ser Lys Asn Ala Ser Ser Ile Pro Arg Ser Glu Ser Ala Ser Lys Gly
385 2390 2395 2400

Leu Asn Gln Met Asn Asn Gly Asn Gly Ala Asn Lys Lys Val Glu Leu
2405 2410 2415

Ser Arg Met Ser Ser Thr Lys Ser Ser Gly Ser Glu Ser Asp Arg Ser
2420 2425 2430

Glu Arg Pro Val Leu Val Arg Gln Ser Thr Phe Ile Lys Glu Ala Pro
2435 2440 2445

Ser Pro Thr Leu Arg Arg Lys Leu Glu Glu Ser Ala Ser Phe Glu Ser
2450 2455 2460

Leu Ser Pro Ser Ser Arg Pro Ala Ser Pro Thr Arg Ser Gln Ala Gln
465 2470 2475 2480

Thr Pro Val Leu Ser Pro Ser Leu Pro Asp Met Ser Leu Ser Thr His
2485 2490 2495

Ser Ser Val Gln Ala Gly Gly Trp Arg Lys Leu Pro Pro Asn Leu Ser
2500 2505 2510

Pro Thr Ile Glu Tyr Asn Asp Gly Arg Pro Ala Lys Arg His Asp Ile
2515 2520 2525

Ala Arg Ser His Ser Glu Ser Pro Ser Arg Leu Pro Ile Asn Arg Ser
2530 2535 2540

Gly Thr Trp Lys Arg Glu His Ser Lys His Ser Ser Ser Leu Pro Arg
545 2550 2555 2560

Val Ser Thr Trp Arg Arg Thr Gly Ser Ser Ser Ser Ile Leu Ser Ala
2565 2570 2575

Ser Ser Glu Ser Ser Glu Lys Ala Lys Ser Glu Asp Glu Lys His Val
2580 2585 2590

Asn Ser Ile Ser Gly Thr Lys Gln Ser Lys Glu Asn Gln Val Ser Ala
2595 2600 2605

Lys Gly Thr Trp Arg Lys Ile Lys Glu Asn Glu Phe Ser Pro Thr Asn
2610 2615 2620

Ser Thr Ser Gln Thr Val Ser Ser Gly Ala Thr Asn Gly Ala Glu Ser
625 2630 2635 2640

Lys Thr Leu Ile Tyr Gln Met Ala Pro Ala Val Ser Lys Thr Glu Asp
2645 2650 2655

Val Trp Val Arg Ile Glu Asp Cys Pro Ile Asn Asn Pro Arg Ser Gly
2660 2665 2670

Arg Ser Pro Thr Gly Asn Thr Pro Pro Val Ile Asp Ser Val Ser Glu
2675 2680 2685

Lys Ala Asn Pro Asn Ile Lys Asp Ser Lys Asp Asn Gln Ala Lys Gln
2690 2695 2700

Asn Val Gly Asn Gly Ser Val Pro Met Arg Thr Val Gly Leu Glu Asn
705 2710 2715 2720

Arg Leu Asn Ser Phe Ile Gln Val Asp Ala Pro Asp Gln Lys Gly Thr

```
                2725                2730                2735

Glu Ile Lys Pro Gly Gln Asn Asn Pro Val Pro Val Ser Glu Thr Asn
            2740                2745                2750

Glu Ser Ser Ile Val Glu Arg Thr Pro Phe Ser Ser Ser Ser Ser Ser
        2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
785                 2790                2795                2800

Arg Pro Ser Gln Ile Pro Thr Pro Val Asn Asn Asn Thr Lys Lys Arg
                2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val
        2835                2840


(2) INFORMATION FOR SEQ ID NO:8:

     (i) SEQUENCE CHARACTERISTICS:
          (A) LENGTH: 31 amino acids
          (B) TYPE: amino acid
          (C) STRANDEDNESS: single
          (D) TOPOLOGY: linear

    (ii) MOLECULE TYPE: peptide

   (vii) IMMEDIATE SOURCE:
          (B) CLONE: ral2(yeast)

    (xi) SEQUENCE DESCRIPTION: SEQ ID NO:8:

Leu Thr Gly Ala Lys Gly Leu Gln Leu Arg Ala Leu Arg Arg Ile Ala
1               5                   10                  15

Arg Ile Glu Gln Gly Gly Thr Ala Ile Ser Pro Thr Ser Pro Leu
            20                  25                  30


(2) INFORMATION FOR SEQ ID NO:9:

     (i) SEQUENCE CHARACTERISTICS:
          (A) LENGTH: 29 amino acids
          (B) TYPE: amino acid
          (C) STRANDEDNESS: single
          (D) TOPOLOGY: linear

    (ii) MOLECULE TYPE: peptide

    (vi) ORIGINAL SOURCE:
          (A) ORGANISM: Homo sapiens

   (vii) IMMEDIATE SOURCE:
          (B) CLONE: m3(mAChR)

    (xi) SEQUENCE DESCRIPTION: SEQ ID NO:9:

Leu Tyr Trp Arg Ile Tyr Lys Glu Thr Glu Lys Arg Thr Lys Glu Leu
1               5                   10                  15

Ala Gly Leu Gln Ala Ser Gly Thr Glu Ala Glu Thr Glu
            20                  25


(2) INFORMATION FOR SEQ ID NO:10:

     (i) SEQUENCE CHARACTERISTICS:
          (A) LENGTH: 29 amino acids
          (B) TYPE: amino acid
          (C) STRANDEDNESS: single
          (D) TOPOLOGY: linear

    (ii) MOLECULE TYPE: peptide
```

(vi) ORIGINAL SOURCE:
(A) ORGANISM: Homo sapiens (vii) IMMEDIATE SOURCE:
(B) CLONE: MCC (xi) SEQUENCE DESCRIPTION: SEQ ID NO:10:

```
Leu Tyr Pro Asn Leu Ala Glu Glu Arg Ser Arg Trp Glu Lys Glu Leu
1               5                   10                  15

Ala Gly Leu Arg Glu Glu Asn Glu Ser Leu Thr Ala Met
            20                  25
```

(2) INFORMATION FOR SEQ ID NO:11:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:11:

```
GTATCAAGAC TGTGACTTTT AATTGTAGTT TATCCATTTT                          40
```

(2) INFORMATION FOR SEQ ID NO:12:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:12:

```
TTTAGAATTT CATGTTAATA TATTGTGTTC TTTTTAACAG                          40
```

(2) INFORMATION FOR SEQ ID NO:13:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:13:

```
GTAGATTTTA AAAAGGTGTT TTAAAATAAT TTTTTAAGCT                          40
```

(2) INFORMATION FOR SEQ ID NO:14:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:14:

AAGCAATTGT TGTATAAAAA CTTGTTTCTA TTTTATTTAG 40

(2) INFORMATION FOR SEQ ID NO:15:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:15:

GTAACTTTTC TTCATATAGT AAACATTGCC TTGTGTACTC 40

(2) INFORMATION FOR SEQ ID NO:16:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:16:

NNNNNNNNNN NNNGTCCCTT TTTTTAAAAA AAAAAAATAG 40

(2) INFORMATION FOR SEQ ID NO:17:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:17:

GTAAGTAACT TGGCAGTACA ACTTATTTGA AACTTTAATA 40

(2) INFORMATION FOR SEQ ID NO:18:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:18:

ATACAAGATA TTGATACTTT TTTATTATTT GTGGTTTTAG 40

(2) INFORMATION FOR SEQ ID NO:19:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:19:

GTAAGTTACT TGTTTCTAAG TGATAAAACA GYGAAGAGCT 40

(2) INFORMATION FOR SEQ ID NO:20:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:20:

AATAAAAACA TAACTAATTA GGTTTCTTGT TTTATTTTAG 40

(2) INFORMATION FOR SEQ ID NO:21:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:21:

GTTAGTAAAT TSCCTTTTTT GTTTGTGGGT ATAAAAATAG 40

(2) INFORMATION FOR SEQ ID NO:22:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:22:

ACCATTTTTG CATGTACTGA TGTTAACTCC ATCTTAACAG 40

(2) INFORMATION FOR SEQ ID NO:23:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:23:

GTAAATAAAT TATTTTATCA TATTTTTTAA AATTATTTAA 40

(2) INFORMATION FOR SEQ ID NO:24:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:24:

CATGATGTTA TCTGTATTTA CCTATAGTCT AAATTATACC ATCTATAATG TGCTTAATTT 60

TTAG 64

(2) INFORMATION FOR SEQ ID NO:25:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:25:

GTAACAGAAG ATTACAAACC CTGGTCACTA ATGCCATGAC TACTTTGCTA AG 52

(2) INFORMATION FOR SEQ ID NO:26:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:26:

GGATATTAAA GTCGTAATTT TGTTTCTAAA CTCATTTGGC CCACAG 46

(2) INFORMATION FOR SEQ ID NO:27:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:27:

GTATGTTCTC TATAGTGTAC ATCGTAGTGC ATGTTTCAAA 40

(2) INFORMATION FOR SEQ ID NO:28:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:28:

CATCATTGCT CTTCAAATAA CAAAGCATTA TGGTTTATGT TGATTTTATT TTTCAG 56

(2) INFORMATION FOR SEQ ID NO:29:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:29:

GTAAGACAAA AATGTTTTTT AATGACATAG ACAATTACTG GTG 43

(2) INFORMATION FOR SEQ ID NO:30:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:30:

TTAGATGATT GTCTTTTTCC TCTTGCCCTT TTTAAATTAG 40

(2) INFORMATION FOR SEQ ID NO:31:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:31:

GTATGTTTTT ATAACATGTA TTTCTTAAGA TAGCTCAGGT ATGA 44

(2) INFORMATION FOR SEQ ID NO:32:

(i) SEQUENCE CHARACTERISTICS:
(A) LENGTH: 54 base pairs (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:32:

GCTTGGCTTC AAGTTGNCTT TTTAATGATC CTCTATTCTG TATTTAATTT ACAG 54

(2) INFORMATION FOR SEQ ID NO:33:

(i) SEQUENCE CHARACTERISTICS:
(A) LENGTH: 65 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:33:

GTACTATTTA GAATTTCACC TGTTTTTCTT TTTTCTCTTT TTCTTTGAGG CAGGGTCTCA 60

CTCTG 65

(2) INFORMATION FOR SEQ ID NO:34:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:34:

GCAACTAGTA TGATTTTATG TATAAATTAA TCTAAAATTG ATTAATTTCC AG 52

(2) INFORMATION FOR SEQ ID NO:35:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:35:

GTACCTTTGA AAACATTTAG TACTATAATA TGAATTTCAT GT 42

(2) INFORMATION FOR SEQ ID NO:36:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:36:

CCAACTCNAA TTAGATGACC CATATTCAGA AACTTACTAG 40

(2) INFORMATION FOR SEQ ID NO:37:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:37:

GTATATATAG AGTTTTATAT TACTTTTAAA GTACAGAATT CATACTCTCA AAAA 54

(2) INFORMATION FOR SEQ ID NO:38:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:38:

ATTGTGACCT TAATTTTGTG ATCTCTTGAT TTTTATTTCA G 41

(2) INFORMATION FOR SEQ ID NO:39:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:39:

TCCCCGCCTG CCGCTCTC 18

(2) INFORMATION FOR SEQ ID NO:40:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:40:

GCAGCGGCGG CTCCCGTG 18

(2) INFORMATION FOR SEQ ID NO:41:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:41:

GTGAACGGCT CTCATGCTGC 20

(2) INFORMATION FOR SEQ ID NO:42:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:42:

ACGTGCGGGG AGGAATGGA 19

(2) INFORMATION FOR SEQ ID NO:43:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:43:

ATGATATCTT ACCAAATGAT ATAC 24

(2) INFORMATION FOR SEQ ID NO:44:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:44:

TTATTCCTAC TTCTTCTATA CAG 23

(2) INFORMATION FOR SEQ ID NO:45:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:45:

TACCCATGCT GGCTCTTTTT C 21

(2) INFORMATION FOR SEQ ID NO:46:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:46:

TGGGGCCATC TTGTTCCTGA 20

(2) INFORMATION FOR SEQ ID NO:47:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:47:

ACATTAGGCA CAAAGCTTGC AA 22

(2) INFORMATION FOR SEQ ID NO:48:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:48:

ATCAAGCTCC AGTAAGAAGG TA 22

(2) INFORMATION FOR SEQ ID NO:49:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:49:

TGCGGCTCCT GGGTTGTTG 19

(2) INFORMATION FOR SEQ ID NO:50:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:50:

GCCCCTTCCT TTCTGAGGAC 20

(2) INFORMATION FOR SEQ ID NO:51:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:51:

TTTTCTCCTG CCTCTTACTG C 21

(2) INFORMATION FOR SEQ ID NO:52:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:52:

ATGACACCCC CCATTCCCTC 20

(2) INFORMATION FOR SEQ ID NO:53:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:53:

CCACTTAAAG CACATATATT TAGT 24

(2) INFORMATION FOR SEQ ID NO:54:

(i) SEQUENCE CHARACTERISTICS:
(A) LENGTH: 22 base pairs
(B) TYPE: nucleic acid
(C) STRANDEDNESS: single (D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:54:

GTATGGAAAA TAGTGAAGAA CC 22

(2) INFORMATION FOR SEQ ID NO:55:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:55:

TTCTTAAGTC CTGTTTTTCT TTTG 24

(2) INFORMATION FOR SEQ ID NO:56:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:56:

TTTAGAACCT TTTTTGTGTT GTG 23

(2) INFORMATION FOR SEQ ID NO:57:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:57:

CTCAGATTAT ACACTAAGCC TAAC 24

(2) INFORMATION FOR SEQ ID NO:58:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:58:

CATGTCTCTT ACAGTAGTAC CA 22

(2) INFORMATION FOR SEQ ID NO:59:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:59:

AGGTCCAAGG GTAGCCAAGG 20

(2) INFORMATION FOR SEQ ID NO:60:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:60:

TAAAAATGGA TAAACTACAA TTAAAAG 27

(2) INFORMATION FOR SEQ ID NO:61:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:61:

AAATACAGAA TCATGTCTTG AAGT 24

(2) INFORMATION FOR SEQ ID NO:62:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:62:

ACACCTAAAG ATGACAATTT GAG 23

(2) INFORMATION FOR SEQ ID NO:63:

(i) SEQUENCE CHARACTERISTICS:
(A) LENGTH: 24 base pairs (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:63:

TAACTTAGAT AGCAGTAATT TCCC 24

(2) INFORMATION FOR SEQ ID NO:64:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:64:

ACAATAAACT GGAGTACACA AGG 23

(2) INFORMATION FOR SEQ ID NO:65:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:65:

ATAGGTCATT GCTTCTTGCT GAT 23

(2) INFORMATION FOR SEQ ID NO:66:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:66:

TGAATTTTAA TGGATTACCT AGGT 24

(2) INFORMATION FOR SEQ ID NO:67:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:67:

CTTTTTTTGC TTTTACTGAT TAACG 25

(2) INFORMATION FOR SEQ ID NO:68:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:68:

TGTAATTCAT TTTATTCCTA ATAGCTC 27

(2) INFORMATION FOR SEQ ID NO:69:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:69:

GGTAGCCATA GTATGATTAT TTCT 24

(2) INFORMATION FOR SEQ ID NO:70:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:70:

CTACCTATTT TTATACCCAC AAAC 24

(2) INFORMATION FOR SEQ ID NO:71:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:71:

AAGAAAGCCT ACACCATTTT TGC 23

(2) INFORMATION FOR SEQ ID NO:72:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:72:

GATCATTCTT AGAACCATCT TGC 23

(2) INFORMATION FOR SEQ ID NO:73:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:73:

ACCTATAGTC TAAATTATAC CATC 24

(2) INFORMATION FOR SEQ ID NO:74:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:74:

GTCATGGCAT TAGTGACCAG 20

(2) INFORMATION FOR SEQ ID NO:75:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:75:

AGTCGTAATT TTGTTTCTAA ACTC 24

(2) INFORMATION FOR SEQ ID NO:76:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:76:

TGAAGGACTC GGATTTCACG C 21

(2) INFORMATION FOR SEQ ID NO:77:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:77:

TCATTCACTC ACAGCCTGAT GAC 23

(2) INFORMATION FOR SEQ ID NO:78:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:78:

GCTTTGAAAC ATGCACTACG AT 22

(2) INFORMATION FOR SEQ ID NO:79:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:79:

AAACATCATT GCTCTTCAAA TAAC 24

(2) INFORMATION FOR SEQ ID NO:80:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:80:

TACCATGATT TAAAAATCCA CCAG 24

(2) INFORMATION FOR SEQ ID NO:81:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:81:

GATGATTGTC TTTTTCCTCT TGC 23

(2) INFORMATION FOR SEQ ID NO:82:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:82:

CTGAGCTATC TTAAGAAATA CATG 24

(2) INFORMATION FOR SEQ ID NO:83:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:83:

TTTTAAATGA TCCTCTATTC TGTAT 25

(2) INFORMATION FOR SEQ ID NO:84:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:84:

ACAGAGTCAG ACCCTGCCTC AAAG 24

(2) INFORMATION FOR SEQ ID NO:85:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:85:

TTTCTATTCT TACTGCTAGC ATT 23

(2) INFORMATION FOR SEQ ID NO:86:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:86:

ATACACAGGT AAGAAATTAG GA 22

(2) INFORMATION FOR SEQ ID NO:87:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:87:

TAGATGACCC ATATTCTGTT TC 22

(2) INFORMATION FOR SEQ ID NO:88:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:88:

CAATTAGGTC TTTTTGAGAG TA 22

(2) INFORMATION FOR SEQ ID NO:89:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:89:

GTTACTGCAT ACACATTGTG AC 22

(2) INFORMATION FOR SEQ ID NO:90:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:90:

GCTTTTTGTT TCCTAACATG AAG 23

(2) INFORMATION FOR SEQ ID NO:91:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:91:

TCTCCCACAG GTAATACTCC C 21

(2) INFORMATION FOR SEQ ID NO:92:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:92:

GCTAGAACTG AATGGGGTAC G 21

(2) INFORMATION FOR SEQ ID NO:93:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:93:

CAGGACAAAA TAATCCTGTC CC 22

(2) INFORMATION FOR SEQ ID NO:94:

(i) SEQUENCE CHARACTERISTICS:
(A) LENGTH: 24 base pairs
(B) TYPE: nucleic acid
(C) STRANDEDNESS: single (D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:94:

ATTTTCTTAG TTTCATTCTT CCTC 24

*(2) INFORMATION FOR SEQ ID NO: 95:*

*(i) SEQUENCE CHARACTERISTICS:*
*(A) LENGTH: 25 base pairs*
*(B) TYPE: nucleic acid*
*(C) STRANDEDNESS: single*
*(D) TOPOLOGY: linear*

*(ii) MOLECULE TYPE: cDNA*

*(vi) ORIGINAL SOURCE:*
*(A) ORGANISM: Homo sapiens*

*(xi) SEQUENCE DESCRIPTION: SEQ ID NO:95:*

*AGAAGGATCC CTTGTGCAGT GTGGA 25*

*(2) INFORMATION FOR SEQ ID NO: 96:*

*(i) SEQUENCE CHARACTERISTICS:*
*(A) LENGTH: 24 base pairs*
*(B) TYPE: nucleic acid*
*(C) STRANDEDNESS: single*
*(D) TOPOLOGY: linear*

*(ii) MOLECULE TYPE: cDNA*

*(vi) ORIGINAL SOURCE:*
*(A) ORGANISM: Homo sapiens*

*(xi) SEQUENCE DESCRIPTION: SEQ ID NO:96:*

*GACAGGATCC TGAAGCTGAG TTTG 24*

*(2) INFORMATION FOR SEQ ID NO: 97:*

*(i) SEQUENCE CHARACTERISTICS:*
*(A) LENGTH: 18 base pairs*
*(B) TYPE: nucleic acid*
*(C) STRANDEDNESS: single*
*(D) TOPOLOGY: linear*

*(ii) MOLECULE TYPE: cDNA*

*(vi) ORIGINAL SOURCE:*
*(A) ORGANISM: Homo sapiens*

*(xi) SEQUENCE DESCRIPTION: SEQ ID NO:97:*

*TCAGAAAGTG CTGAAGAG 18*

*(2) INFORMATION FOR SEQ ID NO: 98:*

*(i) SEQUENCE CHARACTERISTICS:*
*(A) LENGTH: 19 base pairs*
*(B) TYPE: nucleic acid*
*(C) STRANDEDNESS: single*
*(D) TOPOLOGY: linear*

*(ii) MOLECULE TYPE: cDNA*

*(vi) ORIGINAL SOURCE:*
*(A) ORGANISM: Homo sapiens*

*(xi) SEQUENCE DESCRIPTION: SEQ ID NO:98:*

GGAATAATTA GGTCTCCAA 19

(2) INFORMATION FOR SEQ ID NO: 99:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:99:

GCAAATCCTA AGAGAGAACA A 21

(2) INFORMATION FOR SEQ ID NO: 100:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:100:

GATGGCAAGC TTGAGCCAG 19

(2) INFORMATION FOR SEQ ID NO: 101:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:101:

GTTCCAGCAG TGTCACAG 18

(2) INFORMATION FOR SEQ ID NO: 102:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:102:

GGGAGATTTC GCTCCTGA 18

TABLE I

APC EXONS

| EXON NUCLEOTIDES[1] | EXON BOUNDARY SEQUENCE[2] |
|---|---|
| 822 to 930 | ctgatgttatcgtatttacctatagtctaaattataccatctataatgtgcttaatttttag/GGTTCA . . . |
| | . . . ACCAAG/gtaacagaagattacaaaccctggtcactaatgccatgactactttgctaag |
| 931 to 1309 | ggatattaaagtcgtaattttgtttctaaactcatttggcccacag/GTGGAA . . . |
| | . . . ATCCAA/gtatgttctctatagtgtacatcgtagtgcatg |
| 1310 to 1405 | catcattgctcttcaaataacaaagcattatggtttatgttgattttatttttcag/TGCCAG . . . |
| | . . . AACTAG/gtaagacaaaaatgttttaatgacatagacaattactggtg |
| 1406 to 1545 | tagatgattgtctttttcctcttgcccttttttaaattag/GGGGAC . . . |
| | . . . AACAAG/gtatgttttataacatgtatttcttaagatagctcggtatga |
| 1546 to 1623 | gcttggcttcaagttgtctttttaatgatcctctattctgtatttaatttacag/GCTACG . . . |
| | . . . CAGCAG/gtactatttagaatttcacctgtttttctttttctctttttctttgaggcagggtctcactctg |
| 1624 to 1740 | gcaactagtatgattttatgtataaataattctaaaattgattaatttgcag/GTTATT . . . |
| | . . . AAAAAG/gtacctttgaaaacatttgtactataatatgaatttcatgt |
| 1741 to 1955 | caactctaattagatgacccatattcagaaacttactag/GAATCA . . . |
| | . . . CCACAG/gtatatatagatttatattacttttaagtacagaattcatactctcaaaa |
| 1956 to 8973 | tcttgatttttatttcag/GCAAAT . . . |
| | . . . GGTATTTATGCAAAAAAAAATGTTTTTGT |

[1]Relative to predicted translation initiation site
[2]Small case letters represent introns, large case letters represent exons
[3]The entire 3' end of the cloned APC cDNA (nt 1956-8973) appeared to be encoded in this exon, as indicated by restriction endonuclease mapping and sequencing of cloned genomic DNA. The ORF ended at at 8535. The extreme 3' end of the APC transcript has not yet been indentified.
[4]The first line of sequence is (SEQ ID NO: 24); the second line of sequence is (SEQ ID NO: 25); the third line of sequence is (SEQ ID NO: 26); the fourth line of sequence is (SEQ ID NO: 27); the fifth line of sequence is (SEQ ID NO: 28); the sixth line of sequence is (SEQ ID NO: 29); the seventh line of sequence is (SEQ ID NO: 30); the eighth line of sequence is (SEQ ID NO: 31); the ninth line of sequence is (SEQ ID NO: 32); the tenth line of sequence is (SEQ ID NO: 33); the eleventh line of sequence is (SEQ ID NO: 34); the twelfth line of sequence is (SEQ ID NO: 35); the thirteenth line of sequence is (SEQ ID NO: 36); the fourteenth line of sequence is (SEQ ID NO: 37); the fifteenth line of sequence is (SEQ ID NO: 38); and the sixteenth line of sequence is (SEQ ID NO: 1).

TABLE IIA

Germline mutations of the APC gene in FAP and GS Patients

| Patient | Codon | Nucleotide Change | Amino Acid Change | Age | Extra-colonic Disease |
|---|---|---|---|---|---|
| 93 | 279 | TCA → TGA | Ser → Stop | 39 | Mindibular Osteoma |
| 24 | 301 | CGA → TGA | Arg → Stop | 46 | None |
| 34 | 301 | CGA → TGA | Arg → Stop | 27 | Desmoid Tumor |
| 21 | 413 | CGC → TGC | Arg → Cys | 24 | Mandibular Osteoma |
| 60 | 712 | TCA → TGA | Ser → Stop | 37 | Mandibular Osteoma |
| 3746 | 243 | CAGAG → CAG | splice-junction | | |
| 3460 | 301 | CGA → TGA | Arg → stop | | |
| 3827 | 456 | CTTTCA → CTTCA | frameshift | | |
| 3712 | 500 | T → G | Tyr → Stop | | |

*The mutated nucleotides are underlined.

TABLE IIB

Somatic Mutations in Sporadic CRC Patients

| PATIENT | CODON[1] | NUCLEOTIDE CHANGE | AMINO ACID CHANGE |
|---|---|---|---|
| T35 | MCC 12 GAG/gtaaga | GAG/gtaaga → Donor) | (Splice |
| T16 | MCC 145 | vtcag/GGA → atcag/GGA | (Splice Acceptor) |
| T47 | MCC 267 | CGG → CTG | Arg → Leu |
| T81 | MCC 490 | TCG → TTG | Ser → Leu |
| T35 | MCC 506 | CGG → CAG | Arg → Gln |
| T91 | MCC 698 | GCT 3 G TT | Ala → Val |
| T34 | APC 288 | CCAGT → CCCAGCCAGT | (Insertion) |
| T27 | APC 331 | CGA → TGA | Arg → Stop |
| T135 | APC 437 | CAA/gtaa → CAA/gcaa | (Splice Donor) |
| T201 | APC 1338 | CAG → TAG | Gln → Stop |

For splice site mutations, the codon nearest to the mutation is listed

The underlined nucleotides were mutant; small case letters represent introns, large case letters represent exons

TABLE III

Sequences of Primers Used for SSCP Analyses

| Exon | Primer 1 | Primer 2 |
|---|---|---|
| | DP1 | |
| | UP-TCCCCGCCTGCCGCTCTC | RP-GCAGCGGCGGCTCCCGTG |
| | UP-GTGAACGGCTCTCATGCTGC | RP-ACGTGCGGGGAGGAATGGA |
| | UP-ATGATATCTTACCAAATGATATAC | RP-TTATTCCTACTTCTTCTATACAG |
| | UP-TACCCATGCTGGCTCTTTTTC | RP-TGGGGCCATCTTGTTCCTGA |
| | UP-ACATTAGGCACAAAGCTTGCAA | RP-ATCAAGCTCCAGTAAGAAGGTA |
| | SRP19 | |
| | UP-TGCGGCTCCTGGGTTGTTG | RP-GCCCCTTCCTTTCTGAGGAC |
| | UP-TTTTCTCCTGCCTCTTACTGC | RP-ATGACACCCCCCATTCCCTC |
| | UP-CCACTTAAAGCACATATATTTAGT | RP-GTATGGAAAATAGTGAAGAACC |
| | UP-TTCTTAAGTCCTGTTTTTCTTTTG | RP-TTTAGAACCTTTTTTGTGTTGTG |
| | UP-CTCAGATTATACACTAAGCCTAAC | RP-CATGTCTCTTACAGTAGTACCA |
| | DP2.5 | |
| | UP-AGGTCCAAGGGTAGCCAAGG* | RP-TAAAAATGGATAAACTACAATTAAAAG |
| | UP-AAATACAGAATCATGTCTTGAAGT | RP-ACACCTAAAGATGACAATTTGAG |
| | UP-TAACTTAGATAGCAGTAATTTCCC* | RP-ACAATAAACTGGAGTACACAAGG |
| | UP-ATAGGTCATTGCTTCTTGCTGAT* | RP-TGAATTTTAATGGATTACCTAGGT |
| | UP-CTTTTTTTGCTTTTACTGATTAACG | RP-TGTAATTCATTTTATTCTAATACCTC |
| | UP-GGTAGCCATAGTAGATTATTTCT | RP-CTACCTATTTTTATACCCACAAAC |
| | UP-AAGAAAGCCTACACCATTTTTGC | RP-GATCATTCTTAGAACCATCTTGC |
| | UP-ACCTTAGTCTAAATTATACCATC | RP-GTCATGGCATTACTGACCAG |
| | UP-AGTCGTAATTTTGTTTCTAAACTC | RP-TGAAGGACTCCGATTTCACCC* |
| | UP-TCATTCACTCACAGCTGATGAC* | RP-GCTTTGAAACATGCACTACGAT |
| | UP-AAACATCATTGCTCTTCAAATAAC | RP-TACCATGATTTAAAAATCCACCAG |
| | UP-GATGATTGTCTTTTTCCTCTTGC | RP-CTGAGCTATCTTAAGAAATACATG |
| | UP-TTTTAAATGATCCTCTATTCTGTAT | RP-ACAGAGTCAGACCCTCCCTCAAAG |
| | UP-TTTCTATTCTTACTGCTAGCATT | RP-ATACACAGGTAAGAAATTAGGA |
| | UP-TAGATGACCCATATTCTCTTTC | RP-CAATTAGGTCTTTTTGAGAGTA |
| 3-A | UP-GTTACTGCATACACATTGTGAC | RP-GCTTTTTGTTTCGTAACATGAAG* |
| -B | UP-AGTACAAGGATGCCAATATTATG* | RP-ACTTCTATCTTTTTCAGAACGAG* |
| -C | UP-ATTGAATACTACAGTGTTACCC* | RP-CTTGTATTCTAATTTGGCATAAGG* |
| -D | UP-CTGCCCATACACATTCAAACAC* | RP-TGTTTGCGTCTTGCCCATCTT* |
| -E | UP-AGTCTTAAATATTCAGATGAGCAG* | RP-GTTTCTCTTCATTATATTTTATGCTA* |
| -F | UP-AAGCCTACCAATTATAGTGAACG* | RP-AGCTGATGACAAAGATGATAATC* |
| -G | UP-AAGAAACAATACAGACTTATTGTG* | RP-ATGAGTGGGGTCTCCTGAAC* |
| -H | UPATCTCCCTCCAAAAGTGGTGC* | RP-TCCATCTGGAGTACTTTCTGTG* |
| -I | UP-AGTAAATGCTGCAGTTCAGAGG* | RP-CCGTGGCATATCATCCCCC* |
| -J | UP-CCCAGACTGCTTCAAAATTACC* | RP-GAGCCTCATCTGTACTTCTGC* |
| -K | UP-CCCTCCAAATGAGTTAGCTGC* | RP-TTGTGGTATAGGTTTTACTGGTG* |
| -L | UP-ACCCAACAAAAATCAGTTAGATG* | RP-GTGGCTGGTAACTTTAGCCTC* |
| -N | UP-ATGATGTTGACCTTTCCAGGG* | RP-ATTGTGTAACTTTTCATCAGTTGC* |
| -O | UP-AAGATGACCTGTTGCAGGAATG* | RP-GAATCAGACCAAGCTTGTCTAGAT* |
| -P | UP-CAATAGTAAGTAGTTTACATCAAG* | RP-AAACAGGACTTGTACTGTAGGA* |
| -Q | UP-CAGCCCCTTCAAGCAAACATC* | RP-GAGGACTTATTCCATTTCTACC* |
| -R | UP-CAGTCTCCTGGCCGAACTC* | RP-GTTGACTGGCGTACTAATACAG* |
| -S | UP-TGGTAATGGAGCCAATAAAAAGG* | RP-TGGGACTTTTCGCCATCCAC* |
| -T | UP-TGTCTCTATCCACACATTCGTC* | RP-ATGTTTTTCATCCTCACTTTTTGC* |
| -U | UP-GGAGAAGAACTGGAAGTTCATC* | RP-TTGAATCTTTAATGTTTGGATTTGC* |
| -V | UP-TCTCCCACAGGTAATACTCCC | RP-GCTACAACTGAATGGGGTACG |
| -W | UP-CAGGACAAAATAATCCTGTCCC | RP-ATTTTCTTACTTTCATTCTTCCTC |

All primers are read in the 5' to 3' direction. the first primer in each pair lies 5' of the exon ir amplifies: the second primer lies 3' of the exon it amplifies. Primers that lie within the exon are identified by an asterisk. UP represnets the - 2ImI3 universal primer sequence: RP represnets the MI3 reverse primer sequence.

Primer 1 of DP1 exons 1, 2, 3, 4, and 5 are shown in SEQ ID NOS: 39, 41, 43, 45, and 47, respectively. Primer 2 of DP1 exons 1, 2, 3, 4, and 5 are shown in SEQ ID NOS: 40, 42, 44, 46, and 48, respectively. Primer 1 of SRP19 exons 1, 2, 3, 4, and 5 are shown in SEQ ID NOS: 49, 51, 53, 55, and 57, respectively. Primer 2 of SRP19 exons 1, 2, 3, 4, and 5 are shown in SEQ ID NOS: 50, 52, 54, 56, and 58, respectively. Primer 1 of DP2.5 exons 1, 2, 3, 4, 5, 6, 7, 8, 9, 9a, 10, 11, 12, 13, 14, and 15-A are shown in SEQ ID NOS: 59, 61, 63, 65, 67, 69, 71, 73, 75, 77, 79, 81, 83, 85, 87, and 89, respectively. Primer 2 of DP2.5 exons 1, 2, 3, 4, 5, 6, 7, 8, 9, 9a, 10, 11, 12, 13, 14, and 15-A are shown in SEQ ID NOS: 60, 62, 64, 66, 68, 70, 72, 74, 76, 78, 80, 82, 84, 86, 88, and 90, respectively. Primer 1 and primer 2 of DP2.5 exon 15-B, C, D, E, F, G, H, I, J, K, L, M, N, O, P, Q, R, S, T, and U are shown in SEQ ID NO: 1.

TABLE IV

Seven Different Versions of the 20-Amino Acid Repeat

| Consensus: | F | . | V | E | . | T | P | . | C | F | S | R | . | S | S | L | S | S | L | S |
|---|---|---|---|---|---|---|---|---|---|---|---|---|---|---|---|---|---|---|---|---|
| 1262: | Y | C | V | E | D | T | P | I | C | F | S | R | C | S | S | L | S | S | L | S |
| 1376: | H | Y | V | Q | E | T | P | L | M | F | S | R | C | T | S | V | S | S | L | D |
| 1492: | F | A | T | E | S | T | P | D | G | F | S | C | S | S | S | L | S | A | L | S |
| 1643: | Y | C | V | E | G | T | P | I | N | F | S | T | A | T | S | L | S | D | L | T |
| 1848: | T | P | I | E | G | T | P | Y | C | F | S | R | N | D | S | L | S | S | L | D |
| 1953: | F | A | I | E | N | T | P | V | C | P | S | H | N | S | S | L | S | S | L | S |
| 2013: | F | H | V | E | D | T | P | V | C | F | S | R | N | S | S | L | S | S | L | S |

Numbers denote the first amino acid of each repeat. The consensus sequence at the top reflects a majority amino acid at a given position.

We claim:

1. A cDNA molecule having the nucleotide sequence shown in SEQ ID NO: 1 or its complement.

2. An isolated DNA molecule having the nucleotide sequence shown in SEQ ID NO:1 or its complement.

3. A cDNA molecule which encodes a protein having the amino acid sequence shown in [FIG. 3 or 7 (]SEQ ID NO: 7 or 2[)].

4. An isolated DNA molecule which encodes a protein having the amino acid sequence shown in [FIG. 3 or 7 (]SEQ ID NO: 7 or 2[)].

5. A nucleic acid probe complementary to all or part of human wild-type APC gene coding sequences or the complement of said sequences such that said probe selectively hybridizes under stringent conditions to said APC gene or identifies endogenous, random modifications in said APC gene.

6. The nucleic acid probe of claim 5 which hybridizes to all or part of an exon selected from the group consisting of: (1) nucleotides 822 to 930; (2) nucleotides 931 to to 1309; (3) nucleotides 1406 to 1545; and (4) nucleotides 1956 to 2256 *as shown in SEQ ID NO: 1*.

7. A set of probes useful for detecting alteration of wild-type APC genes comprising a plurality of nucleic acid probes wherein said set is complementary to all nucleotides of the APC gene coding sequences as shown in SEQ ID NO:1 or the complement of said sequences.

8. A pair of single stranded DNA primers for determination of a nucleotide sequence of an APC gene by polymerase chain reaction, the sequence of said primers being derived from said APC gene, wherein the use of said primers in a polymerase chain reaction results in synthesis of DNA having all or part of the sequence shown in [FIG. 7 (]SEQ ID NO:1[)].

9. The pair of primers of claim 8 which have restriction enzyme sites at each 5' end.

10. The pair of primers of claim 8 having sequences complementary to all or part of one or more APC introns.

* * * * *

UNITED STATES PATENT AND TRADEMARK OFFICE

CERTIFICATE OF CORRECTION

PATENT NO.: Re. 36,713

DATED: May 23, 2000

INVENTORS: Bert VOGELSTEIN, *et al.*

It is certified that an error appears in the above-identified patent and that said Letters Patent is hereby corrected as shown below:

In [75] Inventors, "Albertson" has been replaced with --Albertsen--.

In [73] Asignees, "Zeneca" has been replaced with --Zeneca Limited--.

In [57] Abstract, line 2, "hum" has been replaced with --human--;

line 4, "wel" has been replaced with --well--;

line 5, "patents" has been replaced with --patients--;

line 6, "tissue" has been replaced with --tissues--.

Signed and Sealed this

First Day of May, 2001

*Attest:*

Nicholas P. Godici

NICHOLAS P. GODICI

*Attesting Officer*

*Acting Director of the United States Patent and Trademark Office*